(12) United States Patent
Carpino et al.

(10) Patent No.: US 7,812,158 B2
(45) Date of Patent: Oct. 12, 2010

(54) COUPLING AGENTS FOR PEPTIDE SYNTHESIS

(75) Inventors: Louis A. Carpino, Amherst, MA (US); Jusong Xia, Moore, SC (US); Chongwu Zhang, Dayton, NJ (US); Calin Dan Sferdean, Riverview, MI (US)

(73) Assignee: University of Massachusetts, Boston, MA (US)

( * ) Notice: Subject to any disclaimer, the term of this patent is extended or adjusted under 35 U.S.C. 154(b) by 902 days.

(21) Appl. No.: 10/577,352

(22) PCT Filed: Nov. 1, 2004

(86) PCT No.: PCT/US2004/036428

§ 371 (c)(1), (2), (4) Date: Nov. 22, 2006

(87) PCT Pub. No.: WO2005/042562

PCT Pub. Date: May 12, 2005

(65) Prior Publication Data

US 2007/0112196 A1    May 17, 2007

Related U.S. Application Data

(60) Provisional application No. 60/516,167, filed on Oct. 31, 2003.

(51) Int. Cl.
C07D 487/04 (2006.01)
C07D 471/04 (2006.01)
C07D 403/12 (2006.01)

(52) U.S. Cl. ........................ 544/236; 544/232

(58) Field of Classification Search .................. 544/244, 544/279, 319
See application file for complete search history.

(56) References Cited

U.S. PATENT DOCUMENTS 5,698,675 A    12/1997 Carpino
6,277,858 B1 *  8/2001 Walter .................... 514/260.1

FOREIGN PATENT DOCUMENTS

EP      0638842       2/1995
GB      2193213       2/1988
WO      2005007634    1/2005
WO      WO 2005/007634 1/2005

OTHER PUBLICATIONS

Carpino et al. J. Org. Chem. 2004, 69, 54-61.*
F. Hoffmann, L. Jäger, C Griehl; Synthesis and Chemical Constitution of Diphenoxyphosphoryl Derivatives and Phosphonium Salts as Coupling Reagents for Peptide Segment Condensation; Phosphorus, Sulfur and Silicon, 2003, vol. 178:299-309; Taylor & Francis.
Griehl C, Jager L, Plass M and Kolbe A; Carboxyactivation of Peptide Fragments with New Coupling Reagents in Peptides, 1996 Proceedings of the 24$^{th}$ European Peptide Symposium Sep. 8-13, 1996; 437-438, The European Peptide Society, (Robert Ramage & Roger Epton, Eds.) 1998.
Carpino L, Xia J and El-Faham A; 3-Hydroxy-4-oxo-3,4-dihydro-5-azabenzo-1,2,3-triazene; J. Org. Chem. 2004, 69, 54-61.
Carpino L, Xia J, Zhang C, and El-Faham A; Organophosphorus and Nitro-Substituted Sulfonate Esters of 1-Hydroxy-7-azabenzotriazole as Highly Efficient Fast-Acting Peptide Coupling Reagents; J. Org. Chem. 2004, 69, 62-71.
Chemical Abstracts, vol. 71, No. 9, 1969, Columbus, Ohio, US; abstract No. 39003u, p. 303 col. 1 XP002505421 *abstract* & JP 06 908508 B (Yoshitomi) Apr. 21, 1969.
Carpino L A et al: "Efficiency in peptide coupling: 1-hydroxy-7-azabenzotriozole vs 3,4-dihydro-3-hydroxy-4-oxo-1,2,3-benzotriazine" Journal of Organic Chemicstry, American Chemcial Society, Easton,; US, vol. 60, Jan. 1, 1995, pp. 3561-3564, XP002982632 ISSN: 0022-3263 *p. 3561*.
S. Kim: "benzotriazol-l-yl diethyl phosphate." Tetrahedron Letters, vol. 26, No. 10, 1985, pp. 1341-1342, XP002505418 Nlelsevier, Amsterdam. *p. 1341.*
Campagne J-M et al: "(1H-Benzotriazol-1-Yloxy)Tris(Dimethylamino)Phosphonium Hexafluorophosphate- and (1H-Benzotriazol-1-Yloxy)Tripyroolidinophosp Honium Hexafluorophosphate-Mediated Activation of Monophosphonate Esters:Synthesis of Mixed Phosphonate Diesters, the Reactivity of the Benzotriazolyl Phosphoneic Esters Vs TH" Journal of Organic Chemistry, American Chemcial Society, Easton,; US, vol. 60, No. 16, 1, 1995.
I. Furukawa et al.: "synthesis of polymaides with [(1,2,3-benzotriazine-4-one(-3-yl]diphenyl phosphate as a new activating agent." Journal of Macromolecular Sci.-Chemistry, vol. a26, No. 5, 1989, pp. 761-771, XP008098954 en *p. 761-p. 764; compound BTDP*.
M. Goodman et al.: "new reagents, reactions, and peptidomimetics for drug design" Biopolymers, vol. 60, No. 3, 2001, pp. 229-245, XP002505419 us *p. 229-p. 236*.

(Continued)

*Primary Examiner* — Rebecca L Anderson
*Assistant Examiner* — Matthew P Coughlin
(74) *Attorney, Agent, or Firm* — Reinhart Boerner Van Deuren s.c.

(57) ABSTRACT

The present invention is directed to compounds of the formula (I) and (II) or salts thereof or N-oxides and their use in peptide synthesis.

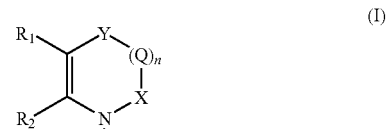

(I)

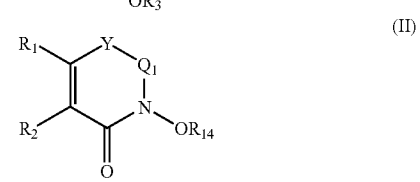

(II)

19 Claims, No Drawings

OTHER PUBLICATIONS

L. Carpino et al.: "3-hydroxy-4-oxo-3, 4-dihydro-5-azabenzo-1,2,3-triazine." Journal of Organic Chemistry., vol. 69, No. 1, 2004, pp. 54-61, XP002505420 USAmerican Chemical Society. Easton. *p. 54-p. 56*.

* cited by examiner

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: synthesized peptide Gly at amino and protected
      by CBZ; methyl ester of Gly at carboxy end

<400> SEQUENCE: 1

Gly Gly Val Ala Gly Gly
1               5

<210> SEQ ID NO 2
<211> LENGTH: 9
<212> TYPE: PRT
<213> ORGANISM: Artificial Sequence
<220> FEATURE:
<223> OTHER INFORMATION: synthesized peptide; amide of Gly at carboxy
      end

<400> SEQUENCE: 2

Val Gln Ala Ala Asp Tyr Ile Asn Gly
1               5

<210> SEQ ID NO 3
<211> LENGTH: 5
<212> TYPE: PRT
<213> ORGANISM: Artificial Sequence
<220> FEATURE:
<223> OTHER INFORMATION: synthesized peptide, Xaa in both cases is Aib;
      amide of Leu at carboxy end
<220> FEATURE:
```

```
-continued

<221> NAME/KEY: misc_feature
<222> LOCATION: (2)..(3)
<223> OTHER INFORMATION: Xaa can be any naturally occurring amino acid

<400> SEQUENCE: 3

Tyr Xaa Xaa Phe Leu
1               5

<210> SEQ ID NO 4
<211> LENGTH: 6
<212> TYPE: PRT
<213> ORGANISM: Artificial Sequence
<220> FEATURE:
<223> OTHER INFORMATION: synthesized peptide, Gly at amino end protected
      by CBZ; Gly at carboxy end is attached to solid resin

<400> SEQUENCE: 4

Gly Gly Val Ala Gly Gly
1               5
```

COUPLING AGENTS FOR PEPTIDE SYNTHESIS

This application claims priority benefit from International application no. PCT/US2004/036428, filed Nov. 1, 2004, and prior provisional patent application No. 60/516,167, filed Oct. 31, 2003, each of which is incorporated herein by reference in its entirety.

GOVERNMENT SUPPORT

This work has been supported by a grant form the National Institutes of Health GM-09706 and the National Science Foundation (CHE-9003192). The Government has certain rights in the invention.

BACKGROUND OF THE INVENTION

1. Field of the Invention

The present invention relates to a new process for effecting the acylation step in amide formation, especially in peptide synthesis.

2. Description of the Prior Art

Polypeptides, especially proteins, play a critical role in fundamental biochemical processes in living cells. Biochemical reactions, including metabolic reactions, are catalyzed by enzymes, which are comprised of proteins. These proteins are chiral molecules, and it is often the case that of the various stereoisomers that may possibly exist, one is usually the most efficacious.

Moreover, polypeptides are useful as medicaments. In recent years, peptides have been found useful in combating various diseases, including cancer, diabetes, plant toxins, and the like. Additionally, peptides have shown specific activity as growth promoters, suppressants, antibiotics, insecticides, contraceptives, anti-hypertensives, sleep inducers, anti-depressants, analgesics, and so on.

The synthesis of proteins has always been a challenge to chemists. However, chemical synthesis offers advantages not realized by genetic engineering and other biological approaches such as isolation of natural proteins. First, it is useful in confirming the structure of a protein. Moreover, protein synthesis is necessary to synthesize analogs, allowing scientists to evaluate biological activity and/or pharmacological efficacy in relation to molecular structure.

Success in the chemical synthesis of peptides relies, in part, on the use of the appropriate coupling reagents in combination with the appropriate protecting groups. Especially in peptide synthesis, formation of the peptide bond between two amino acids requires activation of the carboxyl group of one of the amino acids before the reaction can occur. However, the activation step in conjunction with the coupling reaction causes a serious problem of loss of configuration at the carboxyl residue which has been activated. Thus, in designing chemical syntheses of peptides, the objective is to provide the peptide product in good yield and maintenance of the configurational integrity of the carboxylic component, i.e., minimal racemization. Thus, the duality of good yield and minimal or no racemization is difficult to achieve because the best methods require the acid to be converted to a derivative bearing a good leaving group. Thus, under normal coupling conditions, there is a loss of configuration.

Moreover, current methods of syntheses also tend to produce side reactions which decrease yield.

Currently, syntheses of peptides are in solution by classical or various repetitive methods. Alternatively, peptides may be prepared on a solid support (Merrifield method). These are all popular techniques in synthesizing peptides from the coupling of two or more amino acids, in synthesizing larger peptides from the coupling of amino acids with smaller peptides or in the coupling of smaller peptides. Solution methods have the advantage of being easily monitored, allowing purification of intermediates, if necessary, at any stage. A major drawback, however, is the relative slow pace of synthesis, with each step being carried out manually.

The major advantage of the Merrifield method is its easy automation so that unattended, computer-controlled machine synthesis is possible. Unfortunately, the method suffers from an inherent deficiency due to the insoluble nature of the support on which the synthesis proceeds. Unless each acylation step occurs with approximately 100% efficiency, mixtures will inevitably be built up on the polymer. The longer the chain, the greater will be the contamination by undesired side reactions. Side products produced in such reactions remain to contaminate the desired product when it is removed from the polymeric matrix at the end of the cycle. These current techniques are not useful in preparing peptides of greater than 40-50 residues; separation of side products from the desired product becomes increasingly difficult when larger peptides are synthesized.

For very long segments (50 or more amino acids), therefore, current methods are not satisfactory. Often, mixtures are obtained of such forbidding complexity that it may be difficult or impossible to isolate the desired peptide.

The problems enumerated hereinabove may be eliminated if the proper derivatives of the underlying amino acids and/or the proper conditions for the coupling reaction could be found. Protecting groups, such as t-butyloxycarbonyl (t-Boc) or N-α-(9-fluorenylmethyl)oxycarbonyl (Fmoc), have been used to minimize side reactions.

The most commonly used coupling reagents are carbodiimides such as dicyclohexylcarbodiimides, diisopropylcarbodiimides, 1-ethyl-3-(3'-dimethylaminopropyl)carbodiimides used with various additives.

Additives generally inhibit side reactions and reduce racemization. Heretofore, the most common peptide coupling additive used during peptide coupling for peptide synthesis is 1-hydroxybenzotriazole (HOBt). This reagent has been used either in combination with a carbodiimide or other coupling agent or built into a stand alone reagent, such as 1-benzotriazolyoxytris (dimethylamino)phosphonium hexafluorophosphate (BOP) or an analogous uronium salt. HOBt is applicable to both stepwise and segment condensations. However, many cases have been encountered in which HOBt is ineffective, possibly because of steric effects, or low basicity of the amino component. Especially problematic are segment couplings at amino acid units other than glycine or proline, since the problem of racemization may be severe. The related N-hydroxybenzotriazinone (HOOBt) may provide better protection against racemization, but it is rarely used due to competing side reactions involving ring openings. A drawback in the use of BOP is that it produces a toxic side product, hexamethylphosphorotriamide.

Recently other coupling reagents have been introduced, such as N-[1H-benzotriazo-1-yl)(dimethylamino)methylene]-N-methylmethanaminiumhexafluorophosphate N-oxide (HBTU), N-[(1-H-benzotriazol)dimethylamino)methylene]N-methylmethanaminium tetrafluoroborate N-oxide (TBTU), O-(benzotriazol-1-yl)-1,3-dimethyl-1,3-dimethylene uranium hexafluorophosphate (HBMDU), O-(benzotriazol-1-yl)-1,1,3,3-bis(tetramethylene)uronium hexafluorophosphate (HBPyU) and O-(benzotriazol-1-yl)-1,1,3,3-bis(pentamethylene)uronium hexafluorophosphate (HBPipU).

Another additive that has been used in peptide synthesis is 3-hydroxy-4-oxo-3,4-dihydro-1,2,3-benzotriazine (HODhbt). HODhbt has proved to be generally superior to HOBt. Moreover, its use permits one to follow the completion of the reaction visually by a color change which occurs when acylation is complete. However, HODhbt has problems associated therewith due to inherent side reactions.

Other derivatives, which include O-(3,4-dihydro-4-oxo-1,2,3-benzotriazin-3-yl)-1,1,3,3-tetramethyluronium hexafluorophosphate, O-(3,4-dihydro-4-oxo-1,2,3-benzotriazin-3-yl)-1,1,3,1-tetra-methyluronium tetrafluoroborate and [3,4-dihydro-4-oxo-1,2,3-benzotriazin-3-yl)oxy]tris (pyrrolidino)phosphonium hexafluorophosphate also have applications in peptide coupling.

Other reagents for facilitating peptide coupling have also been described. For example, in *Tetrahedron Letters*, 1994, 2279-2282, Carpino, et al. disclose that 1-hydroxy-7-azabenzotriazole and its corresponding uronium and phosphonium salts, designated HAPyU and AOP, respectively, were effective in promoting peptide coupling and avoiding racemization in a model solid-phase peptide segment coupling process. In addition, Carpino, et al. disclose in *J. Org. Chem.*, 1994, 59, 695-698 that azabenzotriazolyluronium salts, e.g., designated as HBTU, HATU, HAPyU, and HAMDU, are useful in peptide synthesis.

U.S. Pat. No. 5,644,029 to Carpino discloses, among other things, the use of compounds of the following formula in promoting peptide coupling:

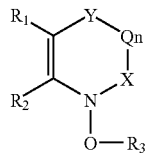

or N-oxides thereof or salts thereof wherein $R_1$ and $R_2$ taken together with the carbon atoms to which they are attached form a heteroaryl ring wherein said heteroaryl ring is an oxygen, sulfur or nitrogen containing heteroaromatic containing from 3 and up to a total of 13 ring carbon atoms, said heteroaryl may be unsubstituted or substituted with lower alkyl or an electron-donating group;

Y is O, $NR_4$, $CR_4R_5$;

$R_5$ is independently hydrogen or lower alkyl;

X is $CR_6R_7$ or $NR_6$;

$R_6$ and $R_7$ are independently hydrogen or lower alkyl; or $R_6$ and $R_7$ taken together form an oxo group or when n=0, $R_4$ and $R_6$ taken together may form a bond between the nitrogen or carbon atom of Y and the nitrogen or carbon atom of X;

Q is $(CR_8R_9)$ or $(NR_8)$;

when n is 1, $R_4$ and $R_8$ taken together may form a bond between the ring carbon or nitrogen atom of Q and the ring carbon or nitrogen atom of $R_8$;

n is 0 or 1;

$R_3$ is hydrogen, lower alkyl carbonyl, aryl carbonyl, lower aryl alkyl carbonyl,

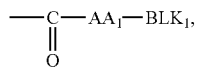

a positively charged electron withdrawing group, $SO_2R_{14}$, or

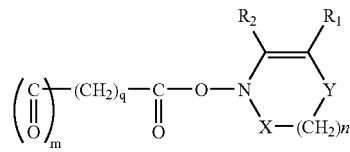

$R_{14}$ is lower alkyl, aryl or lower arylalkyl; q is 0-3;

$R_8$ and $R_9$ are independently hydrogen or lower alkyl or $R_7$ and $R_8$ taken together with the carbon to which they are attached form an aryl ring, $AA_1$ is an amino acid and BLK is an amino protecting group, and m is 0 or 1.

The present inventor has found other coupling agents, which provide relatively pure products with little, if any, side products being co-produced and minimal, if any, racemization. Moreover, the reaction conditions are very mild and the reagents used are easy to prepare. Thus, by using the compounds of the present invention as additives, the yield of the peptide s enhanced and little, if any, racemization occurs.

SUMMARY OF THE INVENTION

The present invention relates to a compound of Formula I and the use thereof in the preparation of a peptide bond in peptide synthesis, said compound having the formula:

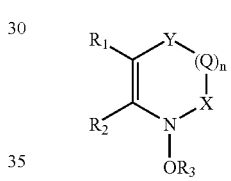

I or N-oxide thereof or salts of said compounds of Formula I wherein $R_1$ and $R_2$ taken together with the carbon atom to which they are attached form an aryl or a heteroaryl ring, wherein said aryl ring is an aromatic ring containing 6-14 ring carbon atoms and heteroaryl ring is an oxygen, sulfur, or nitrogen containing heteroaromatic containing at least 1 and up to 4 ring heteroatoms selected form oxygen, nitrogen and sulfur and containing from 3 and up to a total of 13 ring carbon atoms, said aryl and heteroaryl may each independently be unsubstituted or substituted with lower alkyl or electron donating group or electron withdrawing group;

Q is $CR_8R_9$ or $NR_8$;

Y is O, $NR_4$ or $CR_4R_5$;

X is $CR_6R_7$ or $NR_6$;

$R_5$ is hydrogen or lower alkyl;

$R_4$ is hydrogen or lower alkyl or $R_4$ and $R_6$ may form a bond between X and Y, when Y is $NR_4$ or $CR_4R_5$ and when Q is not present, or $R_4$ and $R_8$ may form a bond between Y and Q when Y is $NR_4$ or $CR_4R_5$ and Q is present, or $R_6$ and $R_8$ may form a bond between Q and X when Q is present;

$R_8$ and $R_9$ are independently hydrogen or lower alkyl, or when Q is present, $R_8$ taken together with $R_4$ may form a bond between Q and Y, when Y is $NR_4$ or $CR_4R_5$ or when Q is present, $R_8$ and $R_6$ may form a bond between Q and X;

$R_6$ and $R_7$ are independently hydrogen or lower alkyl or $R_6$ and $R_7$ taken together form an oxo; or $R_6$, taken together with $R_4$, may form a bond between Y and X when Q is not present and Y is $NR_4$ or $CR_4R_5$ or $R_6$ and $R_8$ taken together may form a bond between Q and X when Q is present; but in no circumstances is there a double bond between X and Q and Q and Y at the same time;

n is O or 1;

$R_3$ is

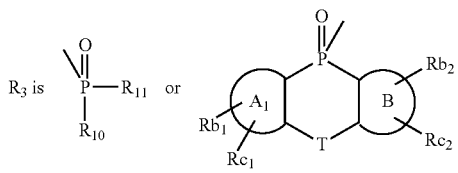

$R_{10}$ is $OR_{12}$, lower alkyl, aryl, aryl lower alkyl, lower cycloalkyl, lower cycloalkyl lower alkyl, heterocyclic, heterocyclic lower alkyl, cycloalkenyl, or cycloalkenyl lower alkyl;

$R_{11}$ is $OR_{13}$, lower alkyl, aryl, aryl lower alkyl, lower cycloalkyl, lower cycloalkyl lower alkyl, heterocyclic or heterocyclic lower alkyl cycloalkenyl or cycloalkenyl lower alkyl or $R_{10}$ and $R_{11}$ may be connected by a bridging group consisting of S, O, $NR_{30}$ or $(CHR_{30})_m$, wherein $R_{30}$ is lower alkyl or H and m is 1-3 such that $R_{10}$ and $R_{11}$ taken together with the phosphorous atoms form a 5 or 6 membered ring;

$R_{12}$ and $R_{13}$ are independently lower alkyl, aryl, aryl lower alkyl, lower cycloalkyl, lower cycloalkyl lower alkyl, heterocyclic, heterocyclic lower alkyl, cycloalkenyl, or cycloalkenyl lower alkyl;

Rings $A_1$ and B are independently aromatic rings containing 6 to 14 ring carbon atoms or cycloalkenyl or cycloalkyl each containing 5 to 14 ring carbon atoms;

T is $CHR_{31}$, O, S, or, $NR_{31}$;

$R_{31}$ is lower alkyl or H; and $Rb_1$, $Rb_2$, $Rc_1$ and $Rc_2$ are independently hydrogen, lower alkyl or an electron donating group.

In another embodiment, the present invention is directed to a compound of formula II or to a salt, in which the cationic portion has the structure of Formula II and to the use of the compound or salt:

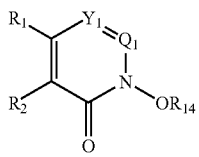

II or N-oxides thereof or salts of said compound of Formula II wherein $R_1$ and $R_2$ taken together with the carbon atom to which they are attached form a heteroaryl ring, wherein said heteroaryl is an heteroaromatic containing at least 1 and up to 4 ring heteroatoms selected from O, S and N and containing from 3 and up to a total of 13 ring carbon atoms, said heteroaryl may be unsubstituted or substituted with lower alkyl or electron donating group or electron withdrawing group;

$Y_1$ is N or $CR_{15}$;

$R_{15}$ is H or lower alkyl;

$Q_1$ is N or $CR_{16}$;

$R_{16}$ is H or lower alkyl; and $R_{14}$ is hydrogen, a positively charged electron withdrawing group, $SO_2R_{17}$, lower alkyl carbonyl, aryl carbonyl, lower arylalkyl carbonyl, $BLK_1 AA_1$,

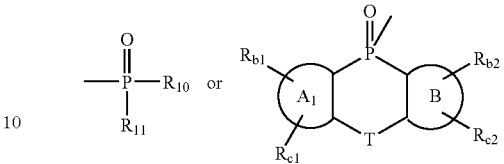

$R_{10}$ is $OR_{12}$, lower alkyl, aryl, aryl lower alkyl, lower cycloalkyl, lower cycloalkyl lower alkyl, heterocyclic, heterocyclic lower alkyl, cycloalkenyl or cycloalkenyl lower alkyl;

$R_{11}$ is $OR_{13}$, lower alkyl, aryl, aryl lower alkyl, lower cycloalkyl, lower cycloalkyl lower alkyl, heterocyclic, heterocyclic lower alkyl, cycloalkenyl or cycloalkenyl lower alkyl; or $R_{10}$ and $R_{11}$ may optionally be connected by a bridging group $T_1$ consisting of O, $NR_{30}$ or $(CHR_{30})_m$ wherein $R_{30}$ is lower alkyl or H and m is 1-3;

$R_{12}$ and $R_{13}$ are independently lower alkyl, aryl, aryl lower alkyl, lower cycloalkyl, lower cycloalkyl lower alkyl, heterocyclic, heterocyclic lower alkyl, lower cycloalkenyl or cycloalkenyl lower alkyl;

rings $A_1$ and B are independently aromatic rings containing 6 to 14 ring carbon atoms or cycloalkenyl or cycloalkyl, each containing 5 to 14 ring carbon atoms;

T is O, S, $NR_{31}$ or $CHR_{31}$;

$R_{31}$ is H or lower alkyl; and $Rb_1$, $Rc_1$, $Rb_2$ and $Rc_2$ are independently hydrogen, lower alkyl or electron donating group;

$R_{17}$ is aryl, lower alkyl or lower arylalkyl, $AA_1$ is an amino acid or peptide less a hydrogen atom on the N-terminus and an OH group on the C-terminus, and $BLK_1$ is an amino protecting group. In addition, the present invention is directed to the use of the compounds of Formula II or, when $R_{14}$ is a positively charged electron withdrawing group, its salt in which the cationic position has the structure of Formula II, in the preparation of peptide.

An additional embodiment of the present invention is directed to a process for preparing a peptide bond from the reaction between an amino compound and an acylating derivative of a carboxylic acid, said amino compound being an amino acid or peptide and said carboxylic acid being an N-terminal amino protected amino acid or an N-terminal amino protected peptide, which comprises reacting said amino compound and said acylating derivative of a carboxylic acid in the presence of an effective amount of a compound of formula I or formula II or to a salt, the cationic portion of which has the structure of Formula II, under conditions effective to form a peptide bond.

In another embodiment, the present invention is directed to a process for forming an amide from the reaction of an organic amine having a free amino and an acylating derivative of a carboxylic acid, which comprises reacting said amine with the acylating derivative of the carboxylic acid with an effective amount of a compound of Formula I or II or, when $R_{14}$ is a positively charged electron withdrawing group, a salt, in which the cation has the structure of Formula II under amide forming conditions.

An additional embodiment of the present invention is directed to the process for synthesizing peptides comprising (a) reacting a first Nα-amino protected amino acid with a peptide synthesis resin under conditions effective to covalently link the amino acid to the resin, (b) cleaving the protecting group from the amino acid to form an amine with a free amino group, (c) reacting said amine with a second N α-amino protected amino acid in the presence of a peptide forming effective amount of a compound of Formula I or II or when $R_{14}$ us a positively charged electron withdrawing group, to a salt in which the cation has the structure of Formula II, said reaction being effected under peptide-forming conditions, (d) repeating steps (b) and (c) until the desired peptide is obtained and (e) removing the peptide from the resin.

DETAILED DESCRIPTION OF THE PRESENT INVENTION

As used herein, the term "salt of Formula II" or any reference to a salt of Formula II refers to a salt of Formula II which consists of an anion and cation, the cation portion of which is positively charged. The positive charge may result from protonation, such as in the presence of an acid of the compound or Formula II or it may result from $R_{14}$ being a positively charged electron withdrawing group. If reference is to be made to a salt of Formula II in which the structure of Formula II contains a positively charged electron withdrawing group, the term "cation of Formula II" or its equivalent will be used.

As described hereinabove, an embodiment of the present invention relates to compounds of Formula I or Formula II or to salts thereof or N-oxide thereof or cation of Formula I and their use in peptide coupling. In other words, a first amino acid or a first peptide, each having a free amino group is coupled with an acylating derivative of either a second amino acid or a second peptide in the presence of compounds of Formula I or II or salts thereof or N-oxides thereof or cation of Formula II under amide forming conditions to form a peptide bond and thus form a larger peptide.

As employed herein, the term "heteroaryl" is a heteroaromatic containing at least one heteroatom ring atom selected from nitrogen, sulfur and oxygen and up to a maximum of four ring heteroatoms. The heteroaryl contains from 5 to 14 ring atoms and up to a total of 13 ring carbon atoms and a total of 18 carbon atoms. The heteroaryl group may be monocyclic, bicyclic or tricyclic, although it is preferred that the heteroaryl is bicyclic and especially monocyclic. Also included in this expression are the benzoheterocyclics. The heteroaryl group preferably contains no more than two ring heteroatoms, and most preferably contains one ring heteroatom. The most preferred ring heteroatoms are oxygen and nitrogen, with nitrogen being the most preferred.

If nitrogen is a ring atom, N-oxides can also be formed. The present invention contemplates the N-oxides of the nitrogen containing heteroaryls.

Examples of heteroaryls include thienyl, benzothienyl, 1-napthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, napthyridinyl, quinoxalinyl, quinazolinyl, cinnolinyl, pteridinyl, carbolinyl, isothiazolyl, isothiazolyl and the like. It is preferred that the heteroaryl group is pyridyl, pyrrolyl, furyl, indolyl, quinolyl, isoquinolyl or benzofuryl. Especially preferred is pyridyl.

When $R_1$ and $R_2$ taken together with the carbons to which they are attached form a tricyclic heteroaryl group, then the compounds of Formula I or II is tetracyclic; if a bicyclic heteroaryl group is formed from $R_1$ and $R_2$ taken together with the carbons to which they are attached, then the compounds of Formula I or II are tricyclic. Finally, if $R_1$ and $R_2$ taken together form a monocyclic heteroaryl group, then the compounds of Formula I or II are bicyclic. It is preferred that compounds of Formula I and II are tricyclic, and especially bicyclic.

The term "heterocyclic", as used herein, when used alone or in combination with other groups, refers to a heterocyclic ring containing at least one heteroatom ring atom selected form nitrogen, sulfur and oxygen up to a maximum of 4 ring heteroatoms and from 5 to 14 ring atoms and up to a total of 18 carbon atoms. The heterocyclic group may be monocyclic, bicyclic or tricyclic. It may be completely saturated or it may be partially unsaturated, i.e., it may contain one or more double bonds between ring atoms. It is preferred that the heterocyclic group contains 0, 1, 2, 3 or 4 double bonds. The term heterocyclic also includes heteroaryl, as defined herein. Moreover, it is preferred that the heterocyclic moiety contains no more than two ring heteroatoms and most preferably no more than one ring heteroatom. Examples include tetrahydrofuran, morpholinyl, piperazinyl, 2-tetrahydro quinolyl, 3-tetrahydroquinolyl, 6-tetrahydroquinolyl or 7-tetrahydroquinolyl and the like.

The term "lower alkyl", when used alone or in combination with other groups, refers to a carbon chain containing from one to six carbon atoms. It may be a straight chain or branched and includes such groups as methyl, ethyl, propyl, isopropyl, n-butyl, sec-butyl, isobutyl, t-butyl, n-pentyl, amyl, hexyl and the like. The preferred lower alkyl group contains from 1-3 carbon atoms, and is most preferably methyl.

The term "aryl" as used herein, alone or in combination, refers to an aromatic ring containing from 6-10 ring carbon atoms and up to a total of 15 carbon atoms. It includes such groups as phenyl, α-naphthyl, β-naphthyl and the like. The preferred aryl is phenyl. It excludes heteroaryls.

Aralkyl groups are aryl groups attached to the main chain through an alkylene bridge. Such groups include benzyl, phenethyl and the like.

"Lower alkyl carbonyl" refers to a lower alkyl group attached to the main chain through a carbonyl. Similarly, "aryl carbonyl" refers to an aryl group attached to the main chain through a carbonyl group.

"Lower cycloalkyl", as used herein refers to a cycloalkyl group containing 3-10 carbon ring atoms and up to a total of 15 carbon atoms. The cycloalkyl group may be monocyclic or bicyclic or tricyclic. Examples include cyclopropyl, cyclobutyl, cyclopentyl, cyclohexyl, cycloheptyl, cyclooctyl, norbornyl, adamanyl, decalinyl, and the like. The preferred lower cycloalkyl groups are cyclopentyl and cyclohexyl.

"Lower cycloalkyl lower alkyl" is a lower cycloalkyl group attached to the main chain through an alkylene bridge. Such groups include cyclohexylmethyl, cyclopentylethyl and the like.

"Cycloalkenyl" refers to a lower cycloalkyl group, as defined herein, containing at least one double bond and up to a maximum of 6 carbon-carbon double bonds. It is not completely aromatic; but it may include an aromatic moiety. It may contain one ring or two or more rings fused together. The double bonds may be located in one ring or both rings. One or more rings may be completely aromatic, while the remaining rings, if any, in the structure may each be completely saturated or contain 1 or 2 double bonds. It is to be noted however, that cycloalkenyl, as described herein, excludes aryl. Examples include cyclohexenyl, cyclooctenyl, 1-, 2-, 3-, 4-, 5-, 6-, 7- or 8-indanyl, and the like.

As used herein, an "electron donating group" shall designate a group that will release or donate electrons more than hydrogen would if it occupied the same position in the molecule. See., J. March, *Advanced Organic Chemistry*, $3^{rd}$ Ed., John Wiley & Sons p. 237 (1985). These types of groups are well known in the art. Examples include lower alkylamino, diloweralkylamino, amino, halo, aryl, lower alkoxy, lower aralkoxy, aryloxy, mercapto, lower alkylthio, and the like. The preferred electron donating groups are amino, hydroxy, lower alkoxy, lower alkylamino and diloweralkylamino.

The term "electron withdrawing groups" as defined herein refers to a group that will draw electrons to itself more than a hydrogen atom would if it occupied the same position in the molecule. See., J. March, *Advanced Organic Chemistry*, $3^{rd}$ Ed., John Wiley & Sons p. 237 (1985). They include such groups as nitro, monohaloalkyl, dihaloalkyl, trihaloalkyl (e.g., $CF_3$), halo, formyl, lower alkanoyl, lower alkylsulfonyl, lower alkylsulfinyl, carboxy, lower alkoxy carbonyl, sulfonamido, amido, $CONR_{50}R_{51}$, wherein $R_{50}$, and $R_{51}$ are independently hydrogen lower alkyl, aryl, aryl lower alkyl, heterocyclic; heterocyclic lower alkyl, lower cycloalkyl, lower cycloalkyl lower cycloalkyl lower alkyl, cycloalkenyl cycloalkenyl lower alkyl and the like.

A "positively charged electron withdrawing group" is an electron withdrawing group bearing a positive charge and forming a stable bond to a N-hydroxide (N—O). These types of groups are well known in the art. Examples include uronium groups, e.g.,

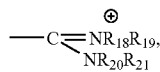

imino cations, e.g.,

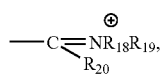

or phosphonium cations, e.g.,

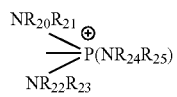

and the like, wherein $R_{18}$, $R_{19}$, $R_{20}$, $R_{21}$, $R_{22}$, $R_{23}$, $R_{24}$ and $R_{25}$ are independently hydrogen, lower alkyl, lower alkoxy lower alkyl or if the imino cation is formed, $R_{18}$ ad $R_{20}$ taken together with the nitrogen atoms to which they are attached and the carbon atom therebetween may form a ring containing up to 6 ring atoms and up to a total of 5 ring carbon atoms or $R_{18}$ and $R_{19}$ taken together with the nitrogen atom to which they are attached or $R_{20}$ and $R_{21}$ taken together with the carbon atoms to which they are attached may form a 5 or 6-membered heterocyclic ring containing up to a total of 5 ring carbon atoms or if the uronium cation is formed, $R_{20}$ and $R_{18}$ may be taken with the nitrogen to which they are attached form a 5 or 6 membered heterocyclic ring containing up to a total of 5 ring carbon atoms or both $R_{18}$ and $R_{19}$ taken together with the nitrogen atoms to which they are attached or $R_{20}$ and $R_{21}$ taken together with the nitrogen atom to which they are attached, may each simultaneously form a 5 or 6-membered heterocyclic ring, each ring containing up to a total of 5 ring carbon atoms. In the uronium and imino cations, it is preferred that $R_{18}$ and $R_{19}$ and $R_{20}$ and $R_{21}$, when present, are the same. It is especially preferred that $R_{18}$, $R_{19}$, $R_{20}$, $R_{21}$, whenever present, are the same. It is also more preferred that the rings formed with respect to the uronium, imino, and phosphonium cations are 5 or 6 membered rings.

With respect to the phosphonium cation, $R_{18}$ and $R_{19}$ and/or $R_{20}$ and $R_{21}$ and/or $R_{22}$ and $R_{23}$ may, each be independently taken together with the nitrogen atoms to which they are attached to form a ring. Thus, the phosphonium cation may be comprised of 1 ring, two rings or three rings. It is preferred that $R_{18}$ and $R_{19}$, or $R_{20}$ and $R_{21}$ or $R_{22}$ and $R_{23}$ are the same. It is especially preferred that $R_{18}$, $R_{19}$, $R_{20}$, $R_{21}$, $R_{22}$ and $R_{23}$ are the same.

With respect to cations of Formula II, preferred cyclic uronium and imino groups have the formula

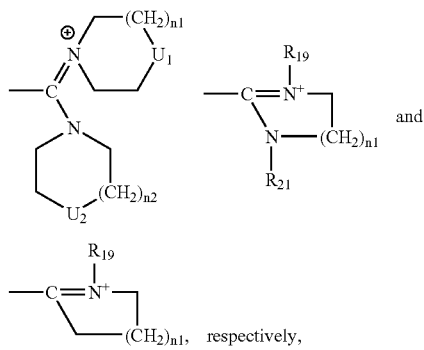

wherein $R_{19}$ and $R_{20}$ are as defined hereinabove and $n_1$ and $n_2$ are independently 0 or 1, and $U_1$ and $U_2$ are independently O, $CH_2$ or NH or N-Alk wherein Alk is lower alkyl.

In the above formulae, the preferred values of $R_{18}$, $R_{19}$, $R_{20}$ $R_{21}$, $R_{22}$ and $R_{23}$ are independently methyl, ethyl, n-butyl, pentyl and $CH_2CH_2$—O—$CH_2CH_3$. It is preferred that $R_{18}$, $R_{19}$, $R_{20}$ (for all) and $R_{21}$, when present (for imino), and $R_{22}$ and $R_{23}$ (for phosphonium) when present, are the same.

The preferred values of $R_{18}$, $R_{19}$, $R_{20}$, $R_{21}$, when present, and $R_{22}$, and when present, and $R_{23}$, when present, are independently lower alkyl, especially methyl. It is preferred $R_{18}$, $R_{19}$, $R_{20}$ and $R_{21}$, when present, $R_{22}$, when present, and $R_{23}$, when present, are all the same. Further it is preferred that all are methyl.

With respect to the uronium and/or imino cations, when $R_{18}$ and $R_{19}$ or $R_{20}$ and $R_{21}$ taken together form a ring, they may form heterocyclic moieties of the formula:

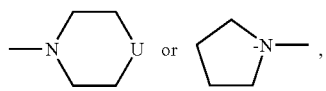

wherein

U=$CH_2$, O, NH or N-Alk, wherein Alk is lower alkyl, especially methyl.

Preferred cyclic groups present in the phosphonium cations also have the formula

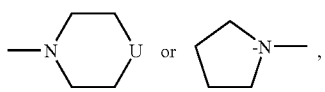

wherein U, is defined hereinabove.

It is preferred that $R_1$ and $R_2$ taken together with the carbon atoms to which they are attached form an aryl or heteroaryl ring wherein the aryl ring is a phenyl or naphthyl and the heteroaryl ring contains 5 to 10 ring atoms and one or two ring heteroatoms consisting of O, S, N and 3-8 ring carbon atoms.

With respect to compounds of Formula I, the following are preferred. When n is 1, it is preferred that $R_7$ and $R_8$ are hydrogen or lower alkyl, but most preferably hydrogen.

Preferred values of Y are S, O, $NR_4$, or $CR_4R_5$, wherein $R_4$ and $R_5$ are independently hydrogen or methyl. Especially preferred values of Y are O, $CH_2$ and NH. It is also preferred, however, that Q is absent and Y forms a double bond with X.

It is preferred that X is $CR_6R_7$ or $NR_6$. Preferred values of $R_6$ and $R_7$ are hydrogen or lower alkyl.

With respect to compounds of Formula I, it is preferred that Q is not present and Y and X are independently N or CH. It is more preferred that at least one of Y and X is N and the other is CH. It is even more preferred that Y is N and X is CH or N or that Y and X are both N.

When $R_6$ and $R_7$ taken together form an oxo group, X becomes C=O. It is most preferred that X is C=O, $CH_2$ or NH or $N(CH_3)$. Moreover, an embodiment of Formula I has the formula

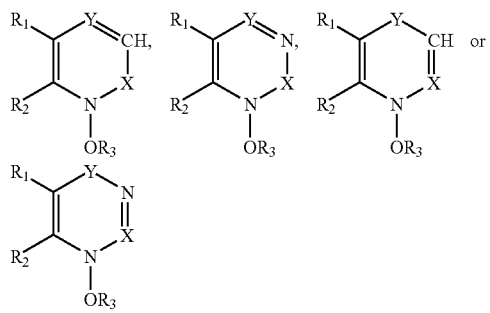

In cases when n is 0, then $R_4$ and $R_6$ taken together may form a bond between X and Y, i.e., a bond may form between the ring carbon atom of X and the ring carbon atom of Y, or between the ring nitrogen atom of X and the ring nitrogen atom of Y, or the ring nitrogen atom of X, and the ring carbon atom of Y or the ring carbon atom of X and the ring nitrogen atom of Y. In other words, under these circumstances when n is O and $R_4$ and $R_6$ taken together form a bond between X and Y, the compound of Formula I becomes

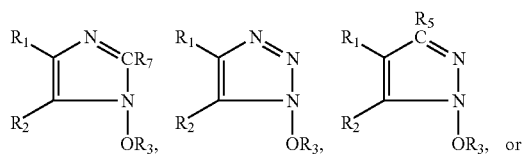

-continued

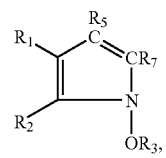

wherein $R_1$, $R_2$, Y, X, and $R_3$ are as defined above. Under these circumstances, it is preferred that Y is CH or N and X is CH or N. It is most preferred that Y and X are N.

When n is 1, the compound of Formula I becomes

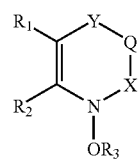

wherein
$R_1$, $R_2$, Q, $R_8$, $R_9$, Y, $R_4$, $R_5$, X, $R_6$, $R_7$ and $R_3$, $R_{10}$, $R_{11}$, $R_{12}$ and $R_{13}$ are as defined above. It is preferred that $R_8$ and $R_9$ are hydrogen.

As indicated hereinabove, when n is 1, $R_4$ and $R_8$ taken together may form a bond between Q and Y, i.e., the ring carbon atom of $R_4$ and the ring carbon atom of $R_8$ may form a bond, or the ring carbon atom of $R_4$ and the ring nitrogen atom of $R_8$ may form a bond, or the ring nitrogen atom of $R_4$ and the ring carbon atom of $R_8$ may form a bond or the ring nitrogen atom of $R_4$ and the ring nitrogen atom of $R_8$ may form a bond. For example, under these circumstances, the compound of Formula I becomes:

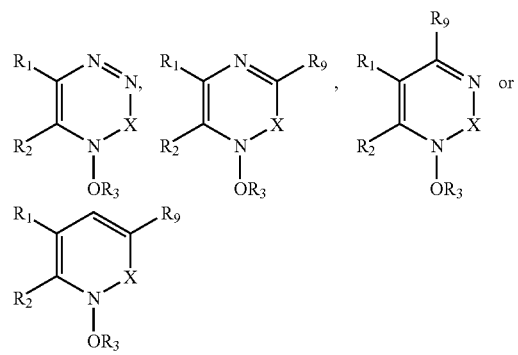

The preferred values of X in this formulations are C=O or NH or $CH_2$.

When n is 1, preferred values of Q are $CH_2$ or NH. However, it is also preferred that the compounds of Formula I have the formula:

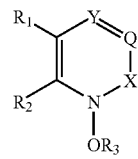

wherein
Q is $CR_9$ or N, and
$R_9$ is hydrogen or lower alkyl and $R_1$, $R_2$, X, $OR_3$ and Y are as defined hereinabove. Examples of compounds of Formula I include:

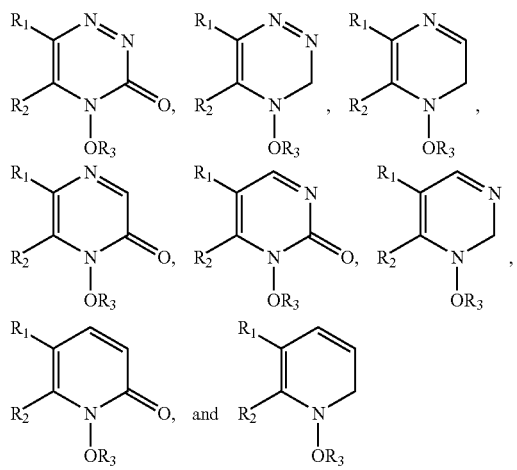

wherein $R_1$, $R_2$ and $R_3$ are as defined hereinabove.

It is also preferred that compounds of Formula I have the formula:

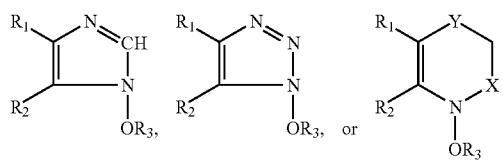

wherein $R_1$, $R_2$, $R_3$, Y and X are as defined hereinabove.

The most preferred compounds of Formula I have the formula:

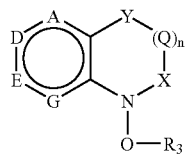

III or N-oxides thereof wherein Q, Y, X, $R_3$, n, are as defined hereinabove,
A is N or $CR_{24}$;
D is $CR_{25}$ or N;
E is $CR_{26}$ or N;
G is $CR_{27}$ or N; and
$R_{24}$, $R_{25}$, $R_{26}$ and $R_{27}$ are independently hydrogen or lower alkyl or an electron donating group or $R_{25}$ and $R_{26}$ or $R_{24}$ and $R_{25}$ or $R_{26}$ and $R_{27}$ taken together form with the carbon atom to which they are respectively attached an aryl ring. It is preferred that A, D, E or G all are CH and more preferably at least one of A, D, E, G is N.

It is preferred that no more than two of A, D, E, G are N. It is most preferred that only one of A, D, E, G is N. Further it is preferred that $R_{24}$, $R_{25}$, $R_{26}$ or $R_{27}$ are hydrogen or an electron-donating group, as defined herein, The preferred electron donating group is lower dialkylamino especially N,N-dimethyl amino and lower alkoxy, e.g. methoxy.

Preferred compounds of Formula III have the formulae:

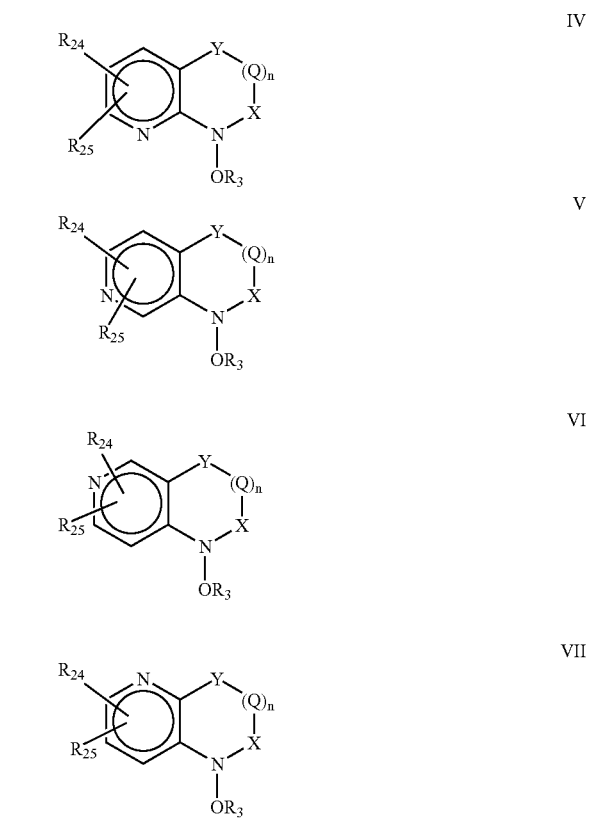

or N-oxides thereof wherein Y, X, n, Q and $R_3$ are as defined hereinabove and $R_{24}$ and $R_{25}$ are independently lower alkyl, hydrogen or an electron donating group.

Of the compounds of Formula IV-VII, when n is 1, the most preferred compound is that of Formula IVa

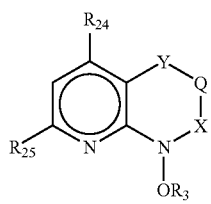

IVA or N-oxides thereof wherein Q, Y, X and $R_3$ are as defined hereinabove and $R_{24}$ and $R_{25}$ are lower alkyl or hydrogen or an electron donating group.

Preferred compounds of Formula I also have the formula

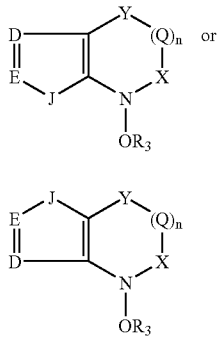

VIII or

IX or N-oxides thereof wherein n, Q, D, E, X and Y are as defined hereinabove and J is $NR_{28}$, O, $CR_{28}R_{29}$ or S(O)p, and p is 0, 1, 2.

$R_{28}$ is hydrogen, lower alkyl or electron donating group as defined hereinabove and $R_{29}$ is hydrogen or lower alkyl. It is preferred that $R_{29}$ is hydrogen. The preferred values of $R_{28}$ is an electron donating group or hydrogen.

Preferred values of J are O or S(O)p; the preferred value of p is 1.

Preferred compounds of Formula VIII when n is 1 have the formula:

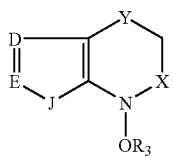

VIIIa or N-oxides thereof wherein J, Y, $R_8$, $R_9$, n and $R_3$ are as defined hereinabove and X is C=O.

In compounds VIII, IX, and VIIIa as depicted above, at least one of D, E, or J is a heteroatom. Furthermore, it is most preferred that at most two of J, E, and D are heteroatoms. It is most preferred that only one of J, E, and D is a heteroatom.

When n is O, preferred compounds of Formula I becomes:

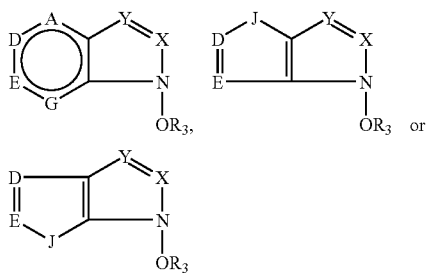

Thus, the present invention includes compounds having the formula:

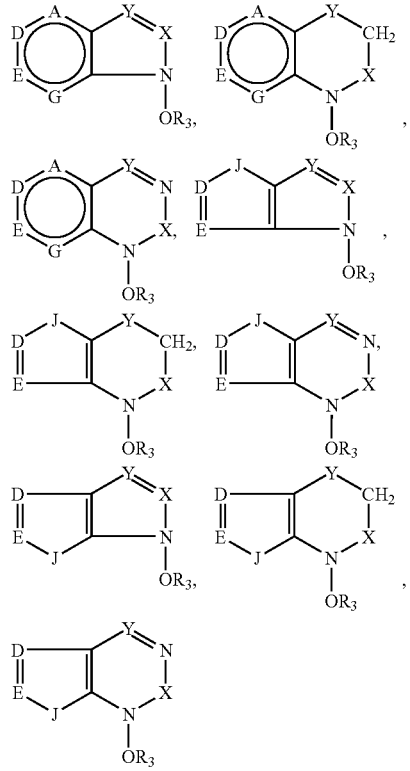

or N-oxides thereof.

wherein A, D, E, G, Y, X, $R_3$ and J are as defined hereinabove.

The compounds of Formula I more preferably are compounds of the formula:

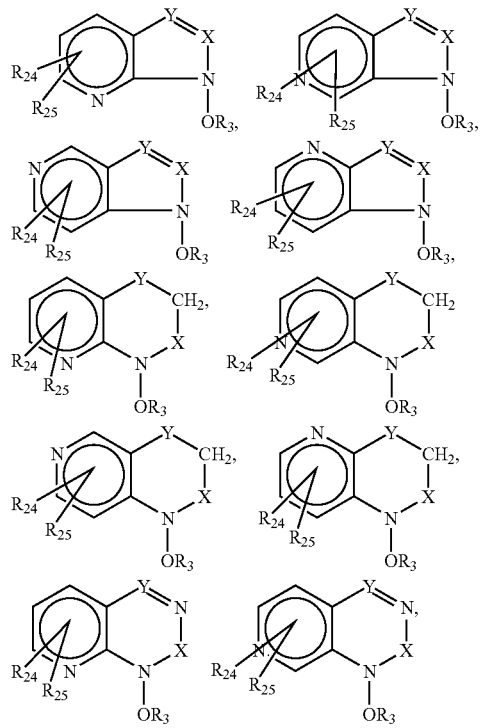

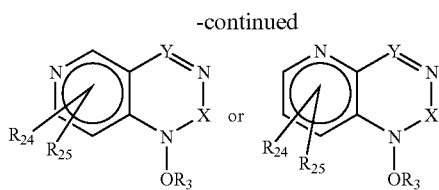

or N-oxides thereof.

In the above formulae, when the ring contains Y=X, this means that $R_4$ of Y and $R_6$ of X are joined together to form a ring bond between the Y ring atom and the X ring atom, so that as depicted hereinabove there is a double bond between the Y ring atom and the X ring atom.

Furthermore, in the above formulae, when the ring contains Y=N, then $R_4$ of Y and $R_8$ of $NR_8$ of Q join together to form a ring bond so that there is a double bond between the nitrogen ring atom and the Y atom. Thus, Y is $CR_5$ or N under these circumstances.

The most preferred embodiment of Formula I has the formula:

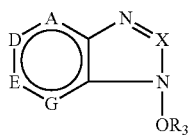

wherein one or two of A, D, E, G, is N and the rest are CH and X is CH or N. It is most preferred that X is N. It is also preferred that at most one of A, D, E and G is N and the rest are CH. It is most preferred that A is N and especially G is N.

Preferred embodiments of compounds of Formula I include:

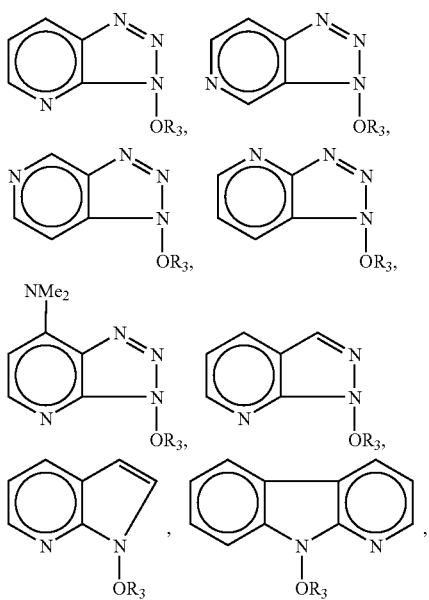

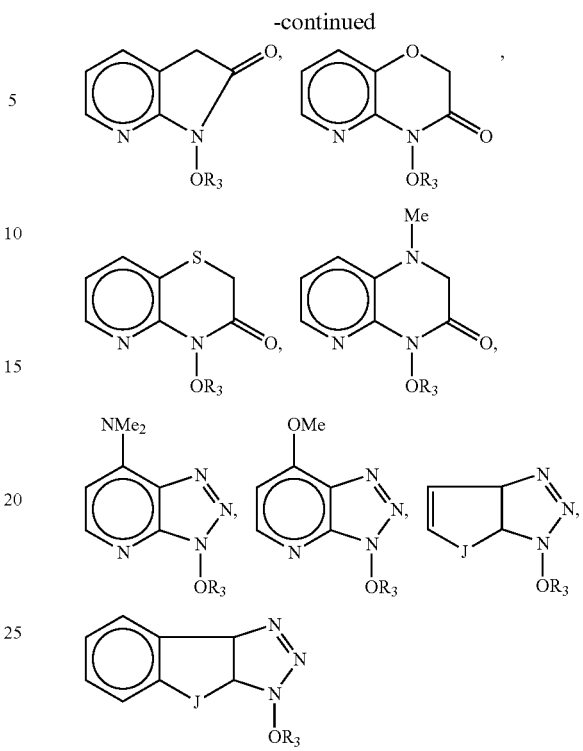

or the N-oxides thereof.

With respect to compounds of Formula I, $R_3$ is as defined hereinabove. The various groups on $R_{10}$, $R_{11}$, $R_{12}$ and $R_{13}$, e.g., alkyl, aryl, arylalkyl, cycloalkyl, cycloalkylalkyl, heterocyclic, heterocyclic lower alkyl or lower cycloalkyl heterocyclics may be unsubstituted, or substituted by lower alkyl or electron donating or electron withdrawing groups. It is preferred that the groups are unsubstituted or substituted by lower alkyl.

With respect to compounds of Formula I, it is preferred that $R_{10}$ is $OR_{12}$, lower alkyl, aryl or aryl lower alkyl. It is more preferred that $R_{10}$ is $OR_{12}$ or aryl.

It is also preferred that $R_{11}$ is $OR_{13}$, lower alkyl, aryl or aryl lower alkyl. It is most preferred that $R_{11}$ is $OR_{13}$ or aryl. Preferred values of $R_{12}$ and $R_{13}$ each independently are lower alkyl, aryl or aryl or aryl lower alkyl. It is most preferred that $R_{12}$ and $R_{13}$ are alkyl having 1-3 carbon atoms, or phenyl. It is also preferred that $R_{12}$ and $R_{13}$ are the same.

It is also preferred that $R_{10}$ and $R_{11}$ are connected to each other by a bridging group, $T_1$. Preferred values of $T_1$ are O, $CH_2$, S, or $NR_{30}$ when $R_{30}$ is lower alkyl and more preferably H. When $R_{10}$ and $R_{11}$ are joined together, then $R_3$ becomes

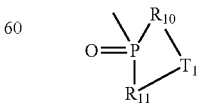

wherein $R_{10}$, $R_{11}$ and T, are as defined hereinabove. As defined herein $R_3$ may be defined as

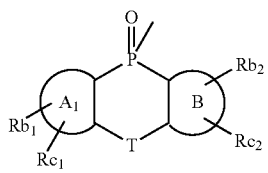

It is preferred that rings $A_1$ and B are independently aromatic, especially phenyl.

It is preferred that $R_3$ is

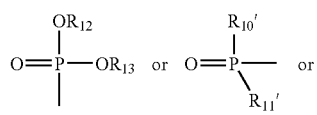

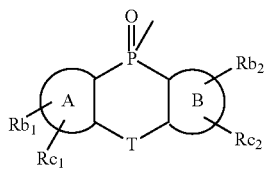

wherein $R_{10}'$ and $R_{11}'$, $R_{12}$ and $R_{13}$ are independently lower alkyl, aryl or aryl lower alkyl and $Rb_1$, $Rc_1$, $Rb_2$ and $Rc_2$ are independently hydrogen or lower alkyl. It is also preferred that $R_{12}$ and $R_{13}$ are connected by a bridging group $T_1$ to form the following $R_3$ moiety

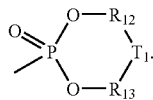

In an embodiment of the present invention, $R_{10}$ and $R_{11}$ are connected by the bridging group $T_1$, as depicted hereinabove. Preferred values of $T_1$ are $CH_2$, O, S and NH and most preferably $CH_2$ and O.

Embodiments of $R_3$ include

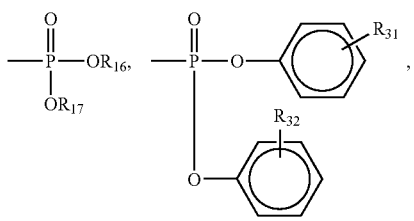

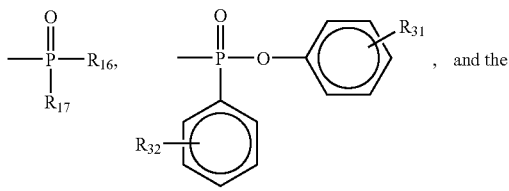

, and the

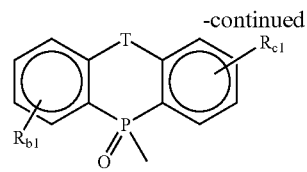

wherein $R_{16}$ and $R_{17}$ are independently lower alkyl, $R_{b1}$ and $R_{c1}$ are independently H or lower alkyl and T is as defined hereinabove and preferably O, NH or $CH_2$.

Examples of $R_3$ include

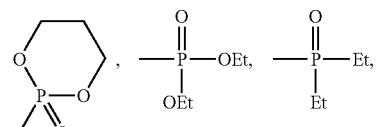

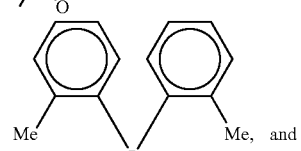

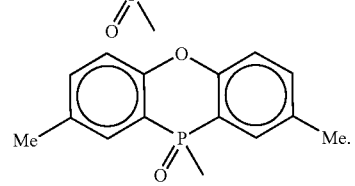

Of course, various combinations and permutations of the formulae described herein are also contemplated by the present invention. In addition, Markush groupings containing less than all of the elements described hereinabove as well as the various permutations thereof are also contemplated by the present invention.

The compounds of Formula I can be prepared by art recognized techniques. An illustrative technique is described hereinbelow.

For example, compounds of formula

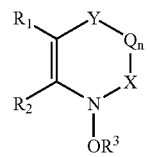

can be prepared by reacting

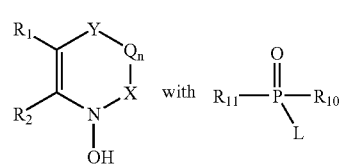

100 under substitution reaction conditions wherein $R_1$, $R_2$, Y, Q, n, $R_3$, $R_{10}$ and $R_{11}$ are as defined hereinabove and L is a leaving group, such as halo and the like.

It is preferable that the reaction is run in an inert polar organic solvent and that the reactants are soluble therein at room temperature. It is also preferred that the product of the substitution is insoluble in the solvent at room temperature. Examples of suitable solvents for the reaction include chloroform, carbon tetrachloride, ethyl ether, dioxane, tetrahydrofuran and methylene dichloride, and the like. The reaction takes place at effective temperatures, which may range from the melting point of the solvent to reflux temperature thereof but it is preferred that the reaction take place at about room temperature or at slightly elevated temperatures up to the reflux temperature of the solvent. It is especially preferred that the reaction take place at room temperature or at slightly elevated temperatures, such as up to 60° C.

Compounds of Formula 100 can be prepared as described in U.S. Pat. No. RE 37,686, RE 38,073, 5,580,981, 5,644,029, 5,698,675, the contents of which are incorporated by reference.

For example, compounds of Formula 100, such as

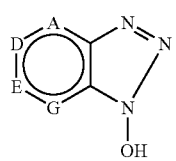
100(a)

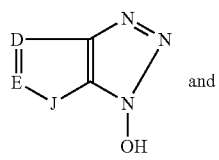
and
100(b)

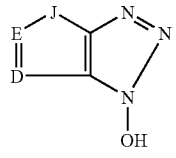
100(c)

can be prepared by reacting hydrazine with

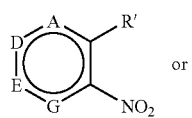
or
101(a)

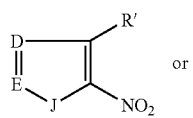
or
101(b)

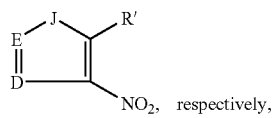
respectively,
101(c)

wherein R' is halogen, NH—$NH_2$ or OR", and

R" is lower alkyl, such as methyl. This reaction is performed at slightly elevated temperatures, such as 70-100° C., although the reaction may be performed at temperatures ranging from room temperature to the boiling point of the solvent.

The reaction is usually run in an organic solvent in which the reactants are insoluble at room temperature, but in which the reactants and product are soluble at slightly elevated temperatures. Examples of useful solvents include ethanol, DMF and the like. In many cases, there is a color change in the reaction mixture, indicating the formation of the product. Work-up, such as removal of the solvent, followed by acidification provides the desired product.

The hydrazino derivative (R'=NH—$NH_2$) can be prepared by reacting the corresponding halide, such as chloride or bromide, with hydrazine under substitution reaction conditions. The ether derivative ($R^1$=OR") can be prepare by reacting the corresponding alcohol with an alkylating reagent, such as $Me_2SO_4$/$Na_2CO_3$, under ether forming conditions.

Compounds of Formulae 100a, 100b, or 100c are useful for preparing compounds of Formula I. These latter compounds can also be prepared by art-recognized techniques. For example, compounds of Formula I are prepared by reacting compounds of 100a, 100b, 100c, respectively, with

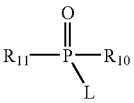

under substitution reaction conditions wherein $R_{10}$ and $R_{11}$ are defined hereinabove and L is a leaving group, such as halo, (e.g., Cl, Br, I) and the like.

The N-oxides can be prepared from the compounds of Formula I having a nitrogen ring heteroatom in the heteroaryl group. These N-oxides are prepared by art-recognized techniques such as by oxidation thereof, such as with peracid; e.g., peracetic acid or m-chloroperbenzoic acid.

With respect to compounds of Formula II, it is preferred that $Y_1$ is N or $CR_{15}$, wherein $R_{15}$ is hydrogen or methyl. Especially preferred values of $Y_1$ are CH and N.

It is also preferred that $Q_1$ is N or $CR_{16}$ wherein $R_{16}$ is hydrogen or lower alkyl. The preferred value of $Q_1$ is N or CH.

With respect to compounds of Formula II, preferred values of $Y_1$ and $Q_1$ are CH or N. In a preferred embodiment, the compound of Formula II has the formula

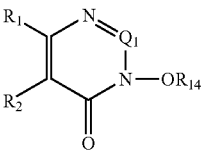

wherein $R_1$ and $R_2$ and $R_{14}$ are as defined as hereinabove and $Q_1$ is N or CH, but especially N.

Another embodiment of the compound having Formula II or salt of Formula II, wherein the cation has the formula is:

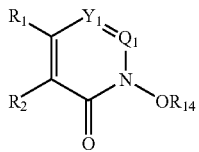

wherein $R_1$ and $R_2$ taken together with the carbon atoms to which they are attached form an heteroaryl ring wherein said heteroaryl ring is an oxygen, sulfur or nitrogen heteroaromatic containing from 3 to 13 ring carbon atoms and 1-4 heteroatoms selected from O, S and N, said heteroaryl ring may be unsubstituted or substituted with lower alkyl or electron donating group;

$Y_1$ is N or $CR_{15}$;

$R_{15}$ is H or lower alkyl;

$Q_1$ is N or $CR_{16}$;

$R_{16}$ is H or lower alkyl;

$R_{14}$ is hydrogen, a positively charged electron withdrawing group,

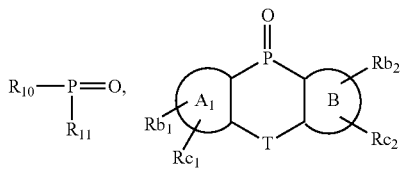

$SO_2R_{17}$, lower alkyl carbonyl, aryl carbonyl, lower alkyl aryl, or $BLK_1$-$AA_1$ $R_{17}$ is aryl, aryl lower alkyl or lower arylalkyl;

$AA_1$ is an amino acid or peptide less a hydrogen atom on the N-terminus and an OH on the C-terminal;

$BLK_1$ is an amino protecting group, $R_{10}$ is $OR_{12}$, lower alkyl, aryl, aryl lower alkyl, lower cycloalkyl, lower cycloalkyl lower alkyl, heterocyclic, heterocyclic lower alkyl, lower cycloalkenyl, lower cycloalkenyl or lower cycloalkenyl lower alkyl;

$R_{11}$ is $OR_{13}$, lower alkyl, aryl, aryl lower alkyl, lower cycloalkyl heterocyclic, heterocyclic lower alkyl, lower cycloalkenyl, lower cycloalkenyl lower alkyl;

and $R_{10}$ and $R_{11}$ may optionally be connected by a bridging group selected from the group consisting of O, S, $NR_{30}$, or $(CHR_{30})_m$, wherein each $R_{30}$ is independently lower alkyl or hydrogen and m is 1-3;

$R_{12}$ and $R_{13}$ are independently lower alkyl, lower cycloalkyl, lower cycloalkyl lower alkyl, heterocyclic, heterocyclic lower alkyl, lower cycloalkenyl, or lower cycloalkenyl lower alkyl;

ring $A_1$ and ring B are independently aromatic containing 6 to 14 ring carbon atoms or cycloalkenyl or cycloalkyl, each containing 5 to 14 ring carbon atoms;

$R_{b1}$, $R_{c1}$, $R_{b2}$, $R_{c2}$ are independently hydrogen, lower alkyl or electron donating group;

T is $CHR_{31}$, O, S or $NR_{30}$; and $R_{31}$ is hydrogen or lower alkyl.

Another embodiment of the compound having Formula II or salt of Formula II, wherein the cation has the formula is:

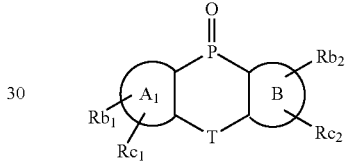

or N-oxide or salt thereof wherein one of $Y_1$ and $Q_1$ is $CR_{15}$ and the other is N or CH;

$R_{15}$ is H or lower alkyl;

$R_1$ and $R_2$ taken together with the carbon atom to which they are attached form an aryl or heteroaryl ring wherein said aryl ring is an aromatic ring containing 6-14 ring carbon atoms and said heteroaryl ring is an oxygen, sulfur or nitrogen heteroaromatic containing from 3 to 13 ring carbon atoms and 1-4 heteroatoms selected from O, S and N, said heteroaryl ring may be unsubstituted or substituted with lower alkyl or electron donating group;

$R_{14}$ is hydrogen, a positively charged electron withdrawing group, $SO_2R_{17}$, lower alkyl carbonyl, aryl carbonyl, lower alkyl aryl, or $BLK_1$-$AA_1$ $R_{17}$ is aryl, aryl lower alkyl or lower arylalkyl;

$R_{11}$ is $OR_{13}$, lower alkyl, aryl, aryl lower alkyl, lower cycloalkyl heterocyclic, heterocyclic lower alkyl, lower cycloalkenyl, lower cycloalkenyl lower alkyl;

$R_{10}$ is $OR_{12}$, lower alkyl, aryl, aryl lower alkyl, lower cycloalkyl, lower cycloalkyl lower alkyl, heterocyclic, heterocyclic lower alkyl, lower cycloalkenyl, lower cycloalkenyl or lower cycloalkenyl lower alkyl;

and $R_{10}$ and $R_{11}$ may optionally be connected by a bridging group selected from the group consisting of O, S, $NR_{30}$, or $(CHR_{30})_m$, wherein each $R_{30}$ is independently lower alkyl or hydrogen and m is 1-3;

$AA_1$ is an amino acid or peptide less a hydrogen atom on the N-terminus and an OH on the C-terminal;

$BLK_1$ is an amino protecting group, $R_{12}$ and $R_{13}$ are independently lower alkyl, lower cycloalkyl, lower cycloalkyl lower alkyl, heterocyclic, heterocyclic lower alkyl, lower cycloalkenyl, or lower cycloalkenyl lower alkyl;

ring $A_1$ and ring B are independently aromatic containing 6 to 14 ring carbon atoms or cycloalkenyl or cycloalkyl, each containing 5 to 14 ring carbon atoms;

$R_{b1}$, $R_{c1}$, $R_{b2}$, $R_{c2}$ are independently hydrogen, lower alkyl or electron donating group;

T is $CHR_{31}$, O, S or $NR_{31}$; and $R_{31}$ is hydrogen or lower alkyl.

As defined herein, in some embodiments of Formula II, $R_1$ and $R_2$ taken together with the carbon atoms to which they are attached form an aryl ring. It is preferred that the aryl ring is naphthyl and is especially phenyl.

Moreover, in Formula II, as defined herein $R_{14}$ is preferably H or a positively charged electron withdrawing group, as defined hereinabove, or

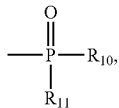

wherein $R_{10}$ and $R_{11}$ are as defined herein and the electron withdrawing group is as defined hereinabove. It is most preferred that $R_{14}$ is

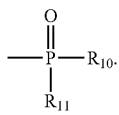

The preferred values of $R_{10}$ and $R_{11}$ are as defined hereinabove with respect to Formula I.

Preferred structures of Formula II have the formula:

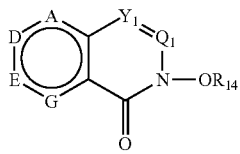

wherein
$Y_1$ is N or $CR_{15}$;
$R_{15}$ is H or lower alkyl;
$Q_1$ is N or $CR_{16}$;
$R_{14}$ is hydrogen, a positively charged electron withdrawing group,
$R_{16}$ is H or lower alkyl;

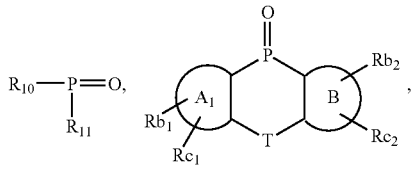

$SO_2R_{17}$, lower alkyl carbonyl, aryl carbonyl, lower alkyl aryl or $BLK_1$-$AA_1$; $AA_1$ is an amino acid or peptide less a hydrogen atom on the N-terminus and an OH on the C-terminus;
$BLK_1$ is an amino protecting group;
$R_{10}$ is $OR_{12}$, lower alkyl, aryl, aryl lower alkyl, lower cycloalkyl, lower cycloalkyl lower alkyl, heterocyclic, heterocyclic lower alkyl, lower cycloalkenyl, or lower cycloalkenyl lower alkyl;
$R_{11}$ is $OR_{13}$, lower alkyl, aryl, aryl lower alkyl, lower cycloalkyl, lower cycloalkyl lower alkyl, heterocyclic, heterocyclic lower alkyl, lower cycloalkenyl or lower cycloalkenyl lower alkyl;
and $R_{10}$ and $R_{11}$ may optionally be connected by a bridging group selected from the group consisting of O, S, $NR_{30}$, or $(CHR_{30})_m$, wherein each $R_{30}$ is independently lower alkyl or hydrogen and m is 1-3; and $R_{12}$ and $R_{13}$ are independently lower alkyl, lower cycloalkyl, lower cycloalkyl lower alkyl, heterocyclic, heterocyclic lower alkyl, lower cycloalkenyl or lower cycloalkenyl lower alkyl;

ring $A_1$ and ring B are independently aromatic containing 6 to 14 ring carbon atoms or cycloalkenyl or cycloalkyl each containing 5 to 14 ring carbon atoms, and $R_{b1}$, $R_{c1}$, $R_{b2}$, $R_{c2}$ are independently hydrogen, lower alkyl or electron donating group and T is $CHR_{31}$, O, S or $NR_{31}$ wherein $R_{31}$ is hydrogen or lower alkyl;

A is N or $CR_{24}$;

D is N or $CR_{25}$;

E is N or $CR_{26}$;

G is $CR_{27}$ or N;

$R_{24}$, $R_{25}$, $R_{26}$ and $R_{27}$ are independently hydrogen or lower alkyl or an electron donating group or $R_{25}$ and $R_{26}$ or $R_{24}$ and $R_{25}$ or $R_{26}$ and $R_{27}$ taken together with the carbon atoms to which they are attached form an aryl ring, but at least one of A, D, E and G is N.

It is also preferred that structures of Formula II have the formula:

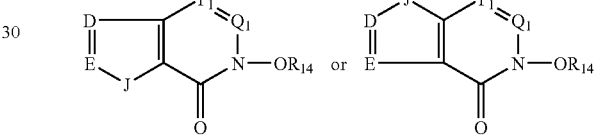

wherein
$Y_1$, $Q_1$ and $R_{14}$, are as defined hereinabove,
D is $CR_{25}$ or N;
G is $CR_{26}$ or N;
J is $NR_{28}$, O, $CR_{28}R_{29}$ or $S(O)_p$;
$R_{25}$ and $R_{26}$ are independently hydrogen or lower alkyl or an electron donating group or $R_{25}$ and $R_{26}$ taken together with the carbon atoms to which they are attached form an aryl group;
$R_{28}$ is hydrogen or electron donating group or lower alkyl;
$R_{29}$ is hydrogen or lower alkyl and
p is 0, 1 or 2.

More preferred structures of Formula II have the formula

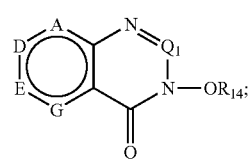

X

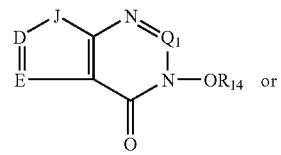

XI

-continued

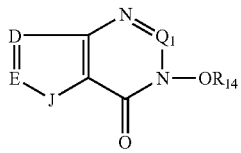

XII wherein
A is N or $CR_{24}$,
D is $CR_{25}$ or N,
E is $CR_{26}$ or N.
G is $CR_{27}$ or N;
J is $NR_{28}$, O, $CR_{28}$, $R_{29}$ or $S(O)_p$; and
$R_{24}$, $R_{25}$, $R_{26}$, $R_{27}$, $R_{28}$, $R_{29}$, p, $Q_1$, and $R_{14}$ are as defined hereinabove.

With respect to Formula II, and all of its various embodiments depicted hereinabove, it is preferred that no more than two of A, D, E, and G are N. It is most preferred that only one of A, D, E, or G is N. Further, it is preferred that $R_{24}$, $R_{25}$, $R_{26}$ or $R_{27}$ are independently hydrogen or an electron donating group, as defined herein. The preferred electron donating groups are lower dialkylamino, especially N,N-dimethylamino and lower alkoxy, e.g., methoxy.

Moreover, it is preferred that T is $CH_2$, O, S or NH and more preferably $CH_2$ or O. Preferred structures of Formula X have the formulae

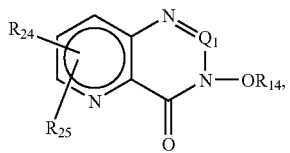

XI

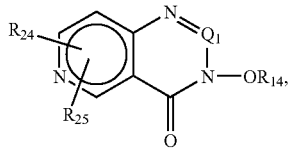

XII

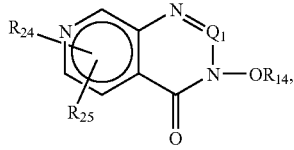

XIII

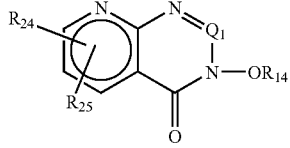

XIV or N-oxides thereof, wherein $R_{24}$, $R_{25}$, $Q_1$ and $R_{14}$ are as defined hereinabove.

Of the structures of Formulae XI-XIV, the most preferred compound is that of XIa viz.

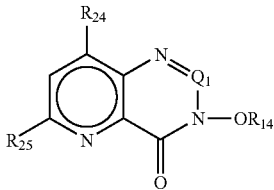

XIa wherein $R_{24}$, $R_{25}$, $Q_1$ and $OR_{14}$ are as defined herein.
Preferred structures of Formula II also have the formula

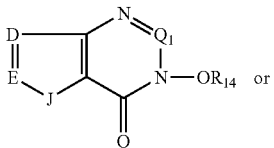

XV

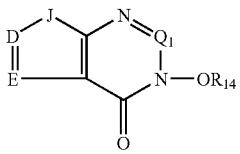

XVI wherein J, E, D, $Q_1$ and $R_{14}$ are as defined hereinabove. It is preferred that $R_{24}$ is hydrogen, lower alkyl or electron donating group as defined hereinabove and $R_{25}$ is hydrogen or lower alkyl. It is most preferred that $R_{25}$ is hydrogen and it is most preferred that $R_{24}$ is an electron donating group or hydrogen.

Preferred values of J are O or S(O)p or NH; the preferred value of p is 1.

Preferred structures of Formula II also have the following formula:

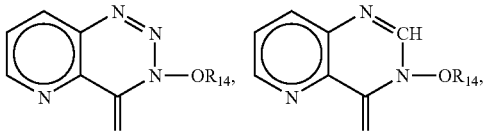

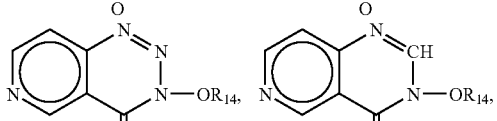

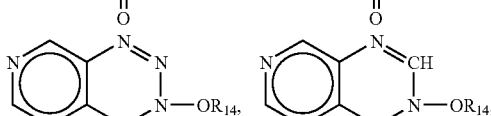

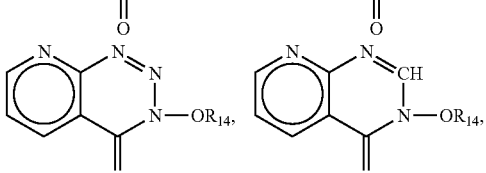

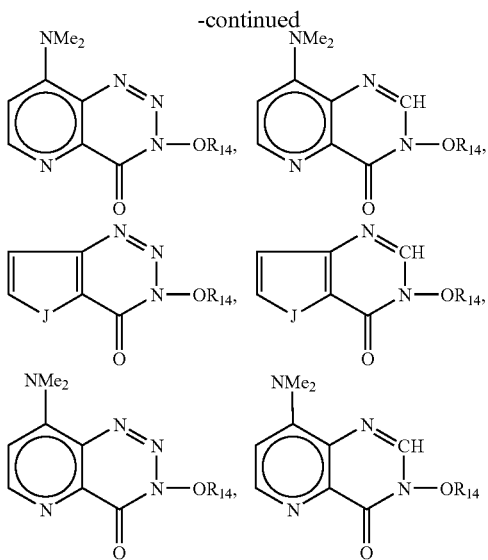

or the N-oxides thereof.

In the various structures described herein whether it is for compounds of Formula I or II or any other embodiment of the present invention depicted herein, the preferred values of T is O, S, NH or $CH_2$. In addition, in the various structures depicted hereinabove, it is preferred that m is 1 and that $R_{30}$ is H.

Compounds of Formula II or salts, especially wherein the cationic portion has the structure of Formula II, are prepared by art recognized techniques. For example compounds of Formula II are prepared by reacting compounds of Formula XVII whenever $R_{14}$ is hydrogen

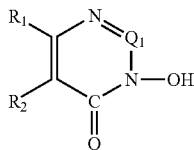
XVII with $R_{14}L$, wherein $R_1$, $R_2$, $Q_1$, and $R_{14}$ is as defined herein and L is a leaving group, such as halo, (e.g. chloro, bromo or iodo). However, if $R_{14}$ is a positively charged electron withdrawing group, then the structures of Formula II is a cation, and in this case, there would be an anion associated with this cationic moiety. For example, when $R_{14}$ is

the compounds of Formula XVII is reacted with

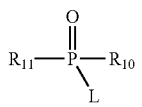

under substitution reaction conditions wherein $R_{12}$ and $R_{11}$ and L are as defined hereinabove. It is preferable that reaction is run in an inert polar organic solvent and that the reactants are soluble therein at room temperature. It is also preferred that the product is insoluble in the solvent at room temperature Examples of the solvent that could be used include chloroform, carbon tetrachloride, ethyl ether, dioxane, tetrahydrofuran, methylene, chloride, and the like. The reaction takes place at effective temperatures, which may range from the melting point of the solvent up to reflux temperatures, but it is preferred that the reaction takes place at about room temperature or at slightly higher temperatures up to the reflux temperature of the solvent. It is especially preferred that the reaction take place at room temperature or at slightly elevated temperatures such as up to 60° C.

Compounds of Formula XVII can also be prepared by art recognized techniques known to one of ordinary skill in the art. An exemplary procedure is as follows:

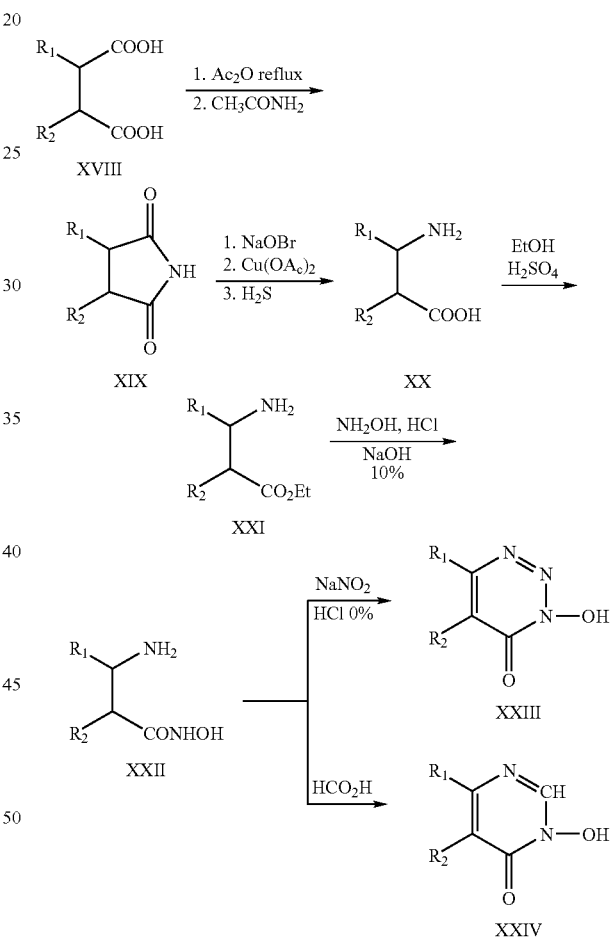

For example, a compound of Formula VII is refluxed with acetic anhydride to give the corresponding anhydride under anhydride formation conditions. The anhydride product was then treated with acetamide under amide forming conditions to give the corresponding cyclic imide XIX. The cyclic imide XIX is subjected to conditions effective for it to undergo Hoffman rearrangement, e.g., by reacting it with sodium hypobromite (or sodium hydroxide and bromine) followed by hydrolysis. For example, the cyclic imide XIX is reacted with NaOBr, Copper (II) acetate and $H_2S$ to provide the amino carboxylic acid (XX) with one less carbon atom. Esterification of acid XX under the esterfying conditions gives the corresponding ester XXI. Treatment of XXI with hydroxylamine in acid (hydroxylammonium salt) under esterification reaction conditions gives the hydroxamic acid derivative XXII. Diazotization followed by intramolecular cyclization gives the azo derivatives XXIII. On the other hand, reaction of the hydroxamic with formic acid under effective conditions, such as by heating the hydroxamic acid with formic acid at effective temperatures e.g., temperatures ranging from just above room temperature up to and including reflux temperatures, and preferably, at the reflux temperature of formic acid gives the product XXIV.

Of course, various combinations and permutations of the formulae described herein are also contemplated by the present invention. In addition, Markush groupings containing less than all of the elements described hereinabove as well as the various permutations thereof are also contemplated by the present invention.

As described herein, the compounds or salts or N-oxides described hereinabove are useful in promoting peptide coupling, i.e., the reaction between a free amino group of a first amino acid or first peptide with a free carboxy group or acylating group of a second amino acid or peptide. The process of the present invention is general; it can be used in effecting the coupling of a dipeptide of an amino acid, a tripeptide and an amino acid, dipeptides, pentapeptide, higher peptides, polypeptides, etc.

When the compound of Formula I or structures of Formula II reacts with an amino compound such as an amino blocked amino acid or protein of the formula $BLK_1$-$AA_1$, the corresponding amino acid ester of the one of the following compounds is formed depending on the identity of the coupling agent:

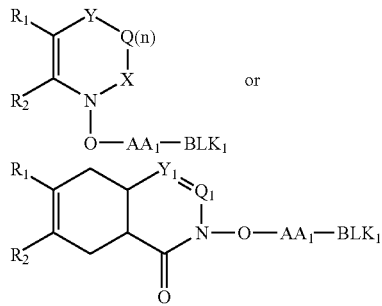

wherein $AA_1$ is an amino acid or protein as defined herein, $BLK_1$ is a blocking group as defined herein and Y, Q, $Q_1$, n, X, $R_1$, and $R_2$ are as defined hereinabove. This amino acid ester can then react with a compound having a free amino group such as an arylamino, alkylamino, lower aryl amino, heterocyclic amino, heterocyclic lower alkylamino, lower cycloalkylamino, lower cycloalkyl lower alkyl amino, and the like designated as $R_{33}R_{34}$ NH, wherein $R_{33}$ and $R_{34}$ are independently hydrogen, lower alkyl, aryl or lower aryl alkyl, to form a compound of the formula:

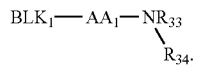

Removal of the blocking group by techniques known to one skilled in the art affords the product:

This technique is extremely useful when the second amino compound is an amino acid or peptide having a free amine group, designated as $AA_2$. For example, if the coupling agent is a compound of Formula I, a peptide may be formed between $AA_1$ and $AA_2$ as follows, for example,

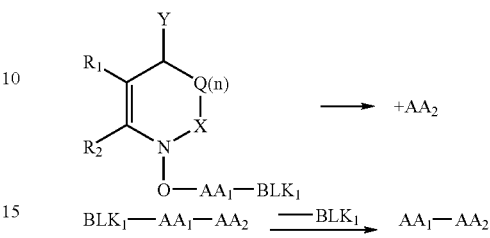

wherein $AA_1$, $AA_2$, $BLK_1$, $R_1$, R, Y, Q, n and X are as defined herein.

If the coupling agent contains a structure of Formula II,

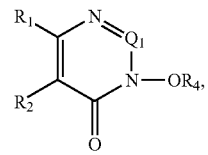

whether compound or cationic portion of the salt, then the reaction becomes

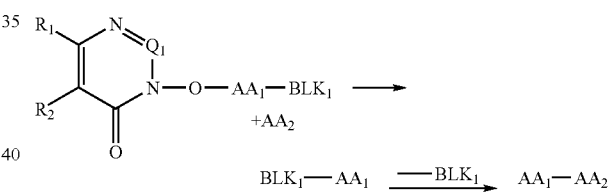

In the reaction $AA_1$, $AA_2$, $BLK_1$, $R_1$, $R_2$, and $Q_1$ are as defined herein.

The blocking group can be any of the blocking groups known in the art but the preferred blocking groups are FMOC, BOC, benzyloxycarbonyl BSMOC and Bspoc.

The term "amino acid" or AA, $AA_1$, or $AA_2$ as used herein refers to an organic acid containing both a basic amino group ($NH_2$) and an acidic carboxyl group. (COOH).

Therefore, said molecule is amphoteric and exists in aqueous solution as dipole ions. (See "The Condensed Chemical Dictionary", $10^{th}$ Ed., edited by Gessner G. Hawley, Van Nostrand Reinhold Company, London, England p. 48 (1981). The preferred amino acids are the α-amino acids. They include but are not limited to the 25 amino acids that have been established as protein constituents. They must contain at least one carboxyl group and one primary or secondary amino group in the amino acid molecule. The term includes such proteinogenic amino acids as alanine, valine, leucine, isoleucine, norleucine, proline, hydroxyproline, phenylalanine, tryptophan, 2,4-diamino butyric acid, methionine, glycine, serine, threonine, cysteine, cystine, glutamic acid, lysine, hydroxylysine, ornithine, arginine, histidine, penicillamine, naphthylamine, α-phenylglycine, aspartic acid, asparagines, glutamine, arginine, tyrosine, and the like.

As used herein, the term "peptide" refers to the class of compounds composed of amino acid units chemically bound together with amide linkages. A peptide may contain as little as two amino acid residues or may consist of a polymer of amino acid residues (polypeptide).

As used herein, the terms "amino acid" and "peptide" also include amino acids and peptides, respectively containing blocking (protecting) groups. These protecting "groups" block the amino group or the carboxyl group of the amino acid or peptide not involved in or taking part in the coupling in order to prevent unwanted side reactions. These protecting groups also protect reactive groups on the side chain.

A number of blocking reagents for amino groups are known in the art and have been utilized in the syntheses of peptides. These blocking groups are discussed in U.S. Pat. Nos. 3,835,175, 4,508,657, 3,839,396, 4,581,167, 4,394,519, 4,460,501 and 4,108,846, the contents of all of which are incorporated by reference as if fully set forth herein. Other amino protecting groups are discussed in U.S. Pat. Nos. 5,221,754, 5,510,491 and 5,637,719 the contents of which are also incorporated by reference. Other amino protecting groups are described in an article entitled "Solid Phase Peptide Synthesis", by G. Barany and R. B. Merrifield in *THE PEPTIDES*, Vol. 2, edited by E. Gross and J. Meienhoffer, Academic Press, N.Y., N.Y. 100-118 (1980), and in the book entitled "PROTECTIVE GROUPS IN ORGANIC SYNTHESIS" by T. W. Green, John Wiley & Sons, New York, the contents of all of which are being incorporated by reference.

The term amino acid protecting group, (BLK, $BLK_1$) as used herein, refers to blocking groups which are known in the art and which have been utilized to block the amino ($NH_2$) group of the amino acid. Blocking groups such as 9-lower alkyl-9-fluorenyloxycarbony, 2-chloro-1-indanylmethoxycarbonyl (CLIMOC) and benz[f]indene-3-methyloxycarbonyl (BIMOC) and dbd-TMOC are discussed in U.S. Pat. Nos. 3,835,175, 4,508,657, 3,839,396, 4,581,167, 4,394,519, 4,460,501 and 4,108,846 referred to hereinabove, the contents of which are incorporated by reference. Moreover, other amino protecting groups such as 2-(t-butyl sulfonyl)-2-propenyloxycarbonyl (Bspoc) and benzothiophene sulfone-2-methoxycarbonyl (Bsmoc). Other N-amino protecting groups include such groups as the t-butyloxycarbonyl (BOC), t-amyloxycarbonyl (Aoc), β-trimethylsilyl-ethyloxycarbonyl (TEOC), adamantyl-oxycarbonyl (Adoc), 1-methyl-cyclobutyloxycarbonyl (Mcb), 2-(p-biphenylyl)propyl-2-oxycarbonyl (Bpoc), 2-(p-phenylazophenyl)propyl-2-oxycarbonyl (Azoc), 2,2-dimethyl-3,5-dimethyloxybenzyloxycarbonyl (Ddz), 2-phenylpropyl-2-oxycarbonyl (Poc), benzyloxycarbonyl (Cbz), p-toluenesulfonyl aminocarbonyl (Tac), o-nitrophenylsulfenyl (Nps), dithiasuccinoyl (Dts), Phthaloyl, piperidine-oxycarbonyl, formyl, trifluoroacetyl and the like.

These protecting groups can be placed into four categories:
1) a base labile Nα-amino acid protecting group such as FMOC, and the like.
2) protecting groups removed by acid, such as Boc, TEOC, Aoc, Adoc, Mcb, Bpoc, Azoc, Ddz, Poc, Cbz, 2-furanmethyloxycarbonyl (Foc), p-methoxybenzyloxycarbonyl (Moz), Nps, and the like.
3) protecting groups removed by hydrogenation such as Dts, Cbz.
4) protecting groups removed by nucleophiles, such as Bspoc, Bsmoc and Nps and the like.
5) protecting groups derived from carboxylic acids, such as formyl, acetyl, trifluoroacetyl and the like, which are removed by acid, base or nucleophiles.

A variety of carboxy protecting groups known in the art may be employed. Examples of many of these possible groups may be found in "Protective Groups in Organic Synthesis", by T. W. Green, John Wiley & Sons, 1981, the contents of which are incorporated by reference. These examples include such groups as methyl ester, t-butyl ester, β-trimethylsilylethyl ester, benzyl ester and the like.

In addition, during the course of protein synthesis, it may be necessary to protect certain side chains of the amino acids to prevent unwanted side reactions. The various protecting groups are discussed in U.S. Pat. No. 5,360,920, the contents of which are incorporated herein by reference.

The term "acylating group of an amino acid or peptide" refers to a group on the free carboxy end of the amino acid or peptide that facilitates the acylation reaction, i.e., nucleophilic substitution at the acyl carbon. Examples include the free acid, acid halide, esters, such as lower alkyl esters, phenoxy esters which are unsubstituted or substituted with 1-5 electron withdrawing groups as defined herein; or an anhydride and the like. The preferred acylating derivative is the acid, acid halide, especially the acid chloride or fluoride, and the phenoxy ester.

The preferred acylating amino acid is an amino acid group of the formula

wherein BLK is an amino protecting group
AA is an amino acid less the H on the COOH moiety and
M is halo or

wherein Ra is independently halo, lower alkyl, nitro, cyano or other electron withdrawing group and b is 0-5. When b is 0, the phenyl group is unsubstituted.

The most preferred acylating group of an amino acid is the amino acid chloride or fluoride. The preparation and use of amino acid chlorides as an acylating derivative is discussed in an article by Carpino, et al. in *J. Org. Chem.*, 1986, 51, 3734-3736, the contents of which are incorporated herein by reference. Briefly, amino acid chlorides can be prepared by reacting the amino acid with thionyl chloride and recrystallizing the product from a recrystallization reagent, such as $CH_2Cl_2$-hexane.

The preparation and use of amino acid fluorides in peptide synthesis are discussed U.S. Pat. No. 5,360,920, the contents of which are incorporated herein by reference. As described therein, the amino acid fluorides can be prepared by reacting an N-protected amino acid with the reagent cyanuric fluoride. This reaction can be run at temperatures as low as 0° C. and up to the refluxing temperature of the solvent, but it is preferred that the reaction is run at room temperature. It can also be run in an inert solvent, such as pyridine/$CH_2Cl_2$ and the like. The cyanuric fluoride can be prepared from the corresponding chloride in the presence of potassium fluoride at elevated temperatures ranging from 150° to 250° C., according to the following equation

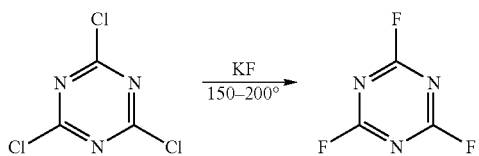

A typical preparation of the peptide in accordance with the present invention involves the following steps 1) protection of the free carboxyl group in a first amino acid or a first peptide, unless the amino acid or peptide is anchored to a solid support.

2) protection of the free amino group of a second amino acid or peptide.

3) protection of the side chains, if necessary.

4) coupling the first amino acid or peptide with the second amino acid or peptide in the presence of compounds of Formula I.

5) removal of the protecting groups.

The procedure of steps 1-3 can be performed in any order.

In the coupling step, the compounds of Formula I or II or salts or N-oxides thereof or cation of Formula II is present in effective amounts. Usually, the first amino acid or peptide is present in approximately equimolar amounts with the second amino acid or peptide. Furthermore, the amount of the compound having Formula I or II used depends upon the amount of peptide or amino acid which is present in the least amount (i.e. the limiting reagent); thus the molar ratio of the compound of Formula I or II to the amino acid or peptide present in the least molar amount, ranges from about 1:3 to about 3:1, although it is preferred that approximately equimolar amounts of the compound of Formula I or II (or salt or N-oxide thereof or cation of Formula II) the first amino acid or peptide and the second amino acid or peptide be used.

The coupling reaction usually takes place in an inert organic solvent such as dimethylformamide (DMF) or ethers, such as ethyl ether, THF or dioxane. In fact DMF is the preferred solvent in the solid phase synthesis because of its favorable solvation properties. The reaction takes place under mild conditions usually ranging from about 0° C. to about 30° C. After the peptide is formed, the blocking groups are removed by techniques known to one skilled in the art.

The following sequence is illustrative of the coupling reaction; in the examples below, amino acids (AA) are used, although the procedure is general for amino acids and/or peptides:

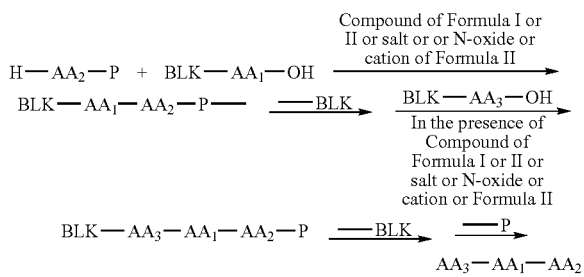

In the above scheme, BLK is an amino acid blocking group, $AA_1$, $AA_2$ and $AA_3$ are first, second and third amino acid respectively and P is a carboxy protecting group.

As shown by the above scheme, the N-α amino protected amino acid is reacted with a second amino acid in which the carboxy group is protected.

A peptide is formed between the first amino acid and the second amino acid. The peptide chain can be increased by removing the alpha amino protecting group by techniques known to one skilled in the art and then reacting the corresponding dipeptide with another N-t amino protected amino acid in the presence of a compound of Formula I to form the corresponding tri-peptide. The N-α amino protecting group of the tri-peptide is removed and the above cycle is repeated until the desired peptide has been obtained.

The present invention can readily be utilized in solid phase peptide synthesis. Solid phase peptide synthesis is based on the stepwise assembly of a peptide chain while it is attached at one end to a solid support or solid phase peptide resin. Two methods are generally well known in the art.

One, the Merrifield method, employs a solid support for attachment of the amino acid or peptide residues. This method employs N-protected amino acids as building blocks which are added to an amino acid or peptide residue attached to the solid support at the acyl (acid) end of the molecule. After the peptide bond has been formed, the protecting group is removed and the cycle repeated. When a peptide having the desired sequence has been synthesized, it is then removed from the support.

The second method, the inverse Merrifield method, employs reagents attached to solid supports in a series of columns. The amino acid or peptide residue is passed through these columns in a series to form the desired amino acid sequence.

These methods are well known in the art as discussed in U.S. Pat. Nos. 4,108,846, 3,839,396, 3,835,175, 4,508,657, 4,623,484, 4,575,541, 4,581,167, 4,394,519 as well as in *Advances in Enzymology*, 32, 221 (1969) and in PEPTIDES, Vol. 2, edited by Erhard Gross and Johannes Meienhoffer, Academic Press, New York pp. 3-255 (1980) and the contents thereof are incorporated herein by reference as if fully set forth herein.

The compounds of the present invention are useful as coupling agents or bases in peptide coupling. However, their effectiveness is also a function of the solvent system which is used to dissolve the reactants and bases used in the coupling reaction. If the compound of the present invention is not too soluble in the solvent used in the coupling method, then it should be converted to a form more soluble in the solvent or the solvent should be changed to one in which it is soluble. This is usually not a problem in peptide coupling conducted in solution. But, with some peptide synthesizers, the option of changing the solvent is not available. For example, with some synthesizers, DMF or N-methylpyrrolidone is the solvent utilized. However, compounds of the present invention may not be too soluble in the solvent utilized, such as DMF or N-methylpyrrolidone. Thus, to overcome this problem the compound of the present invention is converted to a compound which is soluble in the solvent utilized, such as DMF or N-methylpyrrolidone. For example, if the coupling agent or base of the present invention is that of Formula I and if $R_{10}$ or $R_{11}$ is aryl or heteroaryl or if $A_1$ or B is aryl or heteroaryl, then the trick to overcome this problem is to place a t-butyl or t-amyl group or any other group wherein the carbon atom attached to the aryl or heteroaryl ring is a tertiary carbon.

If $R_{10}$ or $R_{11}$ or $A_1$ or B contain more than one ring it is preferred that the t-butyl or amyl group or other tertiary carbon group, such as a tertiary hydrocarbyl group (containing only carbon and hydrogen atoms) is attached to the ring attached to the phosphorus atom. If more than one such group is attached to the rings, it is preferred that these groups are the same.

The following examples further illustrate the present invention.

In the examples, the following abbreviations are utilized:

| | |
|---|---|
| HOAt | 1-hydroxy-7-azabenzotriazole |
| DIEA | diisopropylethylamine |
| TEA | triethylamine |
| CBZ or Cbz | benzyloxycarbonyl |
| EDC | N-ethyl-N'-[3-dimethylaminopropyl] carbodiimide hydrochloride |
| Aib | aminoisobutyric acid |
| THF | tetrahydrofuran |
| DMF | dimethylformamide |
| TCFH | 1,1,3,3-tetramethylchloroformamidinium hexafluorophosphate |
| PyClu | 1,1,3,3-bis(tetramethylene)chlorouronium hexafluorophosphate |
| PyBrop | tris(pyrrolindino)bromophosphonium hexafluorophosphate |
| TFA | trifluoroacetic acid |
| TMP | 2,4,6-trimethylpyridine |
| PCA | p-chloroaniline |
| DPOPOAt | diphenoxyphosphoryloxy-7-azabenzotriazole |
| HDATU | O-(3,4-dihydro-4-oxo-5-azabenzo-1,3-diazin-3-yl)-1,1,3,3-tetramethyl-uronium hexafluorophosphate |
| N-HATU | 1-[bis(dimethylamino)methylene]-1H-1,2,3-triazolo-[4,5-b]pyridin hexafluorophosphate 3-oxide |
| O-Dhad | 3-oxy-4-oxo-3,4-dihydro-5-azabenzo-1,2,3-triazine |
| O-HATU | N-[(1H-1,2,3-triazolo[4,5-b]pyridin-1-yloxy) (dimethylamino)methylene]-N-methylmethanaminium hexafluorophosphate |
| HDTU | O-(3,4-dihydro-4-oxo-1,2,3-benzotriazin-3-y1)-1,1,3,3-tetramethyluronium hnexaflurorphosphate |
| HODhat | 3-hydroxy-4-oxo-3,4-dihydro-5-azabenzo-1,2,3-triazine |
| HODhbt | 3-hydroxy-4-oxo-3,4-dihydro-1,2,3-benzotriazine |
| DEPOAt | diethoxyphosphoryloxy-7-azabenzotriazole |
| DtpOAt | di(o-tolyl)phosphinyloxy-7-azabenzotriazole |
| HODhad | 3-hydroxy-4-oxo-3,4-dihydro-5-azabenzo-1,3-diazine |
| Odhad | 3-oxy-4-oxo-3,4-dihydro-5-azabenzo-1,3-diazine |
| HDADU | O-(3,4-dihydro-4-oxo-5-azabenzo-1,3-diazin-3-yl)-1,1,3,3-tetramethyluronium hexafluorophosphate |
| HDAPyU | O-(3,4-dihydro-4-oxo-5-azabenzo-1,2,3-triazin-3-yl)-1,1,3,3-bis(tetramethylene)uronium hexafluorophosphate |
| PyDAOP | [(3,4-Dihydro-4-oxo-5-azabenzo-1,2,3-triazin-3-yl)oxy] tris(pyrrolidino)phosphonium Hexafluorophosphate |
| DtpOBt | di(o-tolyl)phosphinyloxybenzotriazole |
| DtpODhbt | 3-[di-o-tolyl)phosphinyloxy]-3,4-dihydro-4-oxo-2,3 benzotriazine |
| DEPDBt | 3-(diethoxyphosphoryloxy)-3,4-dihydro-4-oxo-1,2,3-benzotriazine |
| DPOPDBt | 3-(diphenoxyphosphoryloxy)-3,4-dihydro-4-oxo-1,2,3-benzotriazine |
| DPOPOAt | diphenoxyphosphoryloxy-7-azabenzotriazole |
| PyDOP | [(3,4-dihydro-4-oxo-1,2,3-benzotriazin-3-yl)oxy]tris (pyrrolidino)-phosphonium hexafluorophosophate |
| HDPyU | O-(3,4-dihydro-4-oxo-1,2,3-benzotriazin-3-yl)-1,1,3,3-tetramethyluronium hexafluorophosphate |
| DIC | diisopropylcarbodiimide |
| DCHMA | N,N-dicyclohoxylmethylamine |
| DmppOAt | 2,8-dimethyl phenoxaphosphinyloxy-7-azabenzotriazole |
| Bt | benzotriazole |
| Pfp | pentafluorophenyl ester |
| N-HBTU | 1-[bis(dimethylamino)methylene]-1H-benzotriazolium hexafluorophosphate-3-oxide |
| O-HBTU | N-[1H-benzotriazol-1-yloxy)(dimethylamino)methylene]-N-methylmethanaminium hexafluorophosphate |

EXAMPLE 1

Diethoxyphosphoryloxy-7-azabenzotriazole (DEPOAt)

A solution of HOAt (1.36 g, 10 mmol) and triethylamine (TEA) (1.39 mL, 10 mmol) in 15 ml of dry benzene was cooled in an ice bath. To the solution was added dropwise with stirring a solution of diethyl chlorophosphate (1.72 g, 1.45 ml, 10 mmol) in 10 ml of dry benzene under $N_2$. The addition was completed in 10 min, and stirring was continued at ice-bath temperature for 1 hour and then at room temperature for an additional 4 hours. The reaction mixture was cooled to 5-10° C. and TEA HCl was removed quickly by filtration. The colorless clear solution was evaporated to dryness while the temperature was kept below 35° C. Dry hexane was added to the oily residue and the whole was tightly capped under $N_2$, and placed in a refrigerator (−20° C.) for 2 hours. The oily residue solidified as a white solid, which was then recrystallized from dry $CH_2Cl_2$-hexane to give 1.74 g (63%) of the ester as colorless plates: mp 48-50° C.; $^1$H NMR ($CDCl_3$): δ 8.77 (dd, 1H), 8.40 (dd, 1H), 7.44 (dd, 1H), 4.57 (m, 4H, 2$CH_2$), 1.47 (2t, 2$CH_3$); IR (film on NaCl plate): 2987 (m), 1596 (m), 1395 (m), 1306 (s), 1026 (vs), 838 (m), 775 (s), 699 (m) $cm^{-1}$.

Anal. Calcd for $C_9H_{13}N_4O_4P$: C, 39.71; H, 4.81; N, 20.58. Found: C, 39.84; H, 4.72; N, 20.54.

EXAMPLE 2

Di(o-tolyl)phosphinyloxy-7-azabenzotriazole (DtpOAt)

A solution of HOAt (0.136 g, 1 mmol) and DIEA (0.21 ml, 1.2 mmol) in 10 ml of dry $CH_2Cl_2$ was cooled in an ice bath and 0.2647 g (1 mmol) of di(o-tolyl)phosphinoyl chloride (DTP-Cl) was added to the solution portion wise with stirring under $N_2$. The stirring was continued in the ice-bath for 30 minutes and then at room temperature for 5 hours. The resulting colorless solution was washed with cold saturated $NaHCO_3$ solution (2×10 ml) and brine (2×10 ml), and dried over $MgSO_4$ to give 0.26 g (69%) of white solid after removing the solvent. Recrystallization from $CH_2Cl_2$-hexane gave 0.21 g of an analytically pure sample of the ester as colorless block crystals: mp 170-172° C.; $^1$H NMR ($CDCl_3$): δ 8.74 (dd, 1H), 8.32 (d, 1H), 7.99 (dd, 1H), 7.56 (m, 2H, Ar—H), 7.35 (m, 6H, Ar—H), 2.70 (d, 6H, 2$CH_3$); IR (KBr): 3064 (w), 1592 (s), 1458 (m), 1379 (m), 1334 (m), 1238 (sh, s), 1113 (s), 928 (m), 811 (s), 770 (s), 691 (s) $cm^1$.

Anal. Calcd for $C_{19}H_{17}N_4O_2P$: C, 62.62; H, 4.70; N, 15.37. Found: C, 62.23; H, 4.72; N, 15.47.

EXAMPLE 3

Synthesis of 3-hydroxy-4-oxo-3,4-dihydro-5-azabenzo-1,2,3-triazine (HODhat)

A. Quinolinimide. 2,3-Pyridinedicarboxylic acid (22.5 g, 0.135 mol) was added to 25 ml of acetic anhydride and the mixture was heated with stirring to reflux on a steam-bath. A clear colorless solution was obtained after about 1 hour, and the heating was continued for 2 more hours. Then, acetic acid and excess acetic anhydride were distilled off (~12.6 g) until the temperature of the residual solution reached 165° C. The residue which remained in the flask solidified to a dust red solid upon cooling to room temperature.

To the above solid, acetamide (14 g, 0.23 7 mol, 1.75 equiv) was added and the mixture was heated overnight by means of an oil-bath, keeping the temperature at 120-125° C. After cooling to room temperature, the solid was collected and washed with acetic acid (2×10 ml) and water (3×50 ml). The gray solid was suspended in 250 ml of hot water and the mixture stirred for 15 min to give by filtration 15 g (75%) of the above-identified imide as a gray solid: mp 237°-239° C. (lit. mp 233° C.).

B. 3-Aminopicolinic Acid. Quinolinimide (50 g, 0.344 mol) was dissolved in 1000 ml of 10% NaOH while cooling in an ice-bath and to the solution was added slowly with stirring and cooling a cold NaOBr solution, which had been obtained by mixing 56 g (18 ml, 0.344 mmol) of $Br_2$ with 350 ml of 15% NaOH in an ice-bath. After the addition had been completed, stirring was continued in the ice-bath for 15 min and at room temperature for 1 hour. The resulting mixture was then heated to 85° C. with stirring for 1 hour. After cooling, the mixture was neutralized to pH 5-6 by means of 50% $H_2SO_4$ and the whole was kept at room temperature overnight.

The resulting white cloudy mixture was heated and the clear solution treated with a hot solution of 22 g (0.11 mol) of copper (II) acetate monohydrate in 400 ml of $H_2O$ and 10 ml of acetic acid. The mixture was heated with a steam bath for 15 min and then cooled at room temperature and the copper salt collected and washed twice with cold water.

The copper salt was re-suspended in 500 ml of water, and $H_2S$ was passed through the suspension for 2 to 3 hours while stirring. Black CuS was removed from the mixture by filtration and the filtrate decolorized with charcoal. Removal of water gave a dust yellow solid, which was recrystallized form water-ethanol (1:1 v/v) to give 29 g (60%) of the above-identified acid as a cream-yellow solid: mp 212-214° C. (lit. mp 210° C.).

C. Ethyl 3-Aminopicolinate. A mixture of 3-aminopicolinic acid (5.07 g, 36 mmol), absolute ethanol (20 ml) and concentrated $H_2SO_4$ (6 ml) was refluxed for 48 hours. After cooling, the mixture was concentrated to about 15 ml and poured into 15 g of ice. The mixture was basified with concentrated aqueous ammonia to pH 8-9 with cooling in an ice bath, and the white precipitate that separated was collected by filtration. The filtrate was extracted with ether (4×50 ml), and the ether layer washed with brine (4×50 ml) and dried over $MgSO_4$. Evaporation of the ether solution afforded another solid. Both fractions were combined and recrystallized from benzene-hexane to give 4.05 g (68%) of the above-identified ethyl ester as white needles: mp 126-127.5° C. (lit mp 131-133° C., yield 42%); $^1$H NMR ($CDCl_3$): δ8.09 (dd, 1H), 7.23 (dd, 1H), 7.04 (dd, 1H), 5.76 (s, 2H, $NH_2$), 4.46 (q, 2H, $CH_2$), 1.45 (t, 3H, $CH_3$).

D. 3-Amino-2-picolinehydroxamic Acid. Hydroxylamine hydrochloride (16.3 g, 0.233 mol) was added slowly with stirring and cooling to 1100 ml of aqueous NaOH solution prepared from 18.7 g (0.467 mol) of NaOH. To the solution, 19.4 g (0.116 mol) of the ethyl ester prepared in Section C hereinabove was added portion wise followed by 110 ml of methanol, and the mixture was stirred at room temperature for 48 hours. The solution was concentrated under reduced pressure to about 100 ml and neutralized with cooling to pH 5-6 with 25% HCl. A white precipitate that separated was collected by filtration, washed with a small amount of cold water, and dried over $P_2O_5$ in vacuo to give 17.8 g (100%) of the 3-amino-2-picoline-hydroxamic acid as a white solid, which was pure enough for the next step. An analytical sample of this acid was obtained in 90% yield after two recrystallizations from $MeNO_2$-MeOH-EtOAc as white block-like crystals: mp 131-133° C. (lit. mp 143-145° C., yield 49%); $^1$H NMR (DMSO-$d_6$CDCl$_3$): δ10.91 (s, 1H, OH), 8.89 (s, 1H, NH), 7.74 (t, 1H), 7.16 (d, 2H), 6.71 (s, 2H, $NH_2$); IR (KBr): 3443 (m), 3334 (s), 1660 (s, CON), 1606 (s), 1262 (w), 1017 (w), 805 (m) cm$^1$.

E. 3-Hydroxy-4-oxo-3,4-dihydro-5-azabenzo-1,2,3-triazine (HODhat). To a suspension of finely powdered product produced in step D hereinabove (7.3 g, 47.6 mmol) in 28 ml of water, 8.5 ml of concentrated HCl was added while stirring. While cooling in an ice-bath, a cold solution of $NaNO_2$ (4.93 g, 71.4 mmol) in 5 ml of water was added dropwise to the mixture and the temperature was maintained below 5° C. After completion of the addition, stirring in the ice-bath was continued for another 30 minutes, and the solid which had precipitated was collected by filtration, washed with a small amount of cold water and air dried to give 2.52 g (32%) of the triazine as a yellow solid: mp 195° C. (explodes) [lit mp: 195° C. (explodes)]. The analytical sample (2.1 g) was obtained by recrystallization from EtOHwater (9:1 v/v) as light orange-yellow needles: mp 203° C. (explodes); $^1$H NMIR (DM-SOd$_6$): δ9.13 (dd, 11H), 8.65 (dd, 111), 8.08 (dd, 11H); IR (KBr): 2600 (broad, OH), 1713 (vs, C(O)N), 1574 (s), 1420 (m), 1230 (sh, s), 1185 (s), 1066 (sh, s), 974 (sh, m), 794 (m) cm$^{-1}$.

3-Hydroxypicolinic acid (1.6 g, 20%) was also isolated from the mother liquor as light pink needles: mp 222-224° C. (lit. mp 220-222° C.). Anal. Calcd for $C_6H_5NO_3$: C, 51.80; H, 3.62; N, 10.07. Found: C, 51.52; H, 3.58; N, 9.98.

EXAMPLE 4

3-Hydroxy-4-oxo-3,4-dihydro-5-azabenzo-1,3-diazine (HODhad)

A mixture of 1.224 g (8 mmol) of the product produced in Step D of Example 3 and 3 ml of 98% formic acid were heated under reflux for 15 minutes after which 8 ml of water was added, and the whole was boiled for 15 minutes and cooled to room temperature. The precipitate that separated was collected by filtration and washed with water (2×5 ml). After being boiled with ethanol twice, there was obtained 0.71 g (55%) of HODhad, which was obtained in an analytically pure form as a yellow solid: mp 318.5-320° C. (dec.); $^1$H NMR (DMSO-$d_6$): δ12.15 (br, 1H, OH), 8.85 (dd, 1H), 8.69 (s, 1H, CH), 8.17 (dd, 1H), 7.84 (dd, 1H); IR (KBr): 2625 (broad, OH), 1683 (sh, vs, CON), 1600 (w), 1446 (m), 1410 (s), 1359 (s), 1223 (s), 990 (s), 902 (m), 791 (s) cm$^{-1}$.

Anal. Calcd for $C_7H_5N_3O_2$: C, 51.53; H, 3.09; N, 25.76. Found: C, 51.46; H, 3.00; N, 25.80.

EXAMPLE 5

CBZ-Aib-ODhat

In an ice bath, 0.3168 g of EDC.HCl (1.65 mmol) was added with stirring to a suspension of CBZ-Aib-OH (0.3 555 g, 1.5 mmol) and HODhat (the product of Ex. 4) (0.246 g, 1.5 mmol) in 10 ml of THF and 5 ml of DMF. The resulting mixture was stirred at room temperature for 3 hours. Solvents were removed in vacuo and the oily residue was extracted with 40 ml of EtOAc. The EtOAc solution was washed with 5% aqueous citric acid (3×10 ml), 10% $NaHCO_3$ solution (3×10 ml) and brine (3×10 ml), and dried over $MgSO_4$.

Evaporation of solvent gave a cream yellow oily residue, which solidified after drying in vacuo over $P_2O_5$ overnight. The crude solid was purified by flash chromatography with EtOAc as eluent to give 0.46 g (80%) of the above-identified ester as a cream yellow solid: mp 57-59° C.; $^1$H NMR ($CDCl_3$): δ 9.05 (dd, IH), 8.49 (dd, IH), 7.86 (dd, IH), 7.26 (m, 5H, $C_6H_5$), 5.47 (s, IH, NH), 5.10 (s, 2H, $CH_2$), 1.73 (s, 6H, $2CH_3$); IR (KBr): 1813 (m, COO), 1735 (vs, NCO), 1267 (s), 1052 (s) cm$^{-1}$.

Anal. Calcd for $C_{18}H_{17}N_3O_5$: C, 56.39; H, 4.47; N, 18.27. Found C, 56.10; H, 4.56; N, 18.08.

EXAMPLE 6

CBZ-Aib-ODhad

As described for EXAMPLE 6, 0.2447 g (1.5 mmol) of HODhad (the product of Ex. 5) was treated with 0.3555 g (1.5 mmol) of CBZ-Aib-OH in the presence of EDC HCl in 15 ml of a THF-DMF mixture (2:1) to give 0.52 g (90%) of the above product as a white solid: mp 48-50° C.; $^1$H NMR (CDCl$_3$): δ 8.89 (dd, 1H), 8.13 (dd, 1H), 7.92 (s, 1H, CH), 7.71 (dd, 1H), 7.36 (m, 5H, C$_6$H$_5$), 5.47 (s, 1H, NH), 5.15 (s, 2H, CH$_2$), 1.75 (s, 6H, 2CH$_3$); IR. (KBr): 1809 (s, COO), 1718 (vs, NCO), 1590 (sh, m), 1522 (sh, m), 1468 (m), 1274 (sh, s), 1059 (s), 974 (w) cm$^{-1}$.

Anal. Calcd for C$_{19}$H$_{18}$N$_4$O$_5$: C, 59.68; H, 4.74; N, 14.65. Found: C, 59.43; H, 4.80; N, 14.58.

EXAMPLE 7

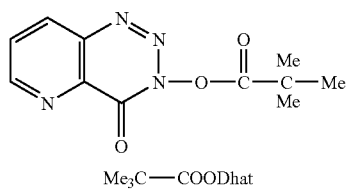

Me$_3$C—COODhat

Under an atmosphere of dry N$_2$, TEA (0.42 ml, 3 mmol) was added to a suspension of HODhat (0.3282 g, 2 mmol) in 10 ml of dry methylene chloride. The resulting mixture was cooled to 0° C. and a solution of pivaloyl chloride (0.27 ml, 2.2 mmol) in 5 ml of dry methylene chloride was introduced dropwise with stirring. The stirring was continued for 30 minutes in an ice-bath, and the temperature was allowed to rise to room temperature. After 4 hours, the mixture was diluted with 30 ml of CH$_2$Cl$_2$ and the whole washed with saturated NaHCO$_3$ (3×20 ml), brine (2×20 ml), and water (2×20 ml), and finally dried over anhydrous MgSO$_4$. Evaporation of solvent gave a pale yellow solid, which was recrystallized from EtOAc-hexane to give 0.31 g (6 1%) of the analytically pure ester product as colorless needles: mp 137-139° C.; $^1$H NMR (CDCl$_3$): δ 9.16 (dd, 1H), 8.57 (dd, 1H), 7.95 (dd, 1H), 1.51 (s, 9H, 3CH$_3$); IR (KBr): 3056 (s), 1797 (vs, COO), 1735 (vs, CONO), 1566 (s), 1479 (m), 1215 (s), 1181 (m), 1056 (sh, s), 1016 (m), 974 (m), 831 (s) cm$^{-1}$.

Anal. Calcd for C$_{11}$H$_{12}$N$_4$O$_3$: C, 53.21; H, 4.87; N, 22.57. Found: C, 53.08; B, 4.74; N, 22.51.

EXAMPLE 8

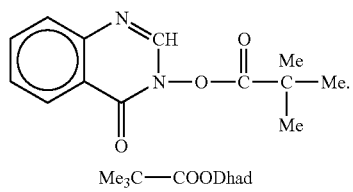

Me$_3$C—COODhad

Using the procedure described in Example 8, HODhad, (0.3708 g, 2.3 mmol), prepared as described in Example 5, was treated with pivaloyl chloride (0.31 ml, 2.53 mmol) in 15 ml of dry CH$_2$Cl$_2$ in the presence of TEA (0.48 ml, 3.45 mmol) to give 0.37 g (65%) of Me$_3$C—COODhad as a white solid. The analytical sample (0.26 g) was obtained after two recrystallizations from EtOAc-hexane as colorless crystals: mp 125-126.5° C.; $^1$H NMR(CDCl$_3$): δ8.91 (dd, 1H), 8.13 (dd, 1H), 8.07 (s, 1H, CH), 7.73 (dd, 1H), 1.48 (s, 911, 3CH$_3$); IR (KBr): 3036 (w), 1794 (s, COO), 1715 (vs, CONO), 1583 (sh, m), 1464 (m), 1427 (m), 1296 (s), 1059 (vs), 1018 (s), 824 (m) cm$^{-1}$.

Anal. Calcd for C$_{12}$H$_{13}$N$_3$O$_3$: C, 58.29; H, 5.29; N, 17.00. Found: C, 58.34; B, 5.28; N, 17.02.

EXAMPLE 9

O-(3,4-Dihydro-4-oxo-5-azabenzo-1,2,3-triazin-3-yl)-1,1,3,3-tetramethyluronium Hexafluorophosphate (HDATU)

Under an atmosphere of dry N$_2$, 0.22 ml (1 65 mmol) of TEA was added to a suspension of HODhat (0.246 g, 1.5 mmol), prepared as in Example 4, in 10 ml of dry CH$_2$Cl$_2$. After stirring for 5 min, the resulting light yellow clear solution was cooled to 0° C. in an ice-bath and 0.4209 g (1.5 mmol) of 1,1,3,3-tetramethyluronium Hexafluorophosphate (TCFH) was introduced portion wise with stirring. The stirring was continued for 30 minutes in an ice-bath and then at room temperature for 1.5 hours. The precipitate which had separated was collected by filtration and washed twice with methylene chloride and recrystallized twice from MeCN-ether to give 0.42 g (69%) of analytically pure hexafluorophosphate product as a white solid: mp 152° C. (explodes); $^1$H NMR(CD$_3$CN): δ 9.19 (dd, 1H), 8.69 (dd, 1H), 8.13 (dd, 1H), 3.21 (s, 12H, 4CH$_3$); IR (KBr): 1738 (vs), 1702 (vs, CON), 1526 (m), 1457 (m), 1412 (s), 1266 (m), 1165 (sh, s), 1072 (m), 964 (s), 850 (sh, vs), 708 (s) cm$^{-1}$.

Anal. Calcd for C$_{11}$H$_{15}$N$_6$O$_2$PF$_6$: C, 32.36; H, 3.70; N, 20.58. Found: C, 32.14; H, 3.79; N, 20.47.

EXAMPLE 10

O-(3,4-Dihydro-4-oxo-5-azabenzo-1,3-diazin-3-yl)-1,1,3,3-tetramethyluronium Hexafluorophosphate (HDADU)

Using the procedure of Example 10, the HODhad (0.2447 g, 1.5 mmol), prepared in Example 5, was treated with TCFH (0.4209 g, 1.5 mmol) in 10 ml of dry CH$_2$Cl$_2$ in the presence of TEA (030 ml, 2.1 mmol) to give 0.55 g (90%) of the above-identified hexafluorophosphate product as a white solid, which was recrystallized twice from MeCN-ether to give 0.48 g (79%) of analytically pure salt as a white solid: mp 203-205° C. (dec.); $^1$H NMR (CD$_3$CN): δ 8.91 (dd, 1H), 8.64 (s, 1H, CH), 8.22 (dd, 1H), 7.88 (dd, 1H), 3.17 (s, 12H, 4CH$_3$); IR (KBr): 1701 (vs, CON), 1605 (sh, m), 1528 (s), 1471 (s), 1416 (sh, s), 1266 (s), 1171 (m), 1068 (w), 965 (s), 852 (sh, vs), 718 (s) cm$^{-1}$.

Anal. Calcd for C$_{12}$H$_{16}$N$_5$O$_2$ PF$_6$: C, 35.38; 11, 3.96; N, 17.19. Found: C, 35.51; H, 3.86; N, 17.33.

EXAMPLE 11

O-(3,4-Dihydro-4-oxo-5-azabenzo-1,2,3-trazin-3-yl)-1,1,3,3-bis(tetramethylene)-uronium Hexafluorophosphate (HDAPyU)

To a mixture of 0.4923 g (3 mmol) of HODhat as prepared in Example 4 and 0.46 ml (3.3 mmol) of TEA in 25 ml of dry CH$_2$Cl$_2$ at 0° C., 1.0 g (3 mmol) of PyClu was added portion wise with stirring under an atmosphere of dry N$_2$. Stirring was continued for 1 hour in an ice-bath and then at room temperature overnight. The clear light yellow mixture was diluted with CH$_2$Cl$_2$ to 50 ml and washed with ice cold water (2×15 ml) and dried over MgSO$_4$. The solvent was removed, and the oily residue was dissolved in 5 ml of MeCN to which 30 ml of ether was added, and the whole was stored at −20° C. for several days until the oil solidified. The solid was collected by filtration and redissolved in 20 ml of CH$_2$Cl$_2$, and the solution washed with ice cold water (2×5 ml) and dried over MgSO$_4$. Removal of solvent gave a pink-yellow solid which was recrystallized from MeCN-ether to give 0.42 g (3 0%) of the above-identified uronium salt product as white crystals: mp 136.5° C. (explodes); $^1$H NMR (CD$_3$CN) δ9.17 (dd, 1H), 8.67 (dd, 1H), 8.11 (dd, 1H), 3.75 (t, 8H, 4NCH$_2$), 1.97 (m, 8H, 4CH$_2$); IR (KBr): 2985 (m), 1734 (vs, CON), 1679 (vs), 1448 (sh, s), 1341 (m), 1169 (m), 1072 (m), 964 (m), 846 (sh, vs) cm$^{-1}$.

Anal. Calcd for C$_{15}$H$_{19}$N$_6$O$_2$PF$_6$: C, 39.13; H, 4.16; N, 18.26.

Found: C, 38.94; B, 4.08; N, 18.30.

EXAMPLE 12

[(3,4-Dihydro-4-oxo-5-azabenzo-1,2,3-triazin-3-yl)oxy]tris(pyrrolidino)phosphonium Hexafluorophosphate (PyDAOP)

To a mixture of 0.2462 g (1.5 mmol) of HODhat, prepared as in Example 4 and 0.24 ml (1.65 mmol) of TEA in 10 ml of dry CH$_2$Cl$_2$ at 0° C., 0.6993 g (1.5 mmol) of PyBrOP (tris(pyrrolidino)bromophosphonium hexafluorophosphate) was added portion wise with stirring under an atmosphere of dry N$_2$. Stirring was continued for 1 hour in an ice-bath and then at room temperature overnight. The clear light yellow mixture was diluted with CH$_2$Cl$_2$ to 25 ml and the solution washed with ice cold water (2×10 ml) and dried over MgSO$_4$. The resulting light yellow clear solution was treated with 50 ml of ether and the solid which separated was collected by filtration to give 0.45 g (54%) of analytically pure PyDAOP as a white solid after recrystallization from MeCN-ether: mp 149° C. (dec.); $^1$H NMR (CD$_3$CN): δ 9.20 (dd, 1H), 8.67 (dd, 1H), 8.13 (dd, 1H), 3.42 (td, 12H, 6NCH$_2$), 1.96 (td, 12H, 6CH$_2$); IR (KBr): 2982 (m), 2893 (m), 1742 (vs, CON), 1566 (m), 1462 (sh, w), 1270 (s), 1224 (s), 1140 (s), 1110 (s), 1049 (sh, m), 960 (s), 839 (sh, vs) cm$^{-1}$.

Anal. Calcd for C$_{18}$H$_{27}$N$_7$O$_2$P$_2$F$_6$: C, 39.34; H, 4.95; N, 17.84.

Found: C, 39.36; H, 5.09; N, 17.90.

EXAMPLE 13

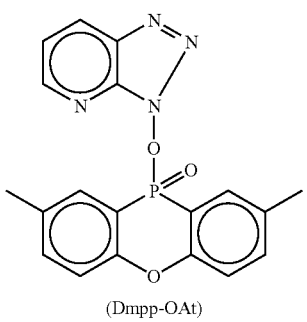

(Dmpp-OAt)

Method A. To a suspension of 0.42 g (3.054 mmol) of HOAt in 20 mL of anhydrous CH$_2$Cl$_2$, there was added 0.43 mL (1 equiv.) of triethylamine with magnetic stirring. The resulting clear yellow solution was cooled in an ice bath under an atmosphere of N$_2$ and treated slowly with 0.85 g (1 equiv.) of 2,8-dimethylphenoxaphosphinic chloride.

The reaction mixture was stirred at 0° C. for 30 min, then at room temperature for 2 hours. After dilution with 30 mL of CH$_2$Cl$_2$, the organic phase was washed with H$_2$O, saturated aqueous NaCl (30 mL) and dried over MgSO$_4$. After removal of solvent with a rotary evaporator with the aid of a water aspirator, the residue was recrystallized from CH$_2$Cl$_2$-hexane to give 0.65 g (56.3%) of the above-identified phosphinic ester as white crystals, mp 164-166° C. (dec); $^1$H-NMR (200 MHz, CDCl$_3$) δ 2.472 (s, 6), 7.218-7.559 (m, 5), 8.056-8.130 (d, 2), 8.319-8.368 (d, 2), 8.319-8.368 (d, 1), 8.698-8.729 (d, 1). IR (KBr): 1128-(P=O). Anal. Calcd for C$_{19}$H$_{15}$N$_4$PO$_3$: C, 60.32; H, 4.0; N, 14.81. HREIMS: M+ 378.0882; Found: 378.0877.

Method B: To a suspension of 1.25 g of HOAt in 20 mL of anhydrous CH$_2$Cl$_2$ there was added 0.623 g (1 equiv.) of imidazole with magnetic stirring. The resulting white suspension was cooled in an ice bath under an atmosphere of N$_2$ and treated slowly with 2.56 g (1 equiv.) of 2,8-dimethylphenoxaphosphinic chloride. The reaction mixture was stirred at 0° C. for 30 min, then at room temperature for 2 hours and diluted with 30 mL of CH$_2$Cl$_2$. The reaction mixture was filtered in a sintered glass funnel over anhydrous MgSO$_4$ under an atmosphere of N$_2$. After removal of solvent with a rotary evaporator with the aid of a water aspirator, the residue was recrystallized from CH$_2$Cl$_2$-hexane to give 2.86 g (82.3%) of the above-identified phosphinic ester as white crystals, for which the mp and NMR data agreed with the data reported above.

EXAMPLE 14

Using the procedure described hereinabove, the following are also prepared:

1.

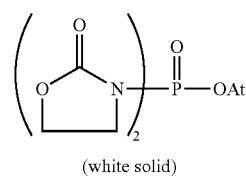

(white solid)

2. OAt derivatives of

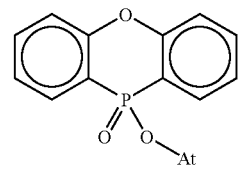

wherein the phenoxophosphinic acid products have the following substituents therein.

| |
|---|
| (a) 2,8-dibromo |
| (b) 2,8-dichloro |
| (c) 2,8-difluoro |
| (d) 2,8-dimethoxy |
| (e) 2,3,7,8-tetramethyl |

EXAMPLE 15

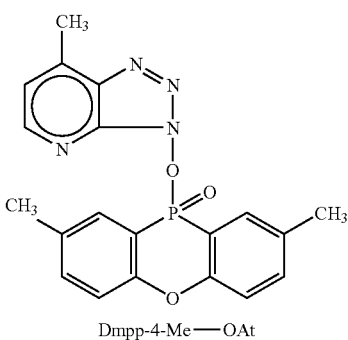

Dmpp-4-Me—OAt

Using method B of Example 14, and using 4-Me-HOAt instead of HOAt, the above-identified compound was made as a white solid.

EXAMPLE 16

Di-o-tolyl-phosphinyloxy-7-azabenzotriazole (DtpOAt)

A. Di-o-toylphosphine oxide. Magnesium turnings (13.96 g) were added to 100 ml of anhydrous ether in a 3-neck flask fitted with a condenser, magnetic stirrer and a dropping funnel kept under an atmosphere of nitrogen. o-Bromotoluene (100 g, 0.579 mol) in 100 ml of ether was slowly added to the mixture. During the addition, the Grignard reaction was initiated and became so vigorous that ice bath cooling was needed frequently. After the addition was complete (40 min), the reaction mixture was refluxed for 15 min and then cooled with an ice bath and treated slowly with 30.8 ml (0.232 mol) of diethyl phosphite in 40 ml of ether. The mixture was refluxed again for 15 min and cooled with an ice bath. Two hundred and fifty milliliters of 10% HCl and 200 ml of water were added slowly to the cooled mixture with magnetic stirring. Ether was evaporated and the insoluble phosphine oxide was collected by filtration and recrystallized from $CH_2Cl_2$-hexane (a few drops of methanol may be added to help dissolve the solid) to give 39.47 g (73.9%) of the phosphine oxide as a pale yellow solid: mp 94° C., lit. mp 93-94° C., yield 57%; $^1$H-NMR (60 MHz, $CDCl_3$): δ 2.376 (s, 6), 4.234 (s, 1), 7.19-7.94 (m, 8); IR (KBr): 2369 (P—H), 1168 (P=O) $cm^{-1}$.

B. Di-o-toylphosphinic acid. A suspension of 15.04 g of di-o-toylphosphine oxide in 80 ml of 5N aqueous NaOH was treated with 40 ml of 30% $H_2O_2$ all at once and the resulting mixture was heated on a steam-bath for 20 min. A clear solution resulted and was filtered while hot. The filtrate was cooled in an ice bath and acidified slowly with concentrated HCl, which caused the precipitation of a white solid which was recrystallized from MeOH-ether to give 13.4 g (83.3%) of the phosphinic acid: mp 174-176° C., lit. 175-177° C., yield 58-74%; $^1$H-NMR (60 MHz, TEA): δ 2.369 (s, 6), 7.245-8.124 (m, 8); IR (KBr): 1143 (P=O) $cm^{-1}$.

C. Di-o-tolylphosphinic acid chloride (DtpCl). Di-o-tolylphosphinic acid (13.5 g) was slowly added to 50 ml of thionyl chloride with cooling in an ice bath. The mixture was refluxed under a $CaCl_2$ drying tube for 3 hours. After removal of excess thionyl chloride by a water aspirator in a hood, the oily residue was fractionally distilled to give 13.55 g (93.4%) of the phosphinic acid chloride as a colorless oil (bp 158-165° C./0.1 mmHg) which solidified quickly, lit. bp 150-160° C., yield 80.5%; $^1$H-NMR (60 MHz, $CDCl_3$): δ 2.449 (s, 6), 7.05-8.08 (m, 8): IR (KBr): 1220 (P=O) $cm^{-1}$.

EXAMPLE 17

Di-o-tolyl-phosphinyloxy-7-azabenzotriazole (DtpOAt)

The above-identified compound was prepared according to the following scheme which is a variation of the procedure of Example 16:

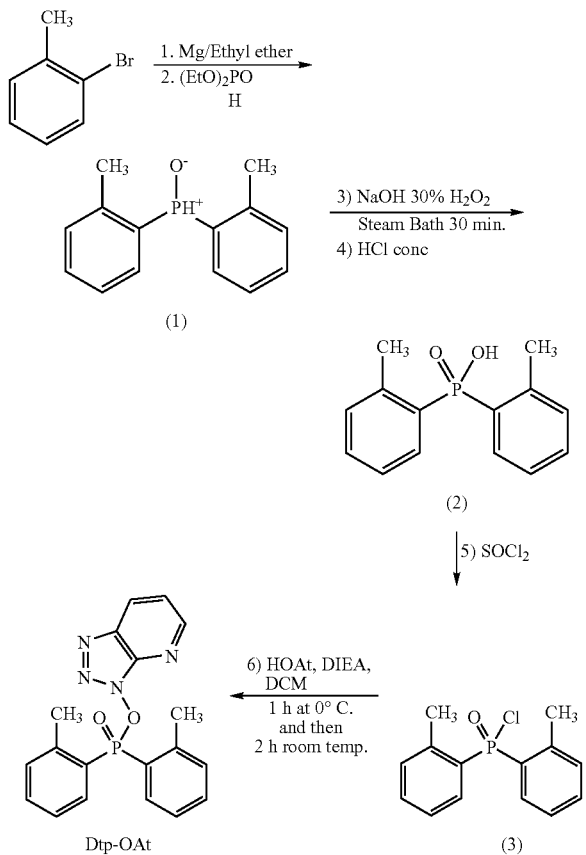

A. Preparation of Di-o-tolylphosphine oxide (1) Magnesium turnings (13.96 g) were added to 100 mL of anhydrous ether under a nitrogen atmosphere in a 1 L 3-neck flask fitted with an efficient condenser, magnetic stirrer and two dropping funnels. o-Bromotoluene (72 mL) was added to the mixture. The rate of addition was adjusted to allow the ether to boil slowly. No ice bath cooling was necessary during addition. After the addition was completed the reaction mixture was refluxed for 2 hours and then cooled in an ice bath. Diethyl phosphite (30.8 mL) in 50 mL of ethyl ether was added from the second dropping funnel and the reaction mixture was stirred at room temperature overnight. Diethyl phosphite was distilled before use, bp 62-64° C. (5 mm Hg). Two hundred and fifty milliliters of 10% HCl and 200 mL of water were added slowly to the cooled mixture and the ether was removed with a rotavap. The insoluble material was isolated by filtration, dried and recrystallized from toluene to give 30.7 g (57.4%) of the phosphine oxide as pale yellow crystals, mp 95-97° C., lit. mp 94-95° C.

B. Preparation of di-o-tolylphosphinic acid (2)—Di-o-tolylphosphine oxide (15 g) and 80 mL of 5 N NaOH were treated with 40 mL of 30% $H_2O_2$. The suspension was heated gently on a steam bath for 20 min. The heating was conducted carefully because the reaction could potentially be violent. Carrying out the reaction in a large beaker avoided loss of product if the reaction became violent. (The reaction mixture doesn't explode but a lot of foam and gas are developed.) The hot reaction mixture was added to an iced HCl solution (90 mL of conc. HCl plus 30 g of ice). The resulting white solid was isolated by extraction with chloroform (3×75 mL). The chloroform layer was washed with water and dried over magnesium sulfate. After the solvent was removed in vacuum the resulting solid was recrystallized from 95% ethanol. The above amount of phosphine oxide was oxidized in two batches of 15 g each. The average yield of the two runs was 79% for the pure phosphinic acid, mp 174-175° C., lit mp 175-177° C.

C. Preparation of di-o-tolylphosphinic acid chloride (3). Di-o-tolylphosphinic acid (22.5 g) was added in one portion to 75 mL of thionyl chloride and the reaction mixture heated under reflux for 3 hours. After removal of excess thionyl chloride, the residual oil was dissolved in dry dichloromethane (DCM), and the DCM removed at the rotavap, the operation being repeated three times. The acid chloride which was obtained as an oil which solidified upon standing was used without further purification.

D. Preparation of Dtp-OAt—To a suspension of 12.7 g of HOAt in 300 mL of anhydrous DCM was added 16.7 mL of DIEA. The resulting clear yellow solution was cooled in an ice bath under an atmosphere of nitrogen and treated with 25.8 g of di-o-tolylphosphinic acid chloride dissolved in 300 mL of DCM. The reaction mixture was stirred at 0° C. for 1 hour and then at room temperature for 2 hours. The reaction mixture was diluted with 600 mL of DCM and washed with water and saturated aqueous NaCl and dried over $MgSO_4$. After removal of solvent with a rotary evaporator with the aid of a water aspirator, the residue was recrystallized from $CH_2Cl_2$/ethyl acetate to give 30.1 g (88%) of the active ester as white crystals, mp 175-177° C., lit. mp 170-172° C.

It was noted that this material has very low solubility in DMF. Some automatic peptide synthesizes, for example, the AIB 433 A peptide synthesizer, requires a solution of the activator in DMF to be placed in one of the reagent bottles which then delivers the activated species to the reaction vessel. The concentration of the reagent in solution has to be in the range of 0.3-0.8 M to guarantee the right concentration of the active species. Since the solubility of this reagent is so low in DMF, the yield for coupling two amino acids to form a peptide was low if this automatic synthesizer was used. However, a slight modification of the structure of the product of this example to make it soluble in DMF enhances its ability to couple amino acids to form peptides. The following example illustrates a structural modification of Dtp-OAt which dramatically enhances its solubility in DMF and other organic solvents.

EXAMPLE 18

5-t-Bu-Dtp-Oat

The new coupling reagent was synthesized according to the strategy outlined hereinbelow. Starting from the commercially available 4-t-Bu-toluene the synthesis is completed in 5 steps.

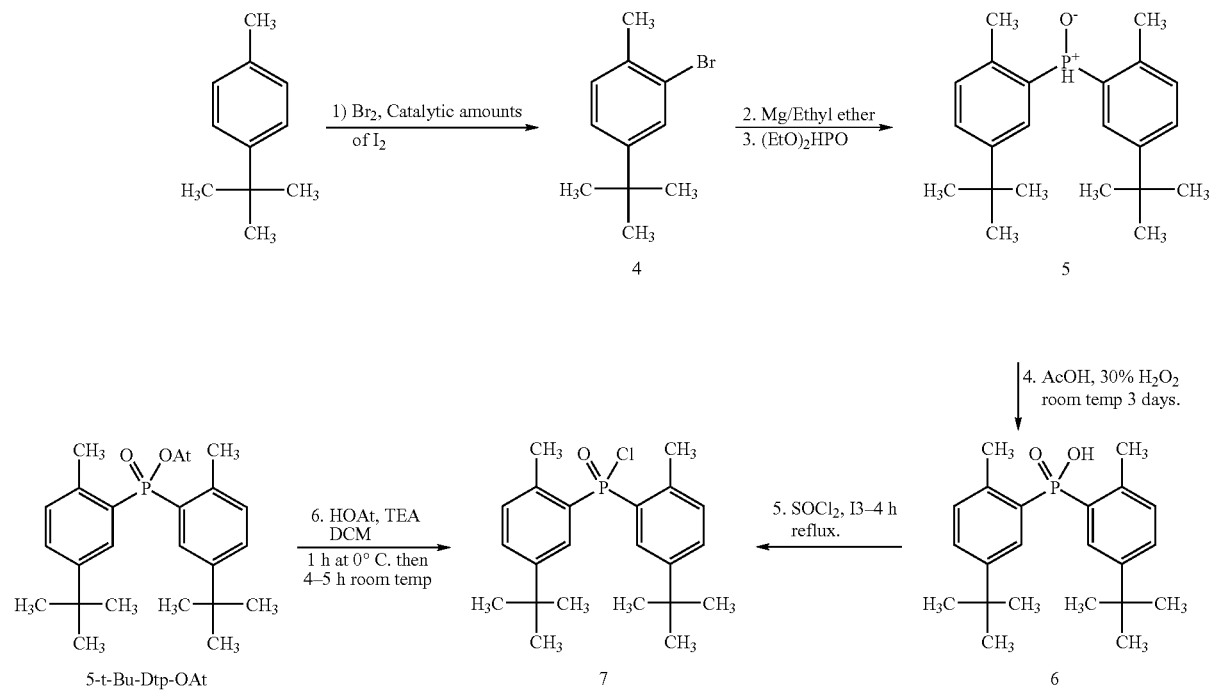

Scheme 2

A. Preparation of 2-bromo-4-t-butyltoluene (4). The bromination was carried-out according to the procedure of Reich, et al. *J. Med. Chem.* 1996, 39, 2781, the contents of which are incorporated by reference. To a solution of 4-t-butyltoluene (90 mL, 0.518 mol) and two crystals of $I_2$ was added dropwise bromine (27 mL, 0.524 mol). The reaction mixture was stirred at room temperature for 3 hours and then poured into 1 L of cold water. The mixture was transferred to a separatory funnel and the lower layer was collected. The crude 2-bromo-4-t-butyltoluene was washed with saturated $NaHCO_3$, brine and dried over $MgSO_4$. The crude product was distilled under reduced pressure, first using a water aspirator and then with a high vacuum oil pump. A first fraction was collected up to b.p. 100° C. with the aid of the water aspirator and the residue was distilled in high vacuum to give 90.5 g (77%) of the bromide as a colorless liquid, bp 61-65° C. (3-5 mm/Hg).

B. Preparation of bis-(5-t-butyl-2-methylphenyl)phosphine oxide (5). This compound was obtained according to the procedure described for compound 1, described in Example 17. The phosphine oxide (5) was recrystallized from DCM/Hexane to give 15.8 g (32%) of the oxide as white crystals, mp 178-180° C.; $^1$H-NMR (400 MHz, $CDCl_3$) δ 1.317 (18H, s), 2.334 (6H, s), 7.715 (2H, dd), 7.480 (2H, dt), 7.779 (2H, dd), 8.215 (1H, d, $J_{P-H}$ 474 Hz). IR (KBr) 2336 (PH), 1187 and 1168 cm$^{-1}$ (P=O) Anal. Calcd for $C_{22}H_{31}OP$: C, 77.16; H, 9.12. Found: C, 77.21; H, 8.98.

C. Preparation of bis-(5-t-butyl-2-methylphenyl)phosphinic acid (6). To a solution of bis-(5-t-butyl-2-methylphenyl)phosphine oxide (6 g, 17.5 mmol) in 60 mL of acetic acid was added slowly 15 mL of 30% $H_2O_2$. The reaction mixture was stirred at room temperature for three days and then poured into 300 mL of cold water. The white precipitate was isolated by filtration and recrystallized from ethanol/water to give 6 g (95%) of pure acid (6) as white crystals, mp 182-183° C.; $^1$H-NMR (400 MHz, DMSO-$d_6$) δ 1.230 (18H, s), 2.172 (6H, s), 7.034-7.902 (6H). IR (KBr) 1162 cm$^{-1}$ (P=O) Anal. Calcd for $C_{22}H_{31}O_2P$: C, 73.72; H, 8.72. Found: C, 74.00; H, 9.01.

D. Preparation of bis-(5-t-butyl-2-methylphenyl)phosphinic chloride (7). The preparation was carried out as described for compound (3) as described in Example 17. The acid chloride was used in the next step without purification. $^1$H-NMR (400 MHz, $CDCl_3$) δ 1.276 (18H, s), 2.384 (6H, s), 7.173-7.213 (2H, m), 7.493 (2H dt), 7.903 (2H, dd), IR (KBr) 1231 cm$^{-1}$ (P=O).

E. Preparation of bis-(5-t-butyl-2-methylphenyl)phosphinyloxy-7-azabenzotriazole. To a suspension of 0.76 g (5.58 mmol) of HOAt in 30 mL of anhydrous DCM was added 0.78 mL (5.6 mmol) of TEA. The resulting clear yellow solution was cooled in an ice bath under an atmosphere of nitrogen and treated with 2 g (5.27 mmol) of bis-(5-t-butyl-2-methylphenyl)-phosphinic acid chloride dissolved in 20 mL of DCM. The reaction mixture was stirred at 0° C. for 1 hour and then at room temperature for 45 hours. The reaction mixture was diluted with 40 mL of DCM and washed with water and saturated aqueous NaCl and dried over $MgSO_4$. The solvent was removed with a rotary evaporator with the aid of a water aspirator. The above product was obtained as a white solid [2.3 g (86%)] after recrystalization from hexane and then from hexane containing a small amount of ethyl acetate: mp 86-87° C., $^1$H-NMR (400 MHz, $CDCL_3$) δ 1.271 (18H, s), 2.687 (6H, s), 7.264-7.298 (2H, m), 7.369 (1H, dd), 7.545 (2H dt), 7.974 (2H, dd), 8.309 (1H, dd), 8.729 (1H, dd). IR (KBr) 1242 cm$^{-1}$ (P=O) HRFAB MS for $C_{27}H_{34}N_4O_2P$, M$^+$ 477.2419, found 477.2400.

Small-scale solubility tests showed that this compound (t-Bu-Dtp-OAt) was highly soluble in DMF and thus could be used in the automated peptide synthesizer.

As indicated hereinabove, without wishing to be bound, it is believed that during peptide coupling using uronium or phosphonium salts, the N-protected carboxylic acid first reacts with the coupling reagent to form an active ester, which then reacts with the amino component to give the corresponding amide. Therefore, the speed of formation of such an active ester is one of the important factors in evaluating the efficiency of the coupling reagent. The model chosen hereinbelow involved conversion of N-benzyloxycarbonyl-α-aminoisobutyric acid (CBZ-Aib-OH) to the corresponding active ester in both DMF and $CDCl_3$, as described in the chemical equation hereinbelow.

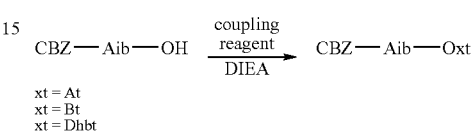

xt = At
xt = Bt
xt = Dhbt

In the study, a comparison was made with derivatives of HOBt, HOAt with HODhbt:

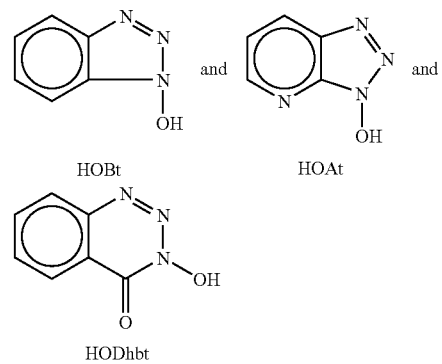

The benzylic $CH_2$ units of CBZ-Aib-OH (55.09) and active ester (65.20) were monitored by NMR. Assignment of the peak at 65.20 in the active esters was confirmed by authentic synthesis.

Because of the sterically hindered carboxyl group of Aib, activation in the above equation is slow relative to the case of the proteinogenic amino acids allowing different coupling reagents to be more closely differentiated.

The procedure is described in Example 19 hereinbelow.

EXAMPLE 19

(a) Di-o-tolylphosphinyloxybenzotriazole (DtpOBt). The preparation was carried out similarly to that as described for preparing the product of Example 16: HOBt (0.125 1 g, 1 mmol) was treated with Dtp-Cl (0.267 g, 1 mmol) in the presence of DIEA (0.21 ml, 1.2 mmol) for 5 hours in 10 ml of dry $CH_2Cl_2$ to give 0.24 g (66%) of white solid after work-up. Recrystallization from $CH_2Cl_2$-hexane gave 0.18 g of an analytically pure sample of the ester as colorless crystals: mp 198-200° C.; $^1$H-NMR ($CDCl_3$): δ8.06 (m, 3), 7.30 (m, 6), 2.62 (s, 6); IR (KBr): 3065 (W), 1593 (s), 1457 (s), 1362 (m), 1278 (m), 1230 (vs), 1151 (s), 1084 (sh, s), 812 (vs), 774 (sh, vs), 704 (m) cm$^{-1}$. Anal. Calcd for $C_{20}H_{18}N_3O_2P$: C, 66.10; H, 4.92; N, 11.56. Found C, 65.75; H, 4.97; N, 11.41.

(b) 3-[di-o-tolyl)phosphinyloxy]-3,4-dihydro-4-oxo-2,3 benzotriazine] (DtpODhbt) was made according to method A described for DmppOAt (Method A) in Example 14 using HODhbt, which was prepared similarly to the method described in Ex. 4 using HOBt instead of HOAt and using di-o-tolylphosphinic chloride. The product was obtained as white crystals (76.5%) after recrystallization from ethyl acetate-ether: mp 178-179° C. (dec); $^1$H-NMR (200 MHz, CDCl$_3$): δ2.58 (s, 6), 7.28 (m, 4), 7.487-7.570 (m, 2), 7.75 (m, 1), 7.90-8.15 (m, 4), 8.351 (dd, 1); IR (KBr): 1709 (C=O), 1240 (P=O) cm$^{-1}$. Anal. Calcd for C$_{21}$H$_{18}$N$_3$PO$_3$; C, 64.45; H, 4.64; N, 10.74. Found: C, 64.49; H, 4.54; N, 10.69.

(c) Active Ester Formation. To a solution of 0.1 mmol of CBZ-Aib-OH and 0.1 mmol of the appropriate coupling reagent in 0.5 ml of CDCl$_3$ or DMF, was added 0.1 mmol of DIEA. The mixture was immediately transferred to an NMR tube which was placed in the probe of a Hitachi R-1200 (60 MHz) NMR instrument. Integration of the $^1$H-NMR peaks at δ5.1 (acid) and 5.2 (active ester) as the reaction progressed at the probe temperature (37° C.) allowed for rough determination of the relative rates. The results are given in Table 1 and represent the averages of at least two runs.

| Coupling Reagent | $t_{1/2}$ (DMF), min | $t_{1/2}$ (CDCl$_3$), min |
|---|---|---|
| DEPOAt | <2 | 2–3 |
| DPOPOAt | <2 | 2–3 |
| DEPDBt | 7–8 | 45–47 |
| DPOPDBt | <2 | <2 |
| DtpOBt | 65–70 | 11–12 h |
| N-HATU | <2 | 14–15 |
| N-HAPyU | <2 | <2 |
| HDTU | <2 | <2 |
| N-HBTU | <2 | >24 h |

In the examples that follow, it is to be understood that the amino acid sequence is presented in the amino to carboxy direction, from left to right.

EXAMPLE 20

To test for configuration control, three different peptides, CBZ-Phe-Val-Pro-NH$_2$, CBZ-Gly-Phe-Pro-NH$_2$, and CBZ-Gly-Gly-Val-Ala-Gly-Gly-OMe (SEQ ID NO:1) were prepared and the loss of configuration during the coupling was determined. An exemplary procedure is given for a dipeptide as follows:

A. CBZ-Phg-Pro-NH$_2$ As a standard protocol, 35.6 mg (0.125 mmol) of CBZ-Phg-OH, 14.3 mg (0.125 mmol) of H-Pro-NH$_2$, and 0.25 mmol of base in 1 ml of DMF or other solvent was treated with 0.125 mmol of an appropriate coupling reagent at 0° C. The mixture was stirred at 0° C. for 1 hour and at room temperature overnight. The resulting mixture was diluted with 25 ml of EtOAc and washed with HCl (2×10 ml), 10% NaHCO$_3$ solution (2×10 ml) and brine (2×10 ml), and dried over MgSO$_4$. An oily peptide residue was obtained after removing solvent. The oily residue was redissolved in 1 ml of CH$_2$Cl$_2$ and 20 ml of hexane was added. A white solid was obtained after filtration. About 5 mg of this crude product, usually containing both LL- and DL-forms of CBZ-Phg-Pro-NH$_2$, was dissolved in 4 ml of MeCN and directly analyzed by HPLC as described in Wenschuh, et al., *J. Org. Chem.*, 1995, 62, 405, the contents of which are incorporated by reference.

B. CBZ-Phe-Val-Pro-NH$_2$. The standard protocol as described above for CBZ-Phg-Pro-NH$_2$ was followed.

C. CBZ-Gly-Phe-Pro-NH$_2$. The standard protocol as described above for CBZ-Phg-Pro-NH$_2$ was followed.

D. CBZ-Gly-Gly-Val-Ala-Gly-Gly-OMe (SEQ ID NO 1.) As described for CBZ-Phg-Pro-NH$_2$, a solution of 45.6 mg (0.125 mmol) of CBZ-Gly-Gly-Val-OH, 31.7 mg (0.125 mmol) of H-Ala-Gly-Gly-OMe.HCl and 49.6 μl (0.375 mmol) of TMP in 1 ml of DMF was treated with 0.125 mmol of an appropriate coupling reagent at 0° C. The resulting mixture was stirred at 0° C. for 1 hour and then at room temperature overnight. The crude hexapeptide methyl ester was isolated by evaporation of solvent followed by direct column chromatography using MeOH/CHCl$_3$/HOAc (3:7: 0.1) as eluate. The crude material from the column, containing both LL- and DL-forms of hexapeptide, was examined by HPLC as described in Carpino, *J. Org. Chem.*, 1994, 59, 695, the contents of which are incorporated by reference.

The results are given in Table 2

TABLE 2

Effect of Coupling Reagent on Loss of Configuration During [2 + 1] Coupling Leading to CBZ-Phe-Val-Pro-NH$_2$, CBZ-Gly-Phe-Pro-NH$_2$ and [3 + 3] Coupling Leading to CBZ-Gly—Gly-Val-Ala-Gly—Gly-OMe in DMF with 2 eqs. TMP as base.

| Coupling Reagent | CBZ-Phe-Val-Pro-NH$_2$ | CBZ-Gly-Phe-Pro-NH$_2$ | CBZ-Gly—Gly-Val-Ala-Gly—Gly-OMe |
|---|---|---|---|
| DEPOAt | 0.9 (0.9) | <0.1 | <0.1 |
| DmppOAt | 3.6 (2.0) | 0.3 | |
| DtpOAt | 2.9 (1.4) | 0.4 | |
| N-HATU | 5.0 (1.8) | 1.1 (0.9) | 2.4 |
| DEPDBt | 3.5 | 0.3 | 2.4 |
| DtpODhbt | 4.3 (3.6) | | |
| HDTU | 8.5 (4.0) | | 3.3 |
| DtpOBt | 11.4 | 2.2 | |
| N-HBTU | 14.2 | 3.6 | 8.2 |

$^a$Figures in parenthesis refer to identical runs but with 1 eq. of the appropriate HOXt e.g., HOAt, HOBt or HODhbt added.

As confirmed by the data herein, the new phosphorous-based OAt derivatives of the present invention are much more effective in preserving configuration than any of the other tested reagents, including N-HATU. The best of the previously-described uronium/guanidinium salts (N-HAPyU) sometimes equals the results of the new phosphorus esters, but where differences are observed, the latter have proved more effective in every case examined to date.

Among the results obtained from these data involving N-HAPyU, it was found that for the new reagents DEPOAt and DPOPOAt, a one-equivalent excess of proline serving as base gave the lowest epimerization levels yet observed for the tripeptide CBZ-Phe-Val-Pro-NH$_2$ in DMF (0.5% LDL-isomer). Upon switching to other solvents, even greater differences were found between the new phosphorus reagents of the present invention and the related uronium/guanidinium salts. For example, in the special structure-breaking combination solvent trifluoroethanol/trichloromethane (TFE, TCM, 1:3), 12.2% of the LDL-form was obtained for DPOPOAt/TMP as opposed to 38.5% for N-HATU/TMP. In CH$_2$Cl$_2$ in the presence of TMP, 2.2% (DEPOAt) and 2.9% (DPOPOAt) were clearly better than values observed for guanidinium reagents N-HATU (9.3%) and N-HAPyU (5.3%).

In order to determine the coupling efficiency of diphenyl phosphorochloridate (DPOPCl) various coupling conditions were used. It was noted that without additive, DPOPCl gave only a very small amount of the desired peptide for both diisopropylethylamine and trimethylpyridine. If one equivalent of HOAt (1-hydroxy-7-azabenzotriazole) was present, the results were acceptable. Indeed the mixture DPOPCl/

HOAt/Base, which contains DPOPOAt as the active species, gave results which are comparable to those obtained with the isolated reagent DPOPOAt.

The Tripeptide CBZ-Phe-Val-Pro-NH$_2$ was also chosen as a model to study loss of configuration associated with use of various reagents of the present invention under solid phase conditions. In comparison with results obtained in solution, the data show how much more difficult it is to maintain configuration in the solid phase mode. The system involved overnight coupling of four equivalents of CBZ-Phe-Val-OH onto H-Pro-PAL-PEG-PS in the presence of 8 eqs. of trimethylpyridine in DMF, cleavage of the tripeptide from the resin via trifluoroacetic acid/H$_2$0 (9:1) over a period of 1 hour and separation of the diastereomers as described for the solution system. Although extensive loss of configuration occurs in all cases, the data show that the effectiveness of the various coupling reagents follows the same order as in solution, thus coupling reagent/LDL (%): DEPOAt/11.6, N-HAPyU/13.0, N-HATU/13.6, DPOPODBt/19.4, DEPDBt/19.5, HDTU/24.2, N-HBTU/29.8.

EXAMPLE 21

ACP Assembly Via Stepwise Coupling on Solid Phase

In order to demonstrate the suitability of the organophosphorus-based coupling reagents and compare their performance with that of the corresponding uronium/guanidinium analogs in solid phase syntheses, several syntheses of the ACP decapeptide segment 65-74 (H-Val-Gln-Ala-Ala-Asp-Tyr-Ile-Asn-Gly-NH$_2$) (SEQ ID NO:2) were carried out.

The protocol is as follows: 150 mg of Fmoc-Gly-PAL-PEG-PS resin (0.19 mmol/g, 0.0285 mmol) in a 10-ml disposable syringe fitted with a Teflon filter was washed with CH$_2$Cl$_2$ (3×10 ml) and DMF (3×10 ml) and deprotected with 20% piperidine in DMF (10 ml) for 7 min. The deprotected resin was washed with DMF (3×10 ml), CH$_2$Cl$_2$ (3×10 ml) and again DMF (3×10 ml). Preactivation was carried out for 7 min using 25.5 mg (0.04 mmol, 1.5 equiv) of Fmoc-Asn (Trt)-OH, 15.75 mg (0.04 mmol, 1.5 equiv) of DPOPOAt and 14.89 µl (0.09 mmol, 3 equiv) of DIEA (diisopropylethylamine) in 0.15 ml of DMF in a 4-ml vial. Following the requisite preactivation period (7 min), the solution of the activated amino acid was added to the resin. The small vial was washed with 0.04 ml of DMF, and the washing was also added to the above resin. The resulting resin mixture was allowed to react at room temperature for 1.5 min. The loaded resin was washed with DMF (3×10 ml) and the Fmoc group was deblocked with 10 ml of 20% of piperidine in DMF for 7 min. Washing the deblocked resin with DMF (3×10 ml), CH$_2$Cl$_2$ (3×10 ml) and DMF (3×10 ml) was followed by an analogous coupling step with Fmoc-Ile-OH. Other amino acids were coupled similarly and after the last coupling with Fmoc-Val-OH and deblocking of the Fmoc group with 20% piperidine in DMF, the loaded resin was washed with DMF (3×10 ml), CH$_2$Cl$_2$ (3×10 ml), EtOH (5 ml) and ether (5 ml). The resin was then treated with 10 ml of 90% aqueous trifluoroacetic acid for 2 hours, filtered, and washed on the filter with 10 ml of 10% trifluoroacetic acid in CH$_2$Cl$_2$ and 10 ml of CH$_2$Cl$_2$. The combined filtrates were evaporated to dryness. The crude product was washed four times with anhydrous ether and separated by centrifugation. The yield was calculated by the weight of the crude product. For analysis 1 mg of the crude product was dissolved in 1 ml of 0.1% aqueous trifluoroacetic acid and injected directly onto the HPLC column for analysis. The procedure was repeated using the same coupling agent until the peptide of SEQ ID NO. 2 SEQ ID NO:2 was prepared.

This procedure was repeated using each of the coupling agents listed in Table 3 for the preparation of the peptide of SEQ. ID. NO. 2 SEQ ID NO:2. The results are given in Table 3.

TABLE 3

Distribution of Products, Including Various Deletion Peptides, According to HPLC Analysis for the Assembly of ACP (65–74) via HOAt- and HODhbt-Based Coupling Reagents

| Entry | Coupling Method | Equiv. of Reagents | Preactivation Time (mm) | Coupling (min) | ACP (%) | -2Ile (%) | -Ile72 (%) | -Ile69 (%) | -Val (%) | -Ala (%) | -Asn (%) |
|---|---|---|---|---|---|---|---|---|---|---|---|
| 1 | DEPOAt | 1.5 | 7 | 1.5 | 84 | — | 2 | 2 | 1 | 4 | 5 |
| 2 | DPOPOAt | 1.5 | 7 | 1.5 | 85 | — | 2 | 1 | 2 | 6 | 3 |
| 3 | DEPDBt | 1.5 | 7 | 1.5 | 6 | 9 | 13 | 19 | 3 | — | 1 |
| 4 | DPOPOBt | 1.5 | 7 | 1.5 | 23 | 21 | 26 | 19 | 1 | 1 | 2 |
| 5 | N-HATU | 1.5 | 7 | 1.5 | 85 | — | 1 | 1 | 3 | — | 10 |
| 6 | HDTU | 1.5 | 7 | 1.5 | 38 | 15 | 15 | 26 | — | — | 5 |
| 7 | DEPOAt | 1.5 | 0 | 1.5 | 86 | — | 4 | 2 | 2 | 3 | 1 |
| 8 | DPOPOAt | 1.5 | 0 | 1.5 | 81 | — | 4 | 1 | 1 | 7 | — |
| 9 | DEPDBt | 1.5 | 0 | 1.5 | <1$^c$ | — | — | — | — | — | — |
| 10 | DPOPOBt | 1.5 | 0 | 1.5 | 29 | 17 | 25 | 17 | 2 | — | 3 |
| 11 | N-HATU | 1.5 | 0 | 1.5 | 87 | — | 3 | 1 | 2 | — | 6 |
| 12 | HDTU | 1.5 | 0 | 1.5 | 30 | 15 | 19 | 22 | 3 | — | 4 |

*A reversed-phase C-18 column was used with elution by a linear gradient over 20 mm of 0.1% TFA in MeCN and 0.1% TFA from 1:19 to 1:1, flow rate 1.0 ml/mm.
$^b$ Couplings were carried out in DMF in the presence of 2 equivalents of diisopropylethylamine per equivalent of Fmoc-amino acid/coupling reagent.
$^c$Only a trace of the desired product was obtained.

In this experiment, coupling times are shortened and excesses of reagents are reduced in order to bring out differences among the various reagents studied. Under these conditions, incomplete incorporations were detected for Asn onto Gly, Ile onto Asn, Ile onto Asp, Val onto Gln and Ala onto Ala or Asp. Analysis of the chromatograms indicated that the new HOAt-based organophosphorus reagents are as effective as N-HATU under these so-called "1.5×1.5" conditions with or without preactivation. Under normal coupling conditions such as 4 eqs excess amino acid/30 min. coupling time, all reagents worked well with the exception of HDTU.

EXAMPLE 22

In the following example, reactions of the hindered active esters CBZ-Aib-OXt with p-chloroaniline (PCA) were studied in CDCl$_3$. Approximate halftimes were determined by proton NMR analysis according to the disappearance of the benzylic CH$_2$ unit (δ 5.2) of the active esters and appearance of the benzylic CH$_2$ residue (δ 5.5) of the product.

CBZ-Aib-OXt Esters. The reaction of Z-Aib-ODhat with PCA is taken as an example to demonstrate the standard method used in order to follow aminolysis via an NMR protocol: To a solution of 47.9 mg (0.125 mmol) of CBZ-Aib-ODhat in 0.5 ml of CDCl$_3$, was added 15.6 mg (0.125 mmol) of p-chloroaniline (PCA). The mixture was immediately transferred to an NMR tube, which was placed in the probe of a Hitachi R-1200 (60 MH$_z$) instrument. Integration of the $^1$H NMR peaks at δ 1.8 (CH$_3$ residue of ester CBZ-Aib-ODhat) and 1.57 (CH$_3$ residue of amide CBZ-Aib-PCA) [or peaks at δ5.2 (benzylic CH$_2$ unit of ester CBZ-Aib-ODhat) and 5.05 (benzylic CH$_2$ unit of the product amide)] as the reaction progressed at the NMR probe temperature (37° C.) allowed for rough determination of the relative rates. The results given in Table 4 are the average of at least two runs.

TABLE 4

Approximate Halftimes for Disappearance of CBZ-Aib-OXt in CDCl$_3$ in the Presence of p-Chloroaniline

| CBZ-Aib-OXt | $t_{1/2}$ (min) |
|---|---|
| CBZ-Aib-ODhat | 8–9 |
| CBZ-Aib-OAt | 9–10 |
| CBZ-Aib-ODhbt | 12–13 |
| CBZ-Aib-ODhad | 70 |
| CBZ-Aib-OBt | 210 |

It was found that the ODhat ester is slightly more reactive even than the OAt ester, which was previously found to be the most reactive derivative among these esters. Interestingly, despite the structural similarity between HODhat, i.e., 3-hydroxy-4-oxo-3,4-dihydro-5-azabenzo-1,2,3-triazine, and HODhad, i.e., 3-hydroxy-4-oxo-3,4-dihydroxy 5-azabenzo-1,3-diazine the reactivities of the corresponding active esters are very different. Without wishing to be bound, it is believed this may be due to the presence or absence of additional neighboring group effects promoted by the presence or absence of a nitrogen atom substituted at the 2-position. On the other hand, comparison of the OBt and ODhad esters demonstrates the importance of the neighboring carbonyl group.

EXAMPLE 23

In this example, a second model was used. Pivaloyl esters in the presence of various comparative coupling agents were treated with benzylamine and N-methylbenzylamine, which led to the formation of amides of the following formula:

XXV(a): W = H, W' = benzyl
XXV(b): W = Me, W' = benzyl.

Approximate halftimes for these reactions were determined by proton NMR analysis, according to the disappearance of the methyl peak (δ 1.5) for pivaloyl-OXt and the appearance of the methyl peak for products XXV$_a$ (δ 1.2) or XXV$_b$ (δ 1.3). The protocol is as follows:

Me$_3$CCOOXt Esters. As in the case with Example 22, the reaction of pivaloyl ester with N-methyl benzylamine is taken here as an example to demonstrate the methodology used: To a solution of 31.0 mg (0.125 mmol) of Me$_3$CCOODhat in 0.5 ml of CDCl$_3$, was added 15.1 mg (16.1 µl, 0.125 mmol) of PhCH$_2$NHMe. The mixture was immediately transferred to an NMR tube, which was placed in the probe of a Hitachi R-1200 (60 MHz) instrument. Integration of the $^1$H NMR peaks at δ 1.5 (CH$_3$ residue of ester Me$_3$CCOODhat) and 1.3 (CH$_3$ residue of amide) as the reaction progressed at the NMR probe temperature (~37° C.) allowed for rough determination of the relative rates. The results given in Table 5 are the average of at least two runs.

The results are tabulated in Table 5.

TABLE 5

Approximate Halftimes for Disappearance of Me$_3$C—CO-Oxt in CDCl$_3$

| Me$_3$CCOOXt | $t_{1/2}$ (PhCH$_2$NH$_2$) | $t_{1/2}$ (PhCH$_2$NHMe)) |
|---|---|---|
| Me$_3$CCOODhat | <1 min | <2 min |
| Me$_3$CCOOAt | <1 min | 7–8 min |
| Me$_3$CCOODhbt | <1 min | 18–20 min |
| Me$_3$CCOODhad | <1 min | 35–40 min |
| Me$_3$CCOOBt | <1 min | 4.5 hr |

In the case of benzylamine all reactions were rapid whereas in the case of the more hindered N-methyl derivative, clear reactivity differences were seen according to the following order: ODhat>OAt>ODhbt>ODhad>OBt. Again the greater reactivity of the HODhat ester relative to that derived from HOAt is seen.

EXAMPLE 24

Another comparative study was run to compare relative rates of coupling processes involving the reaction of CBZ-Aib-OH with p-chloroaniline (PCA) in the presence of a coupling reagent. Because formation of intermediate Z-Aib-OXt is usually very fast, halftimes are determined by disappearance of the benzylic CH$_2$ residue (δ 5.2) of the active ester and appearance of the benzylic CH$_2$ unit (δ 5.05) of product CBZ-Aib-PCA unless otherwise noted. The protocol for the preparation of this product is the same as described in Example 23. Approximate halftimes are collected in Table 6. In this case various solvent systems were examined.

TABLE 6

Approximate Halftimes for Disappearance of [CBZ-Aib-Oxt] in Various Solvent Systems in the Presence of p-Chloroaniline

| Coupling Reagent | $t_{1/2}$ (CDCl$_3$) | $t_{1/2}$ (CD$_3$CN) | $t_{1/2}$ (DMF) | $t_{1/2}$ (DMF/CDCl$_3$)$^a$ |
|---|---|---|---|---|
| HDATU | <3 min | 70–75 min | | 30–40 min |
| N-HATU | 18–24 min | 90–95 min | 75–85 mm | 40–45 min |
| HDTU | 20–25 min | 4.5–5 hr | 6–7 hr | 2.5–3 hr |
| N-HBTU | 3.5–4 hr | | 10–11 hr$^b$ | |

$^a$1:1 mixture of DMF/CDCl$_3$.
$^b$In this case, the halftime is determined by disappearance of acid Z-Aib-OH and appearance of both intermediate active ester and amide CBZ-Aib-PCA.

Interestingly in all solvent systems examined except for DMF, the new coupling reagent was found to be more reactive than N-HATU. In $CDCl_3$, HDATU is at least six times as reactive as N-HATU and about eight times as reactive as HDTU. So far, in every case tested HDATU was shown to be significantly more reactive than HDTU.

Example 25

In order to test the configuration-retention effectiveness of the additives HODhat and HODhad, and the coupling reagents HDATU, HDADU, HDAPyU, HDPyU, PyDAOP, and PyDOP, the following model peptide systems were examined. These involve a [1+1] stepwise coupling, and three [2+1] and one [3+3] segment couplings.

```
CBZ-Phg-Pro-NH2,
XXVI

CBZ-Phe-Val-Pro-NH2,
XXVII

CBZ-Gly-Phe-Pro-NH2
XXVIII

CBZ-Gly-Gly-Val-Ala-Gly-Gly-OMe,    (SEQ ID NO 1)
XXIX
and

H-Gly-Leu-Phe-OBzl
XXX
```

Test couplings were carried out as described previously in Example 22 and in L. A. Carpino, et al., *J. Org. Chem.* 1990, 61, 2463, for CBZ-Phg-ProNH$_2$, CBZ-Phe-Val-Pro-NH$_2$, CBZ-Gly-Phe-Pro-NH$_2$ and CBZ-Gly-Gly-Val-Ala-Gly-Gly-OMe substituting the coupling reagent listed hereinbelow in the tables and the protocols therein, the results of which are incorporated by reference. For Boc-Gly-Leu-Phe-OBzl, (Bzl=benzyl) 60.6 mg (0.21 mmol) of Boc-Gly-Leu-OH, 85.45 mg (0.20 mmol) of H-Phe-OBzl.pTsOH and 0.22 mmol of an appropriate coupling additive (HOXt) were dissolved in 1 ml of DMF or trifluroethanol/trichloromethane (1:3 v/v). To the mixture, a solution of 34.2 mg (0.22 mmol) of EDC (1-ethyl-3-3'-(dimethylamino)-propyl)carbodiimide in 1 ml of DMF or trifluroethanol/trichloromethane was added and the whole mixture was stirred at room temperature overnight. The resulting mixture was diluted with 25 ml of EtOAc and washed with 1 N HCl (2×10 ml), 10% NaHCO$_3$ (2×10 ml) and brine (2×10 ml), and dried over MgSO$_4$. After removal of solvent, the solid was weighed to determine the yield. The solid was then stirred with 2 ml of 50% trifluoroacetic acid in a methylene chloride solution for 2 hours to deblock the BOC-group. The trifluoroacetic acid and CH$_2$Cl$_2$ were then removed in vacuo and 20 ml of anhydrous ether was added to the oily residue, and the mixture was stored at room temperature overnight. The white precipitate which had separated was collected by filtration and washed with ether. About 5 mg of the crude product, containing both LL- and DL-forms of XXX was dissolved in 4 ml of MeCN and directly analyzed by HPLC using a reversed-phase Waters C-18 column, with elution by a linear gradient over 20 min of 0.1% trifluoroacetic acid in MeCN and 0.1% aqueous TFA from 1:9 to 11:9, at a flow rate of 1.0 ml/min. The retention times for the LL and DL-forms of XXX were 17.3 and 17.9 min, respectively. The results are as follows:

For the sensitive coupling of the urethane-protected CBZ-Phg-OH to H-Pro-NH$_2$ to give XXVI, HDATU was more effective in preserving configuration than HDTU and N-HBTU, but not better than N-HATU. Curiously with this system, use of the base diisopropylethyl amine (DIEA) proved more satisfactory than collidine (TMP), a result that is rarely observed in the case of the corresponding segment couplings. Results are collected in Table 7.

TABLE 7

Effect of Coupling Regeant, Base and Solvent on the Preservation of Configuration during the Formation of XXVI via [1 + 1] Coupling

| Coupling Reagent (%) | Additive | Base (Eq.) | Solvent | Yield (%) | DL |
|---|---|---|---|---|---|
| HDATU | | DIEA(2) | DMF | 83.9 | 4.8 |
| HDTU | | DIEA(2) | DMF | 78.4 | 12.8 |
| N-HATU | | DIEA(2) | DMF | 71.7 | 2.8 |
| N-HBTU | | DIEA(2) | DMF | 81.3 | 6.3 |
| HDATU | | TMP(2) | DMF | 87.5 | 6.0 |
| HDTU | | TMP(2) | DMF | 80.7 | 16.0 |
| N-HATU | | TMP(2) | DMF | 90.8 | 3.8 |
| N-HBTU | | TMP(2) | DMF | 85.4 | 8.7 |
| DCC | HODhat(1) | TMP(1) | TFE/TCM[a] | 74.8 | 0.4 |
| DCC | HODhbt(1) | TMP(1) | TFE/TCM[a] | 71.8 | 0.8 |
| DCC | HOAt(1) | TMP(1) | TFE/TCM[a] | 69.2 | 0.3 |

[a]In this case, 1.3 ml of trifluoroethanol-chloroform (1:3 v/v) was used as solvent.

With carbodiimide reagents in the solvent trifluroethanol/trichloromethane, HODhat was even more effective than HODhbt. Thus, EDC/HODhat gave 0.5% of the DL-isomer, whereas EDC/HODhbt led to 1.3% of the same form. For DCC/HODhat and DCC/HODhbt in the presence of 1 equivalent of trimethylpyridine, the figures were 0.4% and 0.8%, respectively.

For the well-studied segment coupling of CBZ-Phe-Val-OH to H-Pro-NH$_2$ leading to tripeptide XXVII, the results are tabulated in Table 8.

TABLE 8

Effect of Coupling Reagent, Base and Solvent on the Preservation of Configuration during the Formation of XXVII via [2 + 1] Coupling

| Coupling Reagent | Additive | Base (Eq.) | Solvent | Yield (%) | LDL (%) |
|---|---|---|---|---|---|
| HDATU | | DIEA(2) | DMF | 85.4 | 15.1 |
| HDTU | | DIEA(2) | DMF | 81.0 | 13.3 |
| HDADU | | DIEA(2) | DMF | 72.4 | 27.6 |
| N-HATU | | | DIEA(2) | DMF | |
| N-HBTU | | | DIEA(2) | DMF | |
| HDATU | | TMP(2) | DMF | 88.8 | 8.7 |
| HDTU | | TMP(2) | DMF | 86.4 | 8.5 |
| HDADU | | TMP(2) | DMF | 83.8 | 18.6 |
| N-HATU | | | TMP(2) | DMF | 80.1 |
| N-HBTU | | | TMP(2) | DMF | 81.2 |
| HDATU | HODhat(1) | TMP(2) | DMF | 68.0 | 7.3 |
| HDTU | HODhbt(1) | TMP(2) | DMF | 65.0 | 4.0 |
| N-HATU | HOAt(1) | | TMP(2) | DMF | |

* DIEA = diisopropylethylamine; TMP = trimethylpyridine

For the rather insensitive case of the segment coupling of Z-Gly-Phe-OH to H-Pro-NH$_2$, the results paralleled those for XXVII. Results are presented in Table 9.

TABLE 9

Effect of Coupling Reagent, Base and Solvent on the Preservation of Configuration during the Formation of XXVIII via [2 + 1] Coupling[a]

| Coupling Reagent | Additive | Base Solvent (Eq.) | Solvent | Yield (%) | LDL (%) |
|---|---|---|---|---|---|
| HDATU | | DIEA(2) | DMF | 96.5 | 0.5 |
| HDTU | | DIEA(2) | DMF | 82.0 | 1.5 |
| HDADU | | DIEA(2) | DMF | 92.8 | 7.2 |
| N-HATU | | DIEA(2) | DMF | 86.0 | 0.8 |
| N-HBTU | | DIEA(2) | DMF | 84.8 | 5.9 |
| PyDAOP | | DIEA(2) | DMF | 89.9 | 0.8 |
| PyDOP | | DIEA(2) | DMF | 94.3 | 0.7 |
| HDATU | | TMP(2) | DMF | 94.1 | 1.0 |
| HDTU | | TMP(2) | DMF | 98.3 | 1.7 |
| HDADU | | TMP(2) | DMF | 86.6 | 8.4 |
| N-HATU | | TMP(2) | DMF | 96.5 | 1.1 |
| N-HBTU | | TMP(2) | DMF | 88.2 | 3.6 |
| HDAPyU | | TMP(2) | DMF | 78.8 | 1.2 |
| HDPyU | | TMP(2) | DMF | 80.9 | 1.4 |
| PyDAOP | | TMP(2) | DMF | 84.3 | 1.8 |
| PyDOP | | TMP(2) | DMF | 90.4 | 1.7 |
| HDATU | | DIEA/TMP[b] | DMF | 85.8 | 0.8 |
| HDTU | | DIEA/TMP[b] | DMF | 84.8 | 1.5 |
| N-HATU | | DIEA/TMP[b] | DMF | 76.4 | 0.9 |
| DIC(diisopropylcarbodimide) | HODhat(1) | | DMF | 86.2 | 0.5 |
| DIC | HODhbt(1) | | DMF | 81.4 | 0.8 |
| DIC | HODhad(1) | | DMF | 74.3 | 8.2 |
| DIC | HOAt(1) | | DMF | 82.3 | 0.4 |
| EDC HCl | HODhat(1) | TMP(1) | DMF | 94.0 | 1.8 |
| EDC HCl | HODhad(1) | TMP(1) | DMF | 85.2 | 2.2 |
| EDC HCl | HOAt(1) | TMP(1) | DMF | 89.3 | 3.3 |
| EDC HCl | HODhat(1) | TMP(2) | DMF | 90.1 | 2.8 |
| EDC HCl | HODhbt(1) | TMP(2) | DMF | 86.1 | 1.6 |
| EDC HCl | HOAt(1) | TMP(2) | DMF | 91.0 | 1.7 |
| EDC | HODhat(1) | | DMF | 88.8 | 3.4 |
| EDC | HODhat(1) | | TFE/TCM[c] | 80.2 | 2.5 |

[a]Abbreviations as given hereinabove.
[b]In this case, a combination of 1 equiv of DIEA and 1 equiv of TMP was used as base.
[c]1.3 ml of trifluoroethanol-chloroform was used as solvent.

For the preparation of tripeptide XXVIII, HDATU was similar to or even slightly more effective than N-HATU.

With respect to the test tripeptide XXX, the coupling of H-Phe-OBzl TosOH with Boc-Gly-Leu-OH in the presence of EDC/additive (coupling agent) in various solvents gave a product Boc-Gly-Leu-Phe-OBzl which was BOC-deblocked via 50% TFA/CH$_2$Cl$_2$ to give the crude tripeptide, which was directly analyzed by HPLC.

In the EDC-mediated synthesis of XXX carried out in trifluoroethanol/chloroform (1:3 v/v), the three additives HODhat, HODhbt, HOAt were found equally effective with less than 0.1% epimerization being observed. Upon switching to DMF as solvent, differences, although small, could be noted. Results are shown in Table 10.

TABLE 10

Effect of Coupling Reagent, Base and Solvent on the Preservation of Configuration during the Formation of XXX via [2 + 1] Coupling

| Coupling Reagent | Solvent | Yield | LDL |
|---|---|---|---|
| EDC/HODhat | DMF | 76.2 | 0.20 |
| EDC/HODhbt | DMF | 88.5 | 0.25 |
| EDC/HOAt | DMF | 90.6 | 0.33 |
| EDC/HOBt | DMF | 77.4 | 0.43 |
| EDC/HODhat | TFE/TCM[b] | 98.6 | <0.1 |
| EDC/HODhbt | TFE/TCM[b] | 96.2 | <0.1 |
| EDC/HOAt | TFE/TCM[b] | 98.2 | <0.1 |
| EDC/HOBt | TFE/TCM[b] | 90.0 | 0.20 |

[b]Combination solvent trifluoroethanol-chloroform (1:3 v/v) was used.

Following preliminary studies with simple di- and tripeptide models, XXVI, XXVII, XXVIII and XXX, a test peptide XXI was assembled. The coupling of Z-Gly-Gly-Val-OH to H-Ala-Gly-Gly-OMe is a sensitive test for the nature of both coupling reagent and base. Results for the reaction in DMF, in the presence of collidine are gathered in Table 11. HDATU was found to be more effective in preventing loss of configuration at valine than N-HATU and other coupling reagents. Epimerization levels up to 8.2% of the DL-form were noted according to the order: HDATU<N-HATU<HDTU<N-HBTU.

TABLE 11

Effect of Coupling Reagent, Base and Solvent on the Preservation of Configuration during the Formation of XXIX via [3 + 3] Coupling

| Coupling Reagent | Base | Solvent | Yield (%) | LDL (%) |
|---|---|---|---|---|
| HDATU | TMP(3) | DMF | 98.4 | 0.8 |
| HDTU | TMP(3) | DMF | 95.0 | 3.3 |
| N-HATU | TMP(3) | DMF | 96.6 | 2.4 |
| N-HBTU | TMP(3) | DMF | 85.6 | 8.2 |

EXAMPLE 26

In order to demonstrate the suitability of the new HODhat-based coupling reagent HDATU and compare its performance with that of the corresponding guanidinium/uronium analogs N-HATU and HDTU in solid-phase syntheses, 30 syntheses of the ACP segment H-Val-Gln-Ala-Ala-Ile-Asp-Tyr-Ile-Asn-GlyNH$_2$, (SEQ ID NO:2) were carried out by an Fmoc/tert-butyl protection scheme as described in Example 22. Polyethylene glycol-polystyrene (PEGPS)-resin bearing Fmoc-glycine was used as solid support. Peptide elongation was performed manually, coupling times being shortened and excesses of reagents being reduced in order to bring out the differences among the various coupling reagents studied. Under these conditions, incomplete incorporations were detected for Asn onto Gly, Ile onto Asn, Ile onto Asp, and Val onto Gln. Peptide purity was judged by reverse-phase HPLC analysis, after cleavage from the resin with TFA-H$_2$O (9:1) for 2 hours at room temperature. The results are collected in Table 12.

were used, 86% of acyl carrier protein (ACP) was obtained for HDATU, compared with 78% and 31% for N-HATU and HDTU, respectively.

In DMF under "1.5×1.5" conditions, the performance of HDATU may not have been as efficient as N-HATU with or without preactivation. In addition, for preparation of model pentapeptide H-Tyr-Aib-Aib-Phe-Leu-NH$_2$ (SEQ ID NO:3) which incorporates the highly hindered Aib-Aib unit, whether in DCM or DMF, HDATU was not able to equal the results obtained with N-HATU. For example, with 4 equivalents excess acid, 7 min preactivation and 30 min coupling time HDATU gave in DMF a peptide of 31% purity, whereas with N-HATU the purity was 91%.

TABLE 12

Distribution of Products Including Various Deletion Peptides, According to HPLC Analysis[a] for the Assembly of ACP via HODhat-HOAt- and HODhbt-Based Coupling Reagents[b]

| Entry | Coupling Method | Solvent | Equiv.[c] | Preact. (min) | Coupling (min) | ACP (%) | -2Ile (%) | -Ile (%) | -Ile (%) | Val (%) | Asn (%) | Unkwn[d] (%) |
|---|---|---|---|---|---|---|---|---|---|---|---|---|
| 1 | HDATU | DCM | 1.5 | 7 | 1.5 | 47 | 7 | 9 | 16 | 12 | 3 | — |
| 2 | N-HATU | DCM | 1.5 | 7 | 1.5 | 21 | 5 | 7 | 12 | 6 | 23 | — |
| 3 | HDTU | DCM | 1.5 | 7 | 1.5 | 4 | 13 | 5 | 13 | 2 | 3 | — |
| 4 | HDATU | DCM | 4 | 7 | 3 | 86 | — | — | 2 | 5 | 3 | — |
| 5 | N-HATU | DCM | 4 | 7 | 3 | 78 | — | — | 4 | 7 | 7 | — |
| 6 | HDTU | DCM | 4 | 7 | 3 | 31 | 5 | 7 | 26 | 3 | 4 | — |
| 7 | HDATU | DCM | 4 | 7 | 10 | 88 | — | — | — | 7 | — | — |
| 8 | N-HATU | DCM | 4 | 7 | 10 | 81 | — | — | — | 3 | 3 | — |
| 9 | HDATU | DMF | 1.5 | 0 | 1.5 | 68 | 3 | 10 | 17 | 2 | 1 | — |
| 10 | N-HATU | DMF | 1.5 | 0 | 1.5 | 87 | — | 3 | 1 | 2 | 7 | — |
| 11 | HDTU | DMF | 1.5 | 0 | 1.5 | 30 | 15 | 19 | 22 | 3 | 4 | — |
| 12 | HDATU | DMF | 2 | 0 | 5 | 97 | — | 1 | — | 2 | — | — |
| 13 | N-HATU | DMF | 2 | 0 | 5 | 94 | — | 1 | 1 | 2 | 2 | — |
| 14 | HDTU | DMF | 2 | 0 | 5 | 81 | 2 | 8 | 7 | 1 | 1 | — |
| 15 | HDATU | DMF | 1.5 | 7 | 1.5 | 60 | 1 | 7 | 7 | 1 | 5 | 16 |
| 16 | N-HATU | DMF | 1.5 | 7 | 1.5 | 77 | — | 2 | — | 3 | 11 | 7 |
| 17 | HDTU | DMF | 1.5 | 7 | 1.5 | 31 | 15 | 15 | 26 | — | 5 | 8 |
| 18 | HDATU | DMF | 4 | 7 | 1.5 | 72 | — | 5 | 3 | — | 18 | 2 |
| 19 | HDTU | DMF | 4 | 7 | 1.5 | 57 | 3 | 9 | 11 | 2 | 4 | 14 |
| 20 | HDATU | DMF | 3 | 7 | 3 | 64 | — | 1 | 1 | — | 4 | 20 |
| 21 | HDATU | DMF | 3 | 25 | 3 | 75 | — | 4 | 3 | 3 | 5 | 9 |
| 22 | HDATU | DMF | 4 | 7 | 30 | 95 | — | 1 | — | 2 | 1 | — |
| 23 | N-HATU | DMF | 4 | 7 | 30 | 86 | 4 | — | 2 | 1 | 1 | — |
| 24 | HDTU | DMF | 4 | 7 | 30 | 62 | 2 | 2 | — | 1 | 2 | 28 |
| 25 | DIC-HODhat | DMF | 4 | 7 | 30 | 55 | — | — | — | 12 | 30 | — |
| 26 | DIC-HODhbt | DMF | 4 | 7 | 30 | 29 | 9 | — | — | — | 3 | 5 |
| 27 | Pfp[e]-HODhat | DMF | 1.5[f] | 7 | 1.5 | 5 | — | — | — | — | — | — |
| 28 | Pfp[e]-HODhbt | DMF | 1.5[g] | 7 | 1.5 | 6 | — | — | — | — | — | — |
| 29 | Pfp[e]-HODhat | DMF | 3[f] | 7 | 30 | 90 | — | 1 | 1 | 7 | 1 | — |
| 30 | Pfb[e]-HODhbt | DMF | 3[g] | 7 | 30 | 87 | — | 3 | 3 | 6 | 1 | — |

[a]A reversed-phase C-18 column was used with elution by a linear gradient over 20 min of 0.1% TFA in MeCN and 0.1% aqueous TFA from 1:19 to 1:1, flow rate 0.1 ml/min.
[b]In all HDATU- or HODhat-mediated syntheses, a bright-yellow-to-orange-red color change was observed within 2–5 min during amino acid coupling, except for Ile and Val.
[c]Couplings were carried out in DMF or CH$_2$Cl$_2$ in the presence of 2 equivalents of DIEA per equivalent of Fmoc-amino acid/coupling reagent.
[d]Extra peaks which appeared after 20 min on the HPLC traces.
[e]Pentafluorophenyl ester.
[f]Only 1 equiv of HODhat was used as catalyst.
[g]Only 1 equiv of HODhbt was used as catalyst.

Analysis of the chromatograms indicated that HDATU is far more effective than HDTU under all conditions examined, and more effective even than N-HATU in many instances. Methylene chloride was found to be a particularly suitable solvent for HDATU-mediated ACP synthesis. Thus, under so called "1.5×1.5" conditions in CH$_2$Cl$_2$, HDATU gave the decapeptide in a purity of 47%, whereas N-HATU and HDTU led to only 21% and 4% of the desired product, respectively. When a 4-equiv excess of reagents and a 3-min coupling time However, in general HDATU was found to be the better reagent under normal conditions. Thus, while using a 2-equiv excess of reagents without preactivation for a 5-min coupling, ACP was obtained in 97% purity by HDATU, whereas the corresponding values were 94 and 81% for N-HATU and HDTU. With 4-equiv/30 min coupling conditions with a 7-min preactivation time, excellent purity (95%) was obtained for HDATU, whereas with N-HATU and HDTU, the ACP purity was only 86 and 62%, respectively.

When DIC/HODhat was used as a coupling reagent, satisfactory results were also obtained. Although not suitable under stringent conditions ("1.5×1.5"), HODhat could be used as an excellent catalyst and indicator in Fmoc-amino acid pentafluorophenyl (Pfp) ester couplings under normal conditions. A bright-yellow-to-orange-red color change was noted which is much clearer than the color change from bright-yellow to pale-yellow observed with HODhbt. In DMF under conditions involving 3 equiv of pentafluorophenyl-ester and a 30-mm coupling time, both HODhat and HODhbt gave the desired ACP product in a purity of over 85%.

EXAMPLE 27

Fmoc-Ile-ODhat

Method A. Under an atmosphere of dry $N_2$, a suspension of Fmoc-Ile-OH (0.3534 g, 1 mmol), HODhat (0.1805 g, 1.1 mmol) and $SOCl_2$ (0.73 ml, 10 mmol) in 8 ml of dry $CH_2Cl_2$ was refluxed overnight. Evaporation of $CH_2Cl_2$ and the excess of $SOCl_2$ gave a yellow solid, which was purified by flash chromatography through a short silica gel column with a mixture of EtOAc—$CH_2Cl_2$ (1:1 v/v) as eluent to give, after two recrystallizations from $CH_2Cl_2$-benzene-ether-hexane, 0.42 g (81%) of the analytically pure ester as a white solid: mp 160.5-162° C.; $^1H$ NMR ($CDCl_3$): δ 9.15 (dd, 1), 8.58 (dd, 1), 7.96 (dd, 1), 7.76 (dd, 2), 7.61 (dd, 2), 7.27-7.44 (m, 4), 5.20 (d, 1), 4.88 (q, 1), 4.49 (d, 2), 4.26 (t, 1), 2.21 (m, 1), 1.70 (m, 1), 1.34 (m, 1), 1.15 (d, 3), 1.05 (t, 3); IR (KBr): 1811(s, COO), 1738(vs, CONN), 1692(vs, NHCO) $cm^{-1}$. Anal. Calcd for $C_{27}H_{25}N_5O_5$: C, 64.91; H, 5.04; N, 14.02. Found: C, 64.77; H, 5.23; N, 13.94.

Method B. Under an atmosphere of dry $N_2$, 0.1854 g (0.5 mmol) of Fmoc-Ile-Cl was added with stirring to a solution of HODhat (0.0821 g, 0.5 mmol) and DIEA (95.8 µl, 0.55 mmol) in 10 ml of $CH_2Cl_2$ at 0° C. Stirring was continued at 0° C. for 30 min and then at room temperature for 5 hours. The resulting light yellow solution was diluted to 30 ml with $CH_2Cl_2$ and washed quickly with ice-cold brine (2×15 ml). After drying over $MgSO_4$ and removing the solvent, the light yellow sticky solid was recrystallized twice from $CH_2Cl_2$-ether-hexane to give the analytically pure above-identified ester as a white solid: mp 161-162° C.; NMR and IR spectra were identical with those of the sample obtained by Method A.

EXAMPLE 28

Utilizing the procedure described in footnote a of Table 2 of the article by Carpino, et al., *J. Org. Chem.* 1995, 60, 3561, the contents of which are incorporated by reference, the coupling of CBZ-Phe-Val-OH with H Pro-$NH_2$ to form CBZ-Phe-Val-Pro-$NH_2$ was investigated using various coupling reagents. Some of the coupling reagents used were those described elsewhere in the art while others used were coupling agents of the present invention. More specifically, for carbodiimide couplings, 0.105 mmol of Z-Phe-Val-OH, 0.1 mmol of H-Pro-$NH_2$, and 0.11 mmol of the coupling reagent noted hereinbelow in the table were dissolved in 1 mL of DMF or 1.3 mL of TFE/TCM (trifluoro ethanol/chloroform) (1:3), and the solution was cooled in an ice bath and treated with 0.11 mmol of EDC, EDC-HCl, or DCC. If a base is added, the number of equivalents is given. The mixture was stirred at 0° C. for 1 hour and at room temperature overnight. The mixture was diluted with 25 mL of EtOAc and extracted with 1 N NCl (2×5 mL), 1 N $NaHCO_3$ (2×5 mL), and saturated NaCl (2×5 mL), dried with $MgSO_4$, the solvent was removed, and the crude peptide was directly analyzed by HPLC. For onium salt couplings, 0.125 mmol of the acid, 0.125 mmol of amide, and 0.25 mmol of base in 1 mL of DMF was treated with 0.125 mmol of coupling reagent at 0° C. and the reaction mixture was stirred at 0° C. for 1 hour and at room temperature for 2-3 hours, after which the workup followed that described herein. In cases where an additive is used, one or more equivalents of base (given in parentheses) may be added. The amount of loss of configuration, as indicated by the presence of LDL epimer was determined. The results are tabulated in Table 13.

TABLE 13

[2 + 1] Segment coupling in solution (CBZ-Phe-Val-OH + H-Pro-$NH_2$).

| Coupling reagent | Base | Solvent | % of LDL epimer |
|---|---|---|---|
| O-HATU | DCHMA[b] (2 eq) | DMF | 7.91 |
| t-Bu-Dtp-OAt | DIEA (2eq) | DMF | 13.59 |
| t-Bu-Dtp-OAt | DCHMA[b] (2 eq) | DMF | 15.81 |
| O-HATU | DIEA (2 eq) | DMF | 10.07 |
| Dtp-OAt | TMP (2eq) | DMF | 1.77 |
| Dtp-OAt | TMP (2eq)/HOAt (1 eq) | DMF | 1.9 |
| t-Bu-Dtp-OAt | TMP (2eq) | DMF | 1.63 |
| O-HATU | DB(DMAP) (2 eq) | DMF | 1.59 |
| O-HATU | Proton Sponge (2 eq) | DMF | 2.78 |
| Dtp-OAt | DIEA (2 eq) | DMF | 16.04 |
| O-HATU | DIEA/TMP (1/1 eq) | DMF | 10.17 |

EXAMPLE 29

Using the procedure as described in the article by Carpino, et al. in *Tetrahedron* 1999, 55, 6813, the contents of which are incorporated by reference, the coupling of Fmoc-Asp (t-Bu)-Phe-OH and F-moc-Lys (BOC)-PAL-PEG to form Fmoc-Asp-(t-Bu)-Phe-Lys(-Boc)-PAL-PEG was conducted. Some of the coupling reagents used were those described elsewhere while others used were those of the present invention. Coupling reactions were carried out by deblocking 50 mg of H-Lys(Boc)-PAL-PEG-PS resin by means of 20% piperidine/DMF for 7 min, washing the resin with DMF, DCM and DMF (3×5 mL each) and then adding a 5-fold excess (0.0475 mmol) of Fmoc-Asp(O-t-Bu)-Phe-OH (26.5 mg), a 5-fold excess of the coupling reagent noted in Table 14 and 11.5 mg (0.095 mmol) of TMP or 12.3 mg of DIEA (10-fold excess) of the base, if any. In each case the coupling reagent and the base were dissolved in 0.2 mL of the solvent and the resulting solution added to the resin in a small syringe which served as the reactor. Dissolution required about 1 min or less and care was taken to add the solution as soon as possible after everything dissolved. This method is referred to as the "low preactivation" method. Where preactivation was involved, the times are recorded. The mixture was stirred gently every 10 min with a Teflon rod for approximately 1 hour and then allowed to stand for 12 hours after which the resin was washed with DMF and DCM (3×5 mL each) and deblocked by treatment with 3 mL of TFA/$H_2O$ (9:1) for 1½ hour at room temperature. The solvent was removed in vacuo and the residue dissolved in $CH_3$—CN for direct injection onto an HPLC column under the following conditions: 4µ 60 A, $C_{18}$ Waters Nova-pak column, 3.9×150 mm; flow rate 1 mL/min; Waters 996 PDA detector; linear gradient 10/30 in 20 min and then isocratic 30/70 for 20 min with $CH_3CN/H_2O$/0.1% TFA; $R_t$ (LLL-) 28.5 min, (LDL-) 30.5 min. The amount of loss of configuration as indicated by the presence of LDL epimer was determined. The results are tabulated in Table 14.

TABLE 14

[2 + 1] Segment coupling under solid phase conditions[6]
(FmocAsp(tBu)-Phe-OH + H-Lys(BOC)-PAL-PEG).

| Coupling reagent | Base | Solvent | % of LDL epimer |
|---|---|---|---|
| N-HATU | TMP (2 eq) | DMF | 18.88 |
| N-HATU | TMP (2 eq) | DCM | 35.95 |
| Dtp-OAt | TMP (2 eq) | DCM | 14.70 |
| t-Bu-Dtp-OAt | TMP (2 eq) | DCM | 12.94 |
| Dtp-OAt | TMP (2 eq) | DMF | 42.82 |

EXAMPLE 30

Utilizing the procedure of Example 29, and utilizing CBZ-Gly-Gly-Val-OH and H-Ala-Gly-Gly-PAL-Peg, CBZ-Gly-Gly-Val-Ala-Gly-Gly-PAL-PEG (SEQ ID NO:4) was formed using t-Bu-DtP-OAt of the present invention and O-HATU. The amount of loss of configuration was determined by measuring the amount of LDL epimer formed. The results are indicated in Table 15 hereinbelow.

TABLE 15

[3 + 3] Segment coupling under solid phase conditions
(CBZ-Gly-Gly-Val-OH + H-Ala-Gly-Gly-PAL-PEG).

| Coupling reagent | Base | Solvent | % of LDL epimer |
|---|---|---|---|
| t-Bu-Dtp-OAt | TMP | DMF | 1.99 |
| O-HATU | TMP | DMF | 2.09 |

The high coupling efficiency of the coupling reagents of the present invention including t-Bu-Dtp-OAt was emphasized by solid phase synthesis of ACP decapeptide under the so-called "1.5×1.5" protocol. Under these demanding conditions the coupling efficiency of various coupling reagents can be easily brought out. The couplings are carried out for 1.5 minutes using a 1.5-eq excess of protected amino acids and 1.5 eq of coupling reagent in the presence of 3 eq of base.

For manual solid phase syntheses of ACP under the 1.5×1.5 protocol, using the procedure of Carpino, et al., in *J. Chem. Soc. Chem. Comm*, 1994, 201, the contents of which are incorporated by reference and using O-HATU, Dtp-OAt and t-Bu-Dtp-OAt the purity of the crude peptide was 76%, 60% and 74%, respectively. The new phosphorus-based coupling reagent therefore at least equals the effectiveness of O-HATU, considered the best of the previously described reagents.

The above preferred embodiments and examples are given to illustrate the scope and spirit of the present invention. These embodiments and examples will make apparent to those skilled in the art other embodiments and examples. These other embodiments are within the contemplation of the present invention. Therefore, the present invention should be limited only by the appended claims.

---

What is claimed is:

1. A compound or a salt consisting of an anion and, wherein the compound or the cation of the salt is of the formula

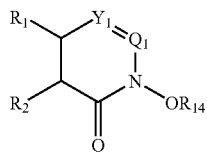

wherein $R_1$ and $R_2$ taken together with the carbon atoms to which they are attached form a pyridyl ring, said pyridyl ring may be unsubstituted or substituted with a lower alkyl group or an electron donating group;

$Y_1$ is N;

$Q_1$ is $CR_{16}$;

$R_{16}$ is H or lower alkyl;

$R_{14}$ is a positively charged electron withdrawing group,

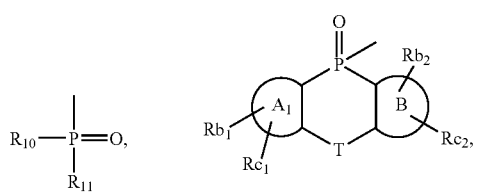

$SO_2R_{17}$, lower alkyl carbonyl, lower arylalkyl carbonyl, aryl carbonyl, lower alkyl aryl, or $BLK_1-AA_1$ $R_{17}$ is aryl, aryl lower alkyl or lower alkyl;

$AA_1$ is an amino acid or peptide less a hydrogen atom on the N-terminus and an OH on the C-terminus;

$BLK_1$ is an amino protecting group, $R_{10}$ is $OR_{12}$, lower alkyl, aryl, aryl lower alkyl, lower cycloalkyl, lower cycloalkyl lower alkyl, heterocyclic, heterocyclic lower alkyl, lower cycloalkenyl, or lower cycloalkenyl lower alkyl;

$R_{11}$ is $OR_{13}$, lower alkyl, aryl, aryl lower alkyl, lower cycloalkyl, lower cycloalkyl lower alkyl, heterocyclic, heterocyclic lower alkyl, lower cycloalkenyl or lower cycloalkenyl lower alkyl;

and $R_{10}$ and $R_{11}$ may optionally be connected by a bridging group selected from the group consisting of O, S, $NR_{30}$, or $(CHR_{30})_m$, wherein each $R_{30}$ is independently lower alkyl or hydrogen and m is 1-3; and $R_{12}$ and $R_{13}$ are independently lower alkyl, lower cycloalkyl, lower cycloalkyl lower alkyl, heterocyclic, heterocyclic lower alkyl, lower cycloalkenyl or lower cyclalkenyl lower alkyl;

ring $A_1$ and ring B are independently an aromatic ring containing 6 to 14 ring carbon atoms or cycloalkenyl or cycloalkyl, each containing 5 to 14 ring carbon atoms, and $R_{b1}, R_{c1}, R_{b2}, R_{c2}$ are independently hydrogen, lower alkyl or electron donating group;

T is $CHR_{31}$, O, S or $NR_{30}$; and $R_{31}$ is hydrogen or lower alkyl.

2. The salt according to claim 1 wherein $R_{14}$ is a positively charged electron withdrawing group.

3. The salt according to claim 2 wherein $R_{14}$ is an electron withdrawing group of the formula

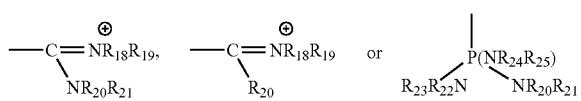

wherein $R_{18}, R_{19}, R_{20}, R_{21}, R_{22}, R_{23}, R_{24}$ and $R_{25}$ are independently hydrogen, lower alkyl, or lower alkoxy lower alkyl or $R_{18}$ and $R_{19}$ taken together with the atoms to which they are attached form a ring containing up to 6 ring atoms and up to a total of 5 carbon ring atoms or $R_{20}$ and $R_{21}$ taken together with the nitrogen atom to which they are attached form a 5 or 6 membered nitrogen containing heterocyclic ring containing up to a total of 5 carbon ring atoms or $R_{18}$ and $R_{20}$ taken together with the nitrogen atom and the carbon atom to which they are attached form a heterocyclic ring, or $R_{22}$ and $R_{23}$ taken together with the atoms to which they are attached form a ring containing up to 6 ring atoms and up to a total of 5 carbon atoms or $R_{24}$ and $R_{25}$ taken together with the carbon atoms to which they are attached form a ring containing up to 6 ring atoms and up to a total of 5 carbon atoms.

4. The salt according to claim 3 wherein $R_{14}$ is

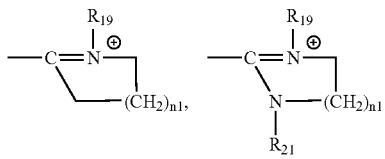

wherein $R_{19}$, $R_{21}$, $R_{24}$ and $R_{25}$ are independently hydrogen, or lower alkyl or lower alkoxy lower alkyl; and $n_1$ is 0 or 1.

5. The salt according to claim 4 wherein $R_{19}$ and $R_{21}$ or $R_{24}$ and $R_{25}$ are the same.

6. The salt according to claim 1 wherein $R_{14}$ is

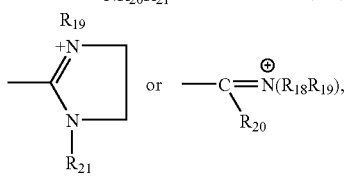

wherein $R_{18}$, $R_{19}$, $R_{20}$, $R_{21}$, $R_{22}$, $R_{23}$, $R_{24}$ and $R_{25}$ are independently hydrogen, methyl, ethyl, propyl, butyl, pentyl, or $CH_2CH_2OCH_2CH_3$.

7. The salt according to claim 6 wherein $R_{23}$, $R_{22}$, $R_{20}$, $R_{21}$, $R_{24}$, and $R_{25}$ are the same or $R_{18}$, $R_{19}$ and $R_{20}$ are the same or $R_{19}$ and $R_{21}$ are the same.

8. The compound or salt according to claim 1 wherein $R_{14}$ is

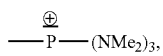

lower alkyl carbonyl, lower arylalkyl carbonyl, aryl carbonyl,

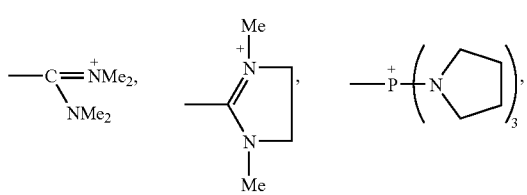

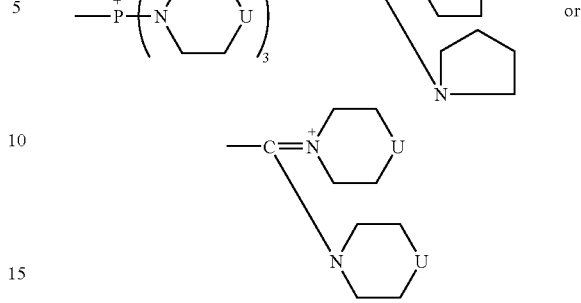

wherein U is NH, or O.

9. The compound according to claim 1 wherein $R_{14}$ is

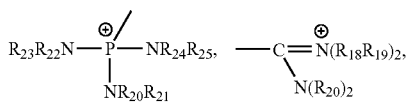

10. A compound or a salt consisting of an anion and cation, wherein the compound or the cation of the salt is of the formula $$\begin{array}{c}R_1\\ \phantom{x}\\ R_2\end{array}\!\!\!\!\!\!\begin{array}{c}Y_1\!=\!Q_1\\ \phantom{x}\\ \phantom{x}\end{array}\!\!\!\!N\!-\!OR_{14}$$

wherein $R_1$ and $R_2$ taken together with the carbon atoms to which they are attached form a pyridyl ring, said pyridyl ring may be unsubstituted or substituted with a lower alkyl group or an electron donating group;

Y is N;

$Q_1$ is $CR_{16}$;

$R_{16}$ is H or lower alkyl;

$R_{14}$ is $$\begin{array}{c}O\\ \|\\ -P-R_{10}\\ |\\ R_{11}\end{array}$$

$R_{10}$ is $OR_{12}$, lower alkyl, aryl, or aryl lower alkyl;

$R_{11}$ is $OR_{13}$, lower alkyl, aryl, or aryl lower alkyl;

and $R_{10}$ and $R_{11}$ may optionally be connected by a bridging group selected from the consisting of O, S, NH, and $(CH_2)_m$;

m is 1-3; and $R_{12}$ and $R_{13}$ are independently lower alkyl, aryl, or aryl lower alkyl.

11. The compound according to claim 1 wherein

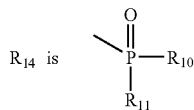

$R_{14}$ is wherein $R_{10}$ and $R_{11}$ are independently lower alkyl or aryl.

12. The compound according to claim 1 wherein

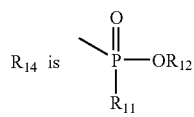

$R_{14}$ is wherein $R_{11}$ and $R_{12}$ are independently lower alkyl or aryl.

13. The compound or salt according to claim 1 wherein the compound or the cation of the salt has the formula

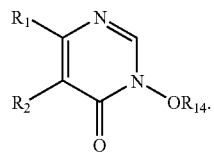

wherein $R_1$, $R_2$, $Q_2$ and $R_{14}$ are as defined in claim 1.

14. A compound or a salt consisting of an anion and cation, wherein the compound or the cation of the salt has the formula

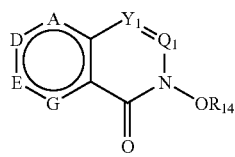

wherein
A is N or $CR_{24}$;
D is $CR_{25}$ or N;
E is $CR_{26}$ or N;
G is $CR_{27}$ or N;
$R_{24}$, $R_{25}$, $R_{26}$ and $R_{27}$ are independently hydrogen, a lower alkyl group or an electron donating group, or $R_{25}$ and $R_{26}$ or $R_{24}$ and $R_{25}$ or $R_{26}$ and $R_{27}$ taken together with the carbon atoms to which they are respectively attached form an aryl ring;
wherein one of A, D, E and G, is N;
$Y_1$ is N;
$Q_1$ is $CR_{16}$;
$R_{16}$ is H or lower alkyl;
$R_{14}$ is a positively charged electron withdrawing group,

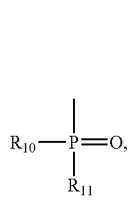 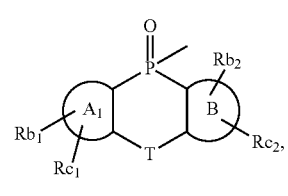

$SO_2R_{17}$, lower alkyl carbonyl, aryl carbonyl, lower alkyl aryl, or $BLK_1$-$AA_1$
$R_{17}$ is aryl, aryl lower alkyl or lower alkyl;
$AA_1$ is an amino acid or peptide less a hydrogen atom on the N-terminus and an OH on the C-terminus;
$BLK_1$ is an amino protecting group, $R_{10}$ is $OR_{12}$, lower alkyl, aryl, aryl lower alkyl, lower cycloalkyl, lower cycloalkyl lower alkyl, heterocyclic, heterocyclic lower alkyl, lower cycloalkenyl, or lower cycloalkenyl lower alkyl;
$R_{11}$ is $OR_{13}$, lower alkyl, aryl, aryl lower alkyl, lower cycloalkyl, lower cycloalkyl lower alkyl, heterocyclic, heterocyclic lower alkyl, lower cycloalkenyl or lower cycloalkenyl lower alkyl;
and $R_{10}$ and $R_{11}$ may optionally be connected by a bridging group selected from the group consisting of O, S, $NR_{30}$, or $(CHR_{30})_m$, wherein each $R_{30}$ is independently lower alkyl or hydrogen and m is 1-3; and
$R_{12}$ and $R_{13}$ are independently lower alkyl, lower cycloalkyl, lower cycloalkyl lower alkyl, heterocyclic, heterocyclic lower alkyl, lower cycloalkenyl or lower cyclalkenyl lower alkyl;
ring $A_1$ and ring B are independently an aromatic ring containing 6 to 14 ring carbon atoms or cycloalkenyl or cycloalkyl, each containing 5 to 14 ring carbon atoms, and
$R_{b1}$, $R_{c1}$, $R_{b2}$, $R_{c2}$ are independently hydrogen, lower alkyl or electron donating group;
T is $(CHR_{31})$, O, S or $NR_{31}$; and
$R_{31}$ is hydrogen or lower alkyl.

15. The compound or salt according to claim 14 where the compound or the cation has the formula

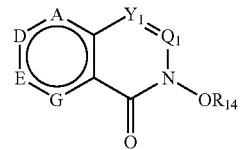

wherein
A is N or $CR_{24}$;
D is $CR_{25}$ or N;
E is $CR_{26}$ or N;
G is $CR_{27}$ or N;
$R_{24}$, $R_{25}$, $R_{26}$ and $R_{27}$ are independently hydrogen or lower alkyl;
wherein one of A, D, E and G, is N;
$Y_1$ is N;
$Q_1$ is $CR_{16}$;
$R_{16}$ is H or lower alkyl;
$R_{14}$ is a positively charged electron withdrawing group,

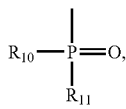 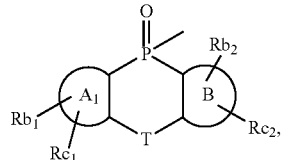

$SO_2R_{17}$, lower alkyl carbonyl, aryl carbonyl, loweralkyl aryl, or $BLK_1$-$AA_1$
$R_{17}$ is aryl, aryl lower alkyl or lower alkyl;
$AA_1$ is an amino acid or peptide less a hydrogen atom on the N-terminus and an OH on the C-terminus;
$BLK_1$ is an amino protecting group, $R_{10}$ is $OR_{12}$, lower alkyl, aryl, aryl lower alkyl, lower cycloalkyl, lower cycloalkyl lower alkyl, heterocyclic, heterocyclic lower alkyl, lower cycloalkenyl, or lower cycloalkenyl lower alkyl;

$R_{11}$ is $OR_{13}$, lower alkyl, aryl, aryl lower alkyl, lower cycloalkyl, lower cycloalkyl lower alkyl, heterocyclic, heterocyclic lower alkyl, lower cycloalkenyl or lower cycloalkenyl lower alkyl;

and $R_{10}$ and $R_{11}$ may optionally be connected by a bridging group selected from the group consisting of O, S, $NR_{30}$, or $(CHR_{30})_m$, wherein each $R_{30}$ is independently lower alkyl or hydrogen and m is 1-3; and $R_{12}$ and $R_{13}$ are independently lower alkyl, lower cycloalkyl, lower cycloalkyl lower alkyl, heterocyclic, heterocyclic lower alkyl, lower cycloalkenyl or lower cyclalkenyl lower alkyl;

ring $A_1$ and ring B are independently an aromatic ring containing 6 to 14 ring carbon atoms or cycloalkenyl or cycloalkyl, each containing 5 to 14 ring carbon atoms, and $R_{b1}, R_{c1}, R_{b2}, R_{c2}$ are independently hydrogen, lower alkyl or electron donating group;

T is $(CHR_{31})$, O, S or $NR_{31}$; and $R_{31}$ is hydrogen or lower alkyl.

16. The compound according to claim 15 wherein $R_{14}$ is

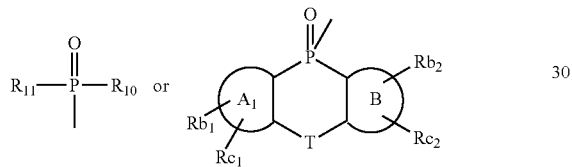

wherein $R_{10}$ and $R_{11}$, $R_{b1}$, $R_{b2}$, $R_{c1}$, $R_{c2}$ are independently hydrogen or lower alkyl and T is O, $CH_2$, NH or S and ring $A_1$ and ring B are independently an aromatic ring containing 6 to 14 ring carbon atoms.

17. The compound according to claim 1 wherein

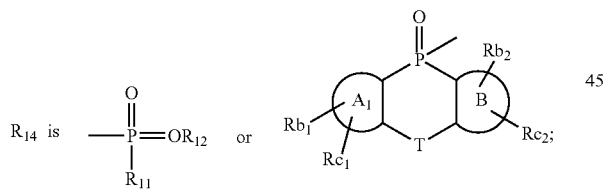

wherein $R_{12}, R_{11}, R_{b1}, R_{b2}, R_{c1}$ and $R_{c2}$ are independently hydrogen or lower alkyl;

ring $A_1$ and ring B are independently phenyl; and

T is $CH_2$, O, S or NH.

18. The compound according to claim 1, wherein the compound is a salt, the cation of which has the formula

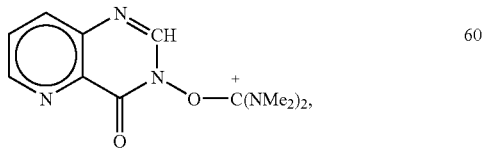

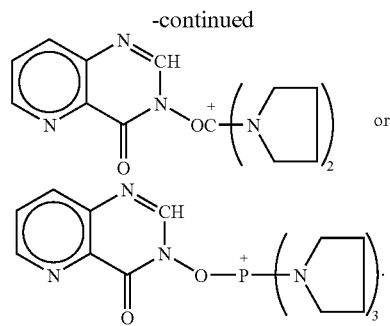

19. The compound according to claim 1 wherein the compound has the formula

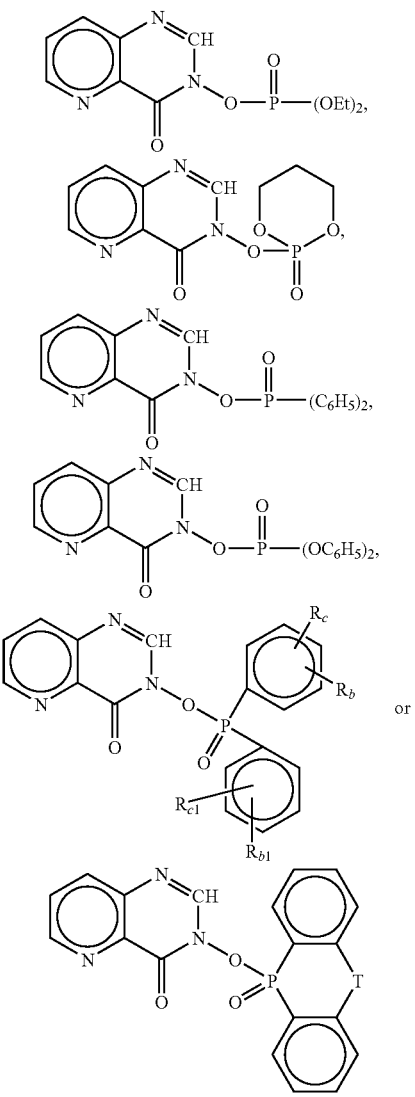

wherein $R_b$, $R_{b1}$, $R_c$, are independently lower alkyl or hydrogen and T is $CH_2$, NH, O or S.

* * * * *

UNITED STATES PATENT AND TRADEMARK OFFICE
CERTIFICATE OF CORRECTION

PATENT NO.        : 7,812,158 B2
APPLICATION NO.   : 10/577352
DATED             : October 12, 2010
INVENTOR(S)       : Louis A. Carpino et al.

It is certified that error appears in the above-identified patent and that said Letters Patent is hereby corrected as shown below:

Column 30, Line 63:
"Hoffman" should be --Hoffinan--

Column 67, Line 25, Claim 1:
"A compound or a salt consisting of an anion and," should be --A compound or a salt consisting of an anion and cation ,--

Column 71, Line 20, Claim 13

" 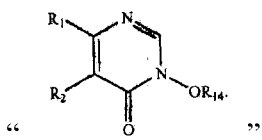 "

should be

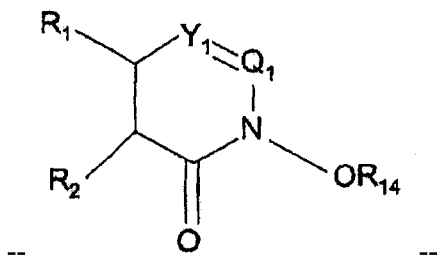

--                                    --

Signed and Sealed this
Fourth Day of October, 2011

David J. Kappos
*Director of the United States Patent and Trademark Office*